(12) United States Patent
Mersch et al.

(10) Patent No.: US 7,862,219 B2
(45) Date of Patent: Jan. 4, 2011

(54) OPTICAL FIBER LIGHT DIFFUSING DEVICE

(75) Inventors: Steven H. Mersch, Germantown, OH (US); Ronald R. Zimmermann, Woodbury, MN (US); Merrill A. Biel, Mendota Heights, MN (US)

(73) Assignee: Advanced Photodynamic Technologies, Inc., Minneapolis, MN (US)

( * ) Notice: Subject to any disclaimer, the term of this patent is extended or adjusted under 35 U.S.C. 154(b) by 108 days.

(21) Appl. No.: 12/288,649

(22) Filed: Oct. 22, 2008

(65) Prior Publication Data

US 2010/0097822 A1    Apr. 22, 2010

(51) Int. Cl.
    *F21V 7/04* (2006.01)
(52) U.S. Cl. .................. 362/558; 362/551; 362/582; 385/123
(58) Field of Classification Search ............ 362/572, 362/558, 551, 554–556, 582; 385/123, 147
    See application file for complete search history.

(56) References Cited

U.S. PATENT DOCUMENTS

| | | | |
|---|---|---|---|
| 3,931,518 A | 1/1976 | Miller | 250/227 |
| 4,660,925 A | 4/1987 | McCaughan, Jr. | 350/96.15 |
| 4,693,556 A | 9/1987 | McCaughan, Jr. | 350/320 |
| 4,842,356 A | 6/1989 | Mori | 350/96.1 |
| 4,986,628 A | 1/1991 | Lozhenko et al. | 350/96.29 |
| 4,995,691 A | 2/1991 | Purcell, Jr. | 350/96.15 |
| 5,074,632 A | 12/1991 | Potter | 385/123 |
| 5,363,458 A | 11/1994 | Pan et al. | 385/31 |
| 5,373,571 A | 12/1994 | Reid et al. | 385/31 |
| 5,536,265 A | 7/1996 | van den Bergh et al. | 606/2 |
| 5,695,583 A | 12/1997 | van den Bergh et al. | 156/153 |
| 5,918,974 A | 7/1999 | Suzuki et al. | |
| 5,999,678 A | 12/1999 | Murphy-Chutorian et al. | 385/117 |
| 6,048,359 A | 4/2000 | Biel | 607/92 |
| 6,174,291 B1 * | 1/2001 | McMahon et al. | 600/564 |
| 6,343,174 B1 | 1/2002 | Neuberger | 385/123 |
| 6,551,346 B2 | 4/2003 | Crossley | 607/88 |
| 6,576,163 B2 * | 6/2003 | Mersch | 264/1.1 |
| 6,774,278 B1 | 8/2004 | Ragheb et al. | 623/11 |
| 7,252,677 B2 | 8/2007 | Burwell et al. | 607/88 |
| 7,274,847 B2 | 9/2007 | Gowda et al. | 385/117 |
| 2002/0094161 A1* | 7/2002 | Maitland | 385/31 |
| 2002/0138073 A1* | 9/2002 | Intintoli et al. | 606/15 |
| 2003/0147256 A1 | 8/2003 | Kraft | 362/560 |
| 2007/0129712 A1 | 6/2007 | Neuberger | 606/15 |
| 2007/0225695 A1 | 9/2007 | Mayer et al. | 606/15 |
| 2007/0263975 A1 | 11/2007 | Boutoussov et al. | 385/146 |
| 2007/0286560 A1 | 12/2007 | Nakamura et al. | 385/124 |
| 2008/0058629 A1* | 3/2008 | Seibel et al. | 600/368 |
| 2008/0124508 A1 | 5/2008 | Sato | 428/38 |
| 2008/0131065 A1 | 6/2008 | Windeler et al. | 385/124 |

OTHER PUBLICATIONS

International Search Report and Written Opinion.

* cited by examiner

*Primary Examiner*—Thomas M Sember
(74) *Attorney, Agent, or Firm*—Dobrusin & Thennisch PC

(57) ABSTRACT

A light diffusing device for use in photodynamic therapy has a progressively distally increased exposed amount of core fiber defining a light emitting section. Excessive light energy emission is thus prevented access to proximal locations and provides an increased amount of available light energy at distal locations, thus permitting an even emission of light energy along the light emitting section.

34 Claims, 52 Drawing Sheets

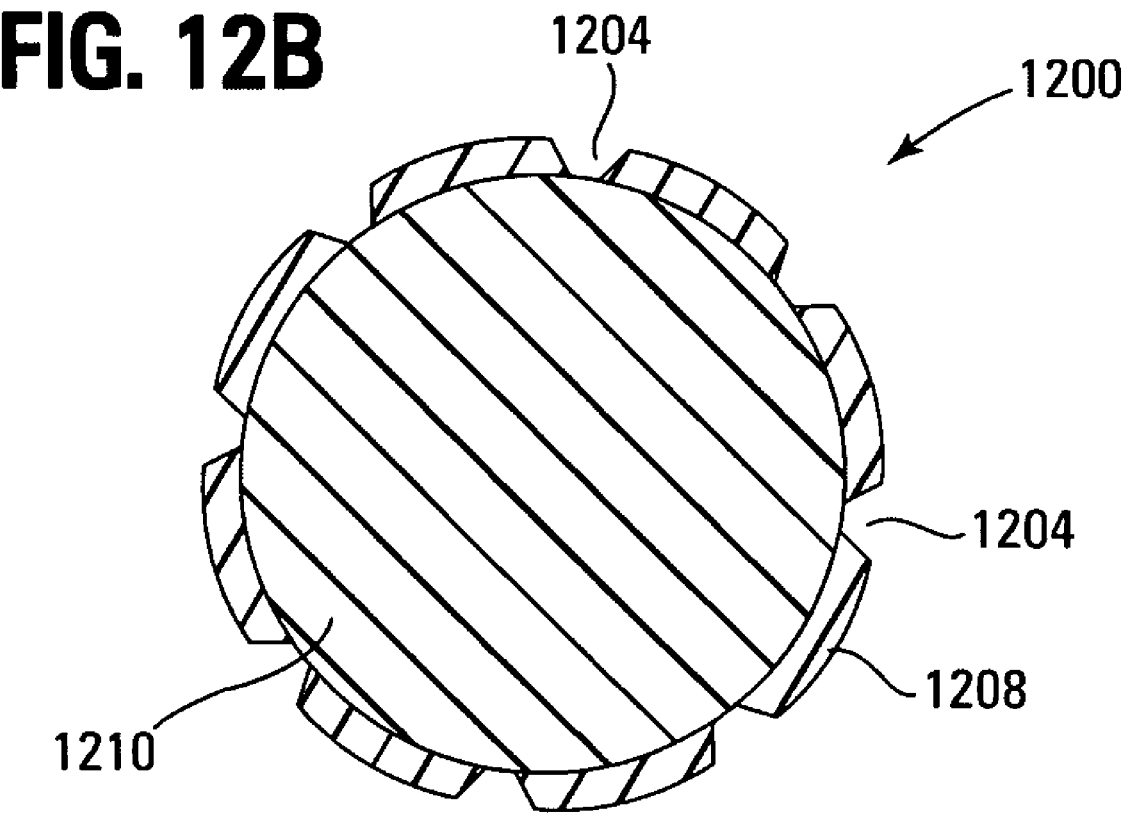

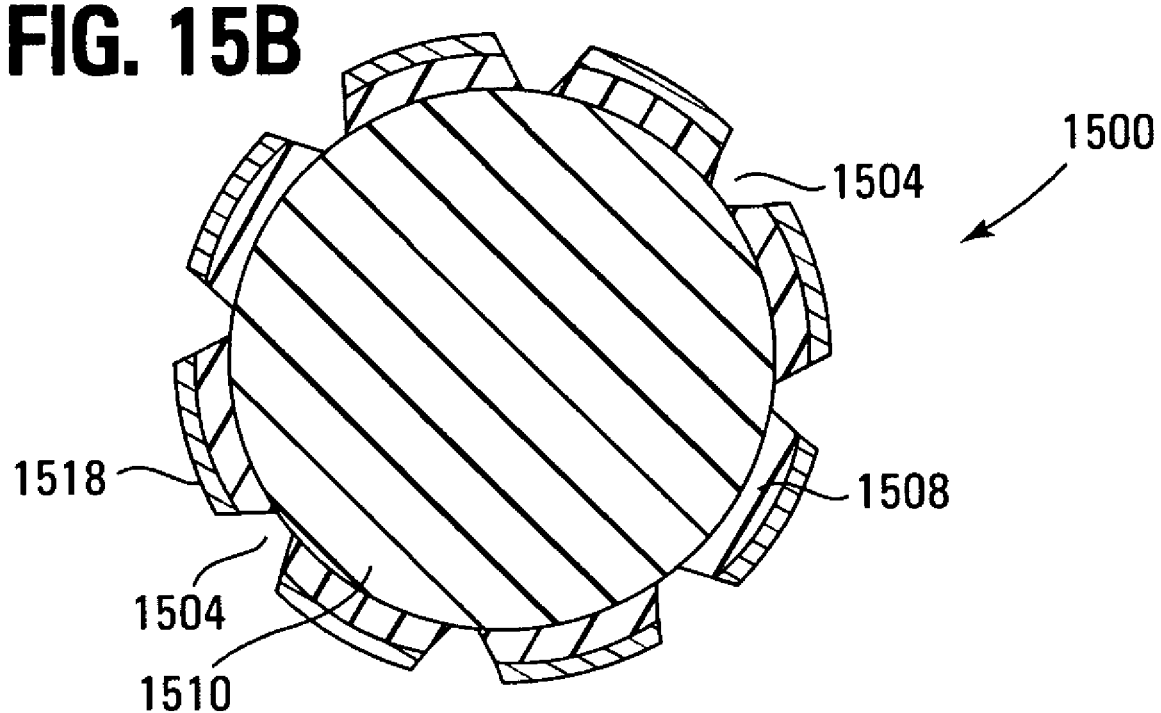

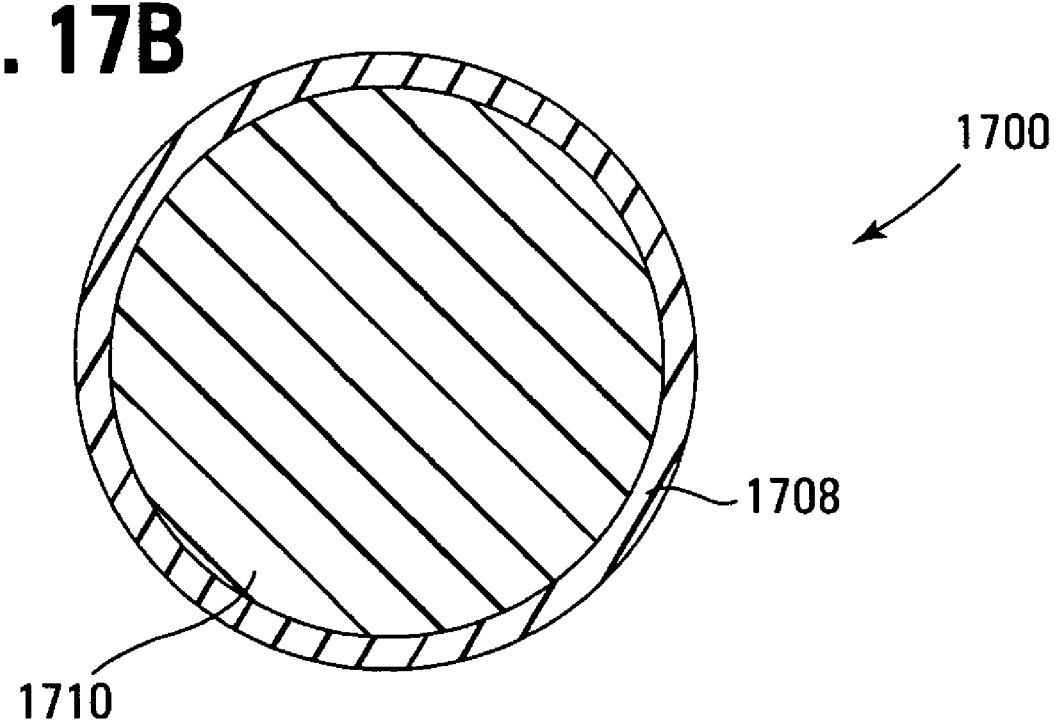

OPTICAL FIBER LIGHT DIFFUSING DEVICE

GOVERNMENT LICENSE RIGHTS

The U.S. government has a paid-up license in this invention and the right in limited circumstances to require the patent owner to license others on reasonable terms as provided by the terms of Grant No. 2R44 A1041866-02A2 awarded by the National Institute of Health: National Institute of Allergy and Infectious Diseases.

FIELD OF THE INVENTION

The present invention relates to devices used for light transmission as are used in photodynamic therapy to deliver light energy to a treatment site.

BACKGROUND

Photodynamic therapy (PDT) is a medical treatment involving the use of a photosensitizing agent which is exposed to a specific wavelength of light to create oxygen radicals, resulting in the destruction of cancer cells, bacteria, viruses or fungi. A PDT system consists of three principal components: a photosensitizing agent, a light source (typically a laser) and a light delivery means (typically optical fiber based).

PDT involves the use of a photosensitizing agent that is relatively selectively concentrated in cancer cells or microbiological pathogen sites. Depending on the type of photosensitizer, it may be injected intravenously, ingested orally or applied topically. After application of the photosensitizing agent it is selectively retained by diseased tissue so that after a period of time, determined by the kinetics of the compound's distribution, there is more photosensitizing agent absorbed by the diseased tissue than in normal tissue. The photosensitizing agent is then activated by exposure to a specific wavelength of light matching the absorption rates. This results in tissue necrosis via several mechanisms including oxygen radical production as well as vascular shutdown to the diseased tissue. Because there is less photosensitizer in the adjacent normal tissue, only the diseased tissue necroses and the normal tissue is preserved when the correct light dose rate for that tissue is administered. The advantage of PDT over conventional treatment such as surgery, radiation and chemotherapy is its relatively selective destruction of diseased tissue with normal tissue preservation.

The light distribution properties of the light delivery device can have direct impact on the effectiveness of the light application and thus the efficacy of the PDT treatment. The challenge of the light delivery devices is to ensure the light distribution is equal along the entire length of the light emitting section of the device. Several types of distributing devices have been developed in attempts to more evenly and safely distribute the light and energy radiating from the device used to deliver the laser energy. One type of diffusing device involves a fiber optic microlens which is able to transfer a divergent light beam to a limited area tissue area. A light diffusion device, as disclosed in U.S. Pat. No. 4,660,925 to McCaughen, Jr. consists of a fiber cylindrical diffuser which emits a cylindrical scattering pattern of light output with respect to the cylindrical axis of the optical fiber, using a spaced series of rings of varying intensity light. Yet another diffusion device as disclosed in U.S. Pat. No. 4,693,556 to McCaughen, Jr. consists of a fiber optic spherical diffuser or "light bulb" which produces a spherical scattering light field. Each of these diffusing devices produces a light field of varying intensity over the area of emitted light from the optical fiber which may result in an uneven activation of the photosensitizer over the treatment area. In still another device, as disclosed in U.S. Pat. Nos. 5,536,265 and 5,695,583 to van den Bergh et al., the cladding is removed from a plastic optical fiber and replaced by a scattering medium which may or may not be roughened, resulting in a light emission area. This device is problematic in that the distal area of the light emitting area is less intense than the more proximal areas of the light emitting area of the device. What is clearly needed, then, is an improved optical fiber that is able to more evenly deliver light energy over a wider surface area.

It is understood that the present invention as described and claimed herein can be used for many additional purposes, therefore the invention is within the scope of other fields and uses and not so limited.

SUMMARY

In one aspect, the present invention comprises a light diffusing device having an optical fiber defining a longitudinal dimension, a lateral dimension and a distal end. A core fiber is at least partially covered by cladding and a light emitting section is formed by selectively removing cladding such that a progressively distally increasing surface area of core fiber is exposed, resulting in an even distribution of light emitted from the light emitting section. The light emitting section further defines a distal end and a proximal end.

In another aspect, the present invention comprises a light diffusing device having an optical fiber defining a length, a diameter, a proximal end, a distal end and a core fiber at least partially covered by cladding. A light emitting section is formed by removing the cladding covering the light emitting section and selectively removing core fiber thereby progressively distally increasing the surface area of exposed core fiber, resulting in an even distribution of light emitted from the light emitting section. The light emitting section further defines a distal end and a proximal end.

In a further aspect, the present invention comprises a light diffusing device having an optical fiber defining a length, a diameter, a proximal end and a distal end and a core fiber at least partially covered by cladding wherein a light emitting section is formed by selectively removing cladding to form at least a single light port such that a progressively distally increasing surface area of core fiber is exposed, resulting in an even distribution of light emitted from the light emitting section. The light emitting section further defines a distal end and a proximal end.

BRIEF DESCRIPTION OF THE DRAWINGS

FIG. 12B is a lateral cross section taken through the lines 12B-12B as shown in FIG. 12.

FIG. 15B is a lateral cross section taken through the lines 15B-15B as shown in FIG. 15.

FIG. 17B is a lateral cross section taken through the lines 17B-17B as shown in FIG. 17, showing openings through the cladding core fiber.

DETAILED DESCRIPTION

Figure 1:
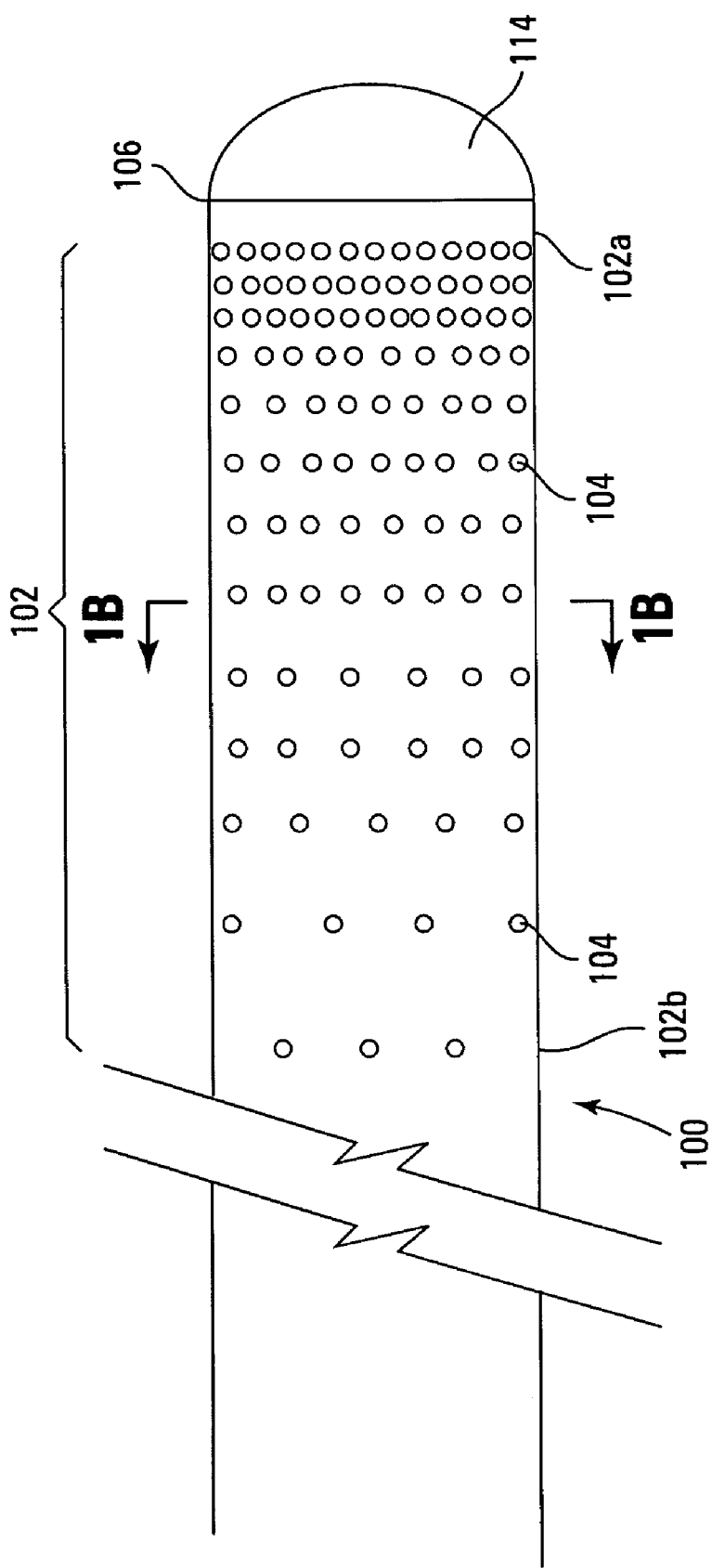
FIG. 1 shows the distal end of an embodiment of the light diffusing device of the present invention having a plurality of similarly sized open areas through the cladding distally progressively closer in proximity to each other.

The particulars shown herein are by way of example and for purposes of illustrative discussion of the invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.

Nomenclature
10 Optical Fiber
100 Light Diffusing Device
102 Light Emitting Section
102a Distal End (Light Emitting Section)
102b Proximal End (Light Emitting Section)
104 Light Port
105 Proximal End
106 Distal End
108 Cladding
110 Core Fiber
112 Connector
114 End Piece
200 Light Diffusing Device
202 Light Emitting Section
202a Distal End (Light Emitting Section)
202b Proximal End (Light Emitting Section)
204 Light Port
205 Proximal End
206 Distal End
208 Cladding
210 Core Fiber
212 Connector
214 End Piece
300 Light Diffusing Device
302 Light Emitting Section
302a Distal End (Light Emitting Section)
302b Proximal End (Light Emitting Section)

304 Light Port
305 Proximal End
306 Distal End
308 Cladding
310 Core Fiber
312 Connector
314 End Piece
400 Light Diffusing Device
402 Light Emitting Section
402a Distal End (Light Emitting Section)
402b Proximal End (Light Emitting Section)
404 Light Port
405 Proximal End
406 Distal End
408 Cladding
410 Core Fiber
412 Connector
414 End Piece
500 Light Diffusing Device
502 Light Emitting Section
502a Distal End (Light Emitting Section)
502b Proximal End (Light Emitting Section)
504 Light Port
505 Proximal End
506 Distal End
508 Cladding
510 Core Fiber
512 Connector
514 End Piece
600 Light Diffusing Device
602 Light Emitting Section
602a Distal End (Light Emitting Section)
602b Proximal End (Light Emitting Section)
604 Removed Core Fiber Section
605 Proximal End
606 Distal End
608 Cladding
610 Core Fiber
612 Connector
614 End Piece
700 Light Diffusing Device
702 Light Emitting Section
702a Distal End (Light Emitting Section)
702b Proximal End (Light Emitting Section)
704 Removed Core Fiber Section
705 Proximal End
706 Distal End
708 Cladding
710 Core Fiber
712 Connector
714 Piercing Tip
800 Light Diffusing Device
802 Light Emitting Section
802a Distal End (Light Emitting Section)
802b Proximal End (Light Emitting Section)
804 Removed Core Fiber Section
805 Proximal End
806 Distal End
808 Cladding
810 Core Fiber
812 Connector
814 End Piece
900 Light Diffusing device
902 Light Emitting Section
902a Distal End (Light Emitting Section)
902b Proximal End (Light Emitting Section)
904 Removed Core Fiber Section
905 Proximal End
906 Distal End
908 Cladding
910 Core Fiber
912 Connector
914 End Piece
1000 Light Diffusing Device
1002 Light Emitting Section
1002a Distal End (Light Emitting Section)
1002b Proximal End (Light Emitting Section)
1004 Removed Core Fiber Section
1005 Proximal End
1006 Distal End
1008 Cladding
1010 Core Fiber
1012 Connector
1014 End Piece
1100 Light Diffusing Device
1102 Light Emitting Section
1102a Distal End (Light Emitting Section)
1102b Proximal End (Light Emitting Section)
1104a Rougher Section of Core Fiber
1104b Smoother Section of Core Fiber
1105 Proximal End
1106 Distal End
1108 Cladding
1110 Core Fiber
1112 Connector
1114 End Piece
1200 Light Diffusing device
1202 Light Emitting Section
1202a Distal End (Light Emitting Section)
1202b Proximal End (Light Emitting Section)
1204 Light Port
1205 Proximal End
1206 Distal End
1208 Cladding
1210 Core Fiber
1212 Connector
1214 Piercing Tip
1300 Light Diffusing device
1302 Light Emitting Section
1302a Distal End (Light Emitting Section)
1302b Proximal End (Light Emitting Section)
1304 Light Port
1305 Proximal End
1306 Distal End
1308 Cladding
1310 Core Fiber
1312 Connector
1314 Piercing Tip
1316 Fluorescent Material
1400 Light Diffusing device
1402 Light Emitting Section
1402a Distal End (Light Emitting Section)
1402b Proximal End (Light Emitting Section)
1404 Light Port
1405 Proximal End
1406 Distal End
1408 Cladding
1410 Core Fiber
1412 Connector
1414 Piercing Tip
1418 Sheathing
1500 Light Diffusing device
1502 Light Emitting Section
1502a Distal End (Light Emitting Section)

1502b Proximal End (Light Emitting Section)
1504 Light Port
1505 Proximal End
1506 Distal End
1508 Cladding
1510 Core Fiber
1512 Connector
1514 Piercing Tip
1516 Fluorescent Material
1518 Sheathing
1600 Light Diffusing device
1602 Light Emitting Section
1602a Distal End (Light Emitting Section)
1602b Proximal End (Light Emitting Section)
1604 Light Port
1605 Proximal End
1606 Distal End
1608 Cladding
1610 Core Fiber
1612 Connector
1614 Piercing Distal End
1616 Fluorescent Material
1618 Sheathing
1700 Light Diffusing Device
1702 Light Emitting Section
1702a Distal End (Light Emitting Section)
1702b Proximal End (Light Emitting Section)
1704a Rougher Section of Light Emitting Section
1704b Smoother Section of Light Emitting Section
1705 Proximal End
1706 Distal End
1708 Cladding
1710 Core Fiber
1712 Connector
1714 End Piece

DEFINITIONS

"Distal" means further from the point controlled by the operator (e.g., physician or technician) of a device.

"Opaque" means absorbing light energy in a particular wavelength range.

"Proximal" means closer to the point controlled by the operator (e.g., physician or technician) of a device.

Construction

Figure 1A:
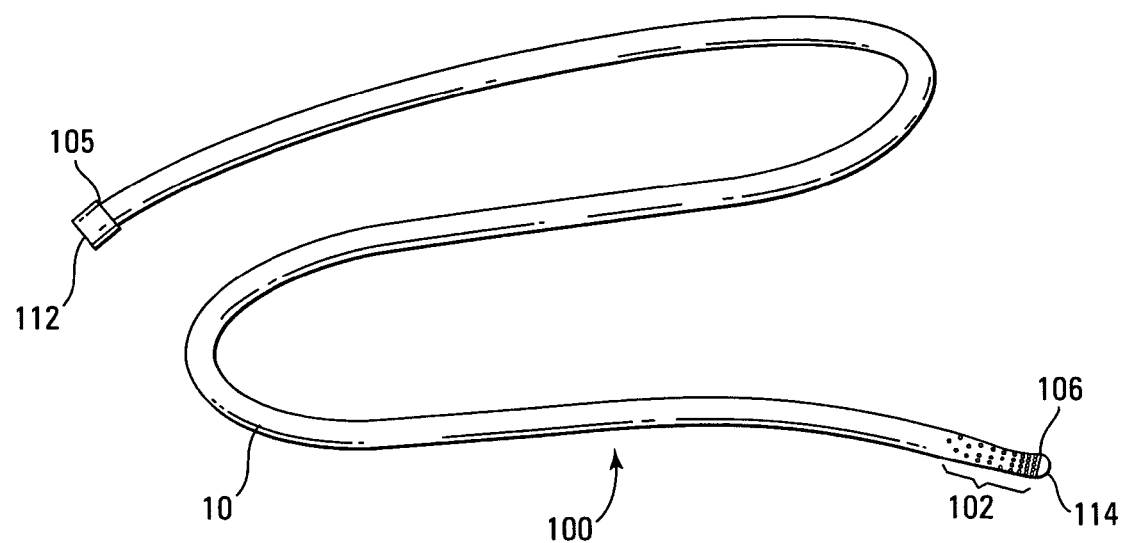
FIG. 1A is a plan view of the light diffusing device shown in FIG. 1.
Figure 1B:
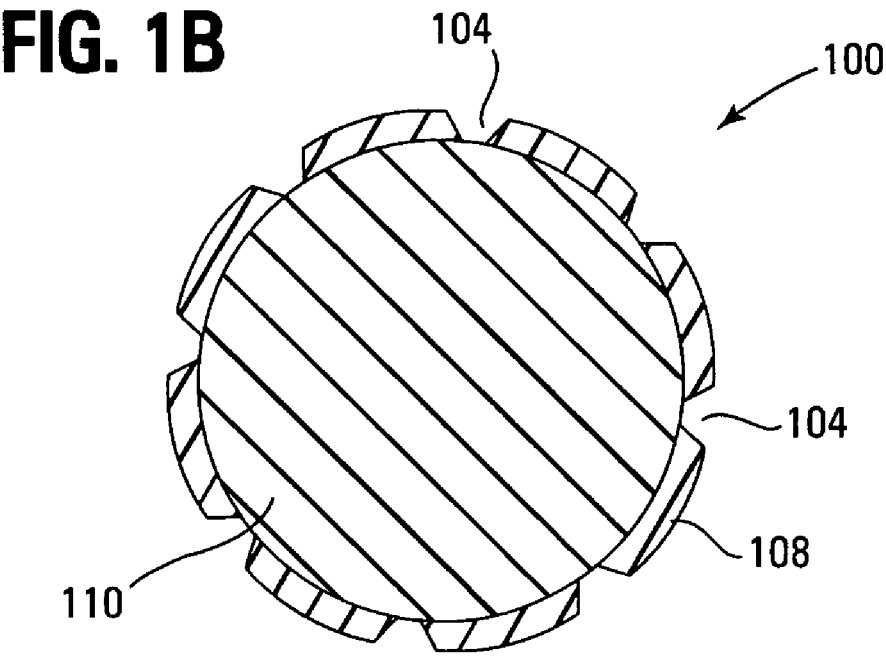
FIG. 1B is a lateral cross section taken through the lines 1B-1B as shown in FIG. 1.

FIG. 1 shows the light emitting section 102 of an embodiment of a light diffusing device 100 of the present invention. FIG. 1A shows the entire light diffusing device 100, including a connector 112 attached to the proximal end 105 allowing the light diffusing device 100 to be connected to a light source (not shown). As best shown in FIG. 1B the light diffusing device 100 is made for reasons of economy as well as flexibility from a plastic optical fiber 10 approximately 1 mm in diameter which comprises a light transmitting core fiber 110 made of PMMA (acrylic) surrounded by cladding 108 made of fluorinated polymers. It should be mentioned that other kinds of light transmitting fibers (not shown) could also be used and are therefore contemplated by and within the scope of the invention. The core fiber 110 and cladding 108 have different indexes of refraction, which enables light entering the light diffusing device 100 at the connector 112 to be transmitted along the length of the light diffusing device 100 and therefore transmitted to a more distal location. The light diffusing device 100 defines a distal end 106 to which is attached an opaque end piece 114, preventing the escape of the transmitted light energy from an otherwise open distal end (not shown) of the core fiber 110. In one embodiment, the end piece 114 can be made of stainless steel. Using appropriate medical grade adhesives, the end piece 114 is attached to the distal end 106 of the optical fiber 10 after the distal end 106 is roughened by such means as sandpaper, sandblasting, chemical degradation or other abrasive or erosive methods. In another embodiment (not shown) the end piece 114 may be omitted and replaced by other light blocking mechanisms including opaque epoxy or plastic materials. In an alternative embodiment (not shown) the light diffusing device 100 may be encased in a transparent protective sheath (not shown) which provides an additional degree of integrity as well as smoothness.

The light emitting section 102 is defined by a plurality of light ports 104 which extend through the cladding 108 exposing the core fiber 110, thereby allowing the transmitted light energy to be emitted from the light diffusing device 100. As best shown in FIG. 1, the light emitting section 102 is characterized by the light ports 104 having a similar surface area and progressively denser in distribution (greater in number) as the distal end 102a is reached. As shown in FIG. 1B the light ports 104 are round shaped and spacing may vary between 0.022 inches to 0.040 inches. Restated, a denser distribution of similarly sized light ports 104 at the distal end 102a results in a lesser exposed core fiber 110 surface area at the proximal end 102b of the light emitting section 102 and a greater exposed core fiber 110 surface area at the distal end 102a of the light emitting section 102, allowing a greater quantity of light to be available at the distal end 102a of the light emitting section 102. The reason for this is that if the distribution of light ports 104 was even (not shown), more light would be emitted from the more proximally located light ports 104, leaving less light available to be emitted from the more distally located light ports 104. The result of evenly distributed light ports 104 (not shown) would be a device (not shown) having uneven light distribution, with more intensity toward the proximal end and less toward the distal end. The embodiment of the light diffusing device 100 shown in FIGS. 1-1B thus evenly emits the transmitted light energy along the length of the light emitting section 102, allowing safer and more precise photodynamic therapy.

Figure 2B:
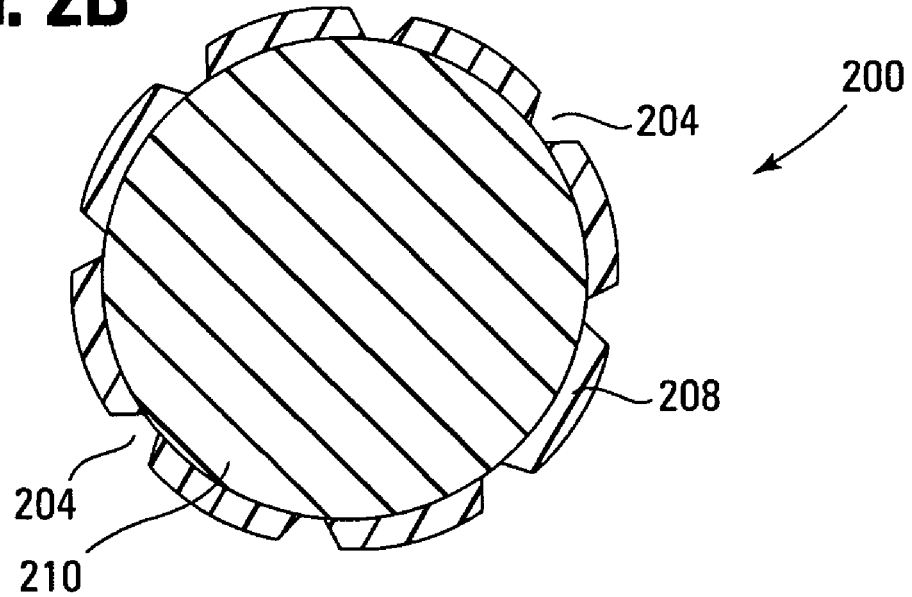
FIG. 2B is a lateral cross section taken through the lines 2B-2B as shown in FIG. 2.
Figure 2:
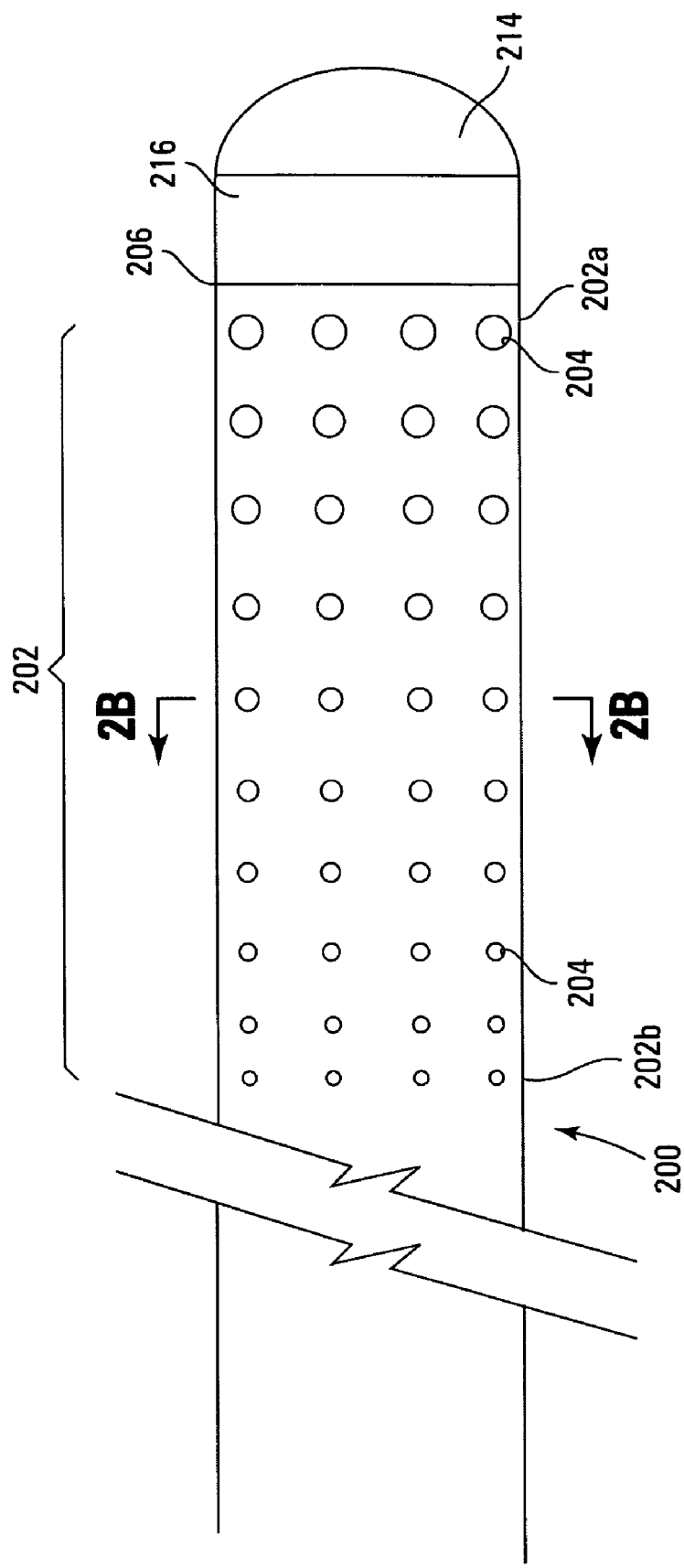
FIG. 2 shows the distal end of an embodiment of the light diffusing device of the present invention having a plurality of open areas through the cladding distally increasing in size.
Figure 2A:
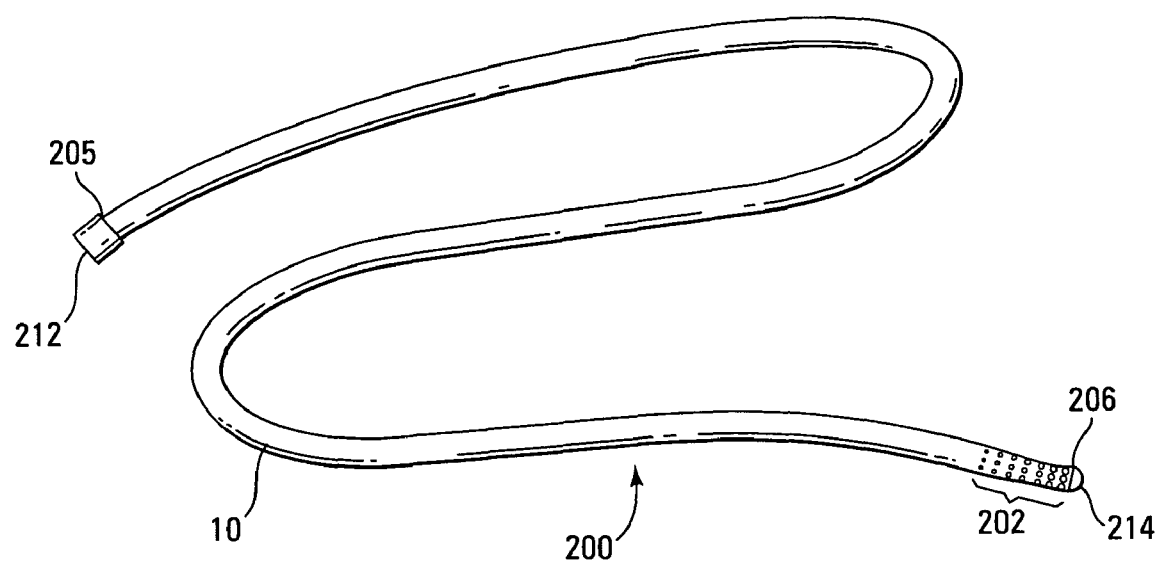
FIG. 2A is a plan view of the light diffusing device shown in FIG. 2.

FIG. 2 shows the light emitting section 202 of an embodiment of a light diffusing device 200 of the present invention. FIG. 2A shows the entire light diffusing device 200, including a connector 212 attached to the proximal end 205 allowing the light diffusing device 200 to be connected to a light source (not shown). As best shown in FIG. 2B the light diffusing device 200 is made for reasons of economy as well as flexibility from a plastic optical fiber 10 approximately 1 mm in diameter which comprises a light transmitting core fiber 210 made of PMMA (acrylic) surrounded by cladding 208 made of fluorinated polymers. It should be mentioned that other kinds of light transmitting fibers (not shown) could also be used and are therefore contemplated by and within the scope of the invention. The core fiber 210 and cladding 208 have different indexes of refraction, which enables light entering the light diffusing device 200 at a proximal location to be transmitted along the length of the light diffusing device 200 and thereby transmitted to a more distal location. The light diffusing device 200 defines a distal end 206 which comprises an opaque end piece 214, preventing the escape of the transmitted light energy from the core fiber 210. In one embodiment the end piece 214 is made of stainless steel. In this embodiment a section of fluorescent material 216 is placed between the end piece 214 and the distal end 206 of the optical fiber 10. The fluorescent material 216 can be made of chromium crystal, however, this is not intended to be limiting as other materials including alexandrite, sapphire and others would also work. Using appropriate medical grade adhesives, the fluorescent material 216 is attached to the distal end 206 of the optical fiber 10 after the distal end 206 is roughened by such means as sandpaper, sandblasting, chemical degradation or other abrasive or erosive methods. Following attachment of the fluorescent material 216 to the optical fiber 10, the opaque end piece 214 is attached to the distal end (unnumbered) of the fluorescent material 216 using appropriate medical grade adhesives. The end piece 214 prevents the escape of light energy through the distal end 206. The fluorescent material 216 emits a signal when illuminated by light energy having a wavelength at least at an excitation wavelength and above and thus functions as a fluorescence feedback indicator. In this configuration, when the laser light source (not shown) is energized, fluorescence occurs at the distal end 206 and is detected at the light source console (not shown) to verify the light diffusing device 200 is valid and functioning properly. In another embodiment (not shown) the end piece 214 may be omitted and replaced by other light blocking mechanisms including opaque epoxy or plastic materials. In an alternative embodiment (not shown) the light diffusing device 200 may be encased in a transparent protective sheath (not shown) which provides an additional degree of integrity as well as smoothness.

The light emitting section 202 is defined by a plurality of light ports 204 which extend through the cladding 208 exposing the core fiber 210 allowing the transmitted light energy to be emitted from the light diffusing device 200. As best shown in FIG. 2, the light emitting section 202 is characterized by the light ports 204 progressively defining a greater surface area as the distal end 206 is reached. The light ports 204 are conically shaped and spacing may vary in diameter between 0.003 inches to 0.006 inches. Restated, progressively greater sized light ports 204 toward the distal end 202*a* result in a lesser exposed core fiber 210 surface area at the proximal end 202*b* of the light emitting section 202 and a greater exposed core fiber 210 surface area at the distal end 202*a* of the light emitting section 202, allowing a greater quantity of light to be available at the distal end 206 of the light emitting section 202. The reason for this is that if the surface area of the light ports 204 was consistent (not shown), more light would be emitted from the more proximally located light ports 204, leaving less light available to be emitted from the more distally located light ports 204. The result of similarly sized light ports 204 (not shown) would be a device (not shown) having uneven light distribution, with more intensity toward the proximal end and less toward the distal end. The embodiment of the light diffusing device 200 shown in FIGS. 2-2B thus evenly emits the transmitted light energy along the length of the light emitting section 202, allowing safer and more precise photodynamic therapy.

Figure 3:
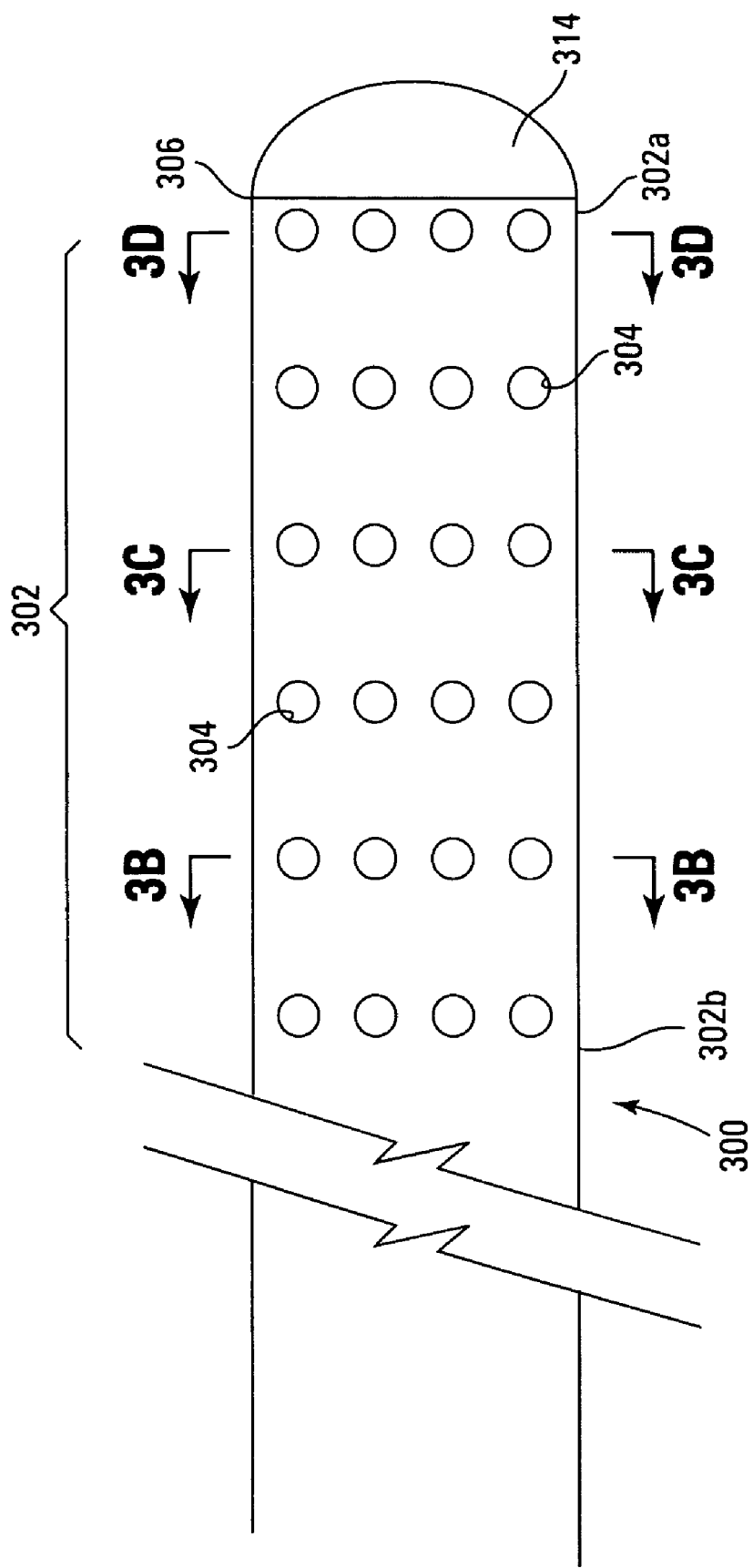
FIG. 3 shows the distal end of an embodiment of the light diffusing device of the present invention having a plurality of similarly sized open areas through the cladding distally increasing in depth into the core fiber.
Figure 3A:
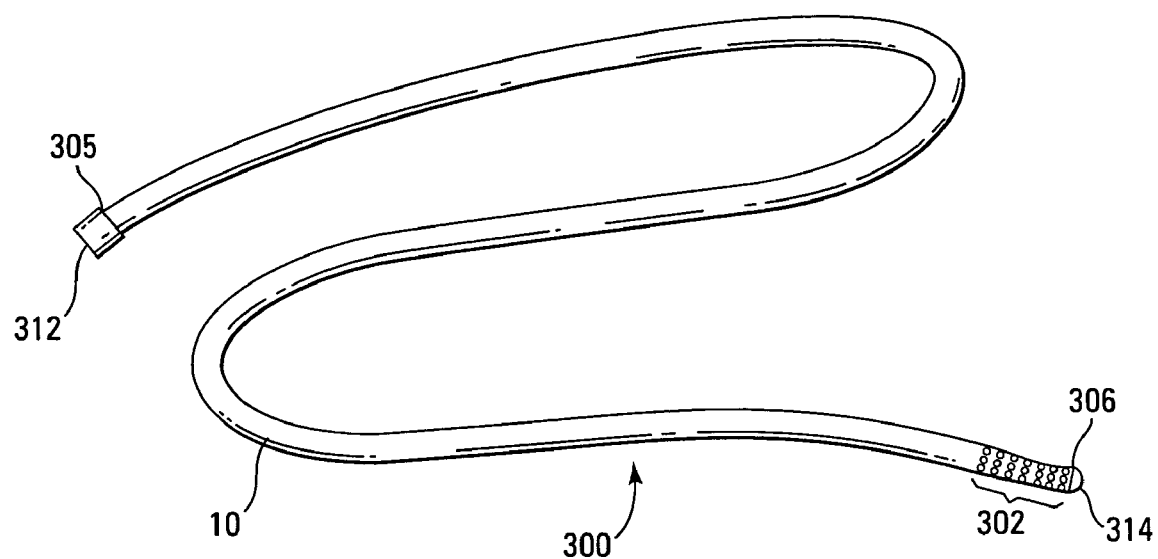
FIG. 3A is a plan view of the light diffusing device shown in FIG. 3.
Figure 3B:
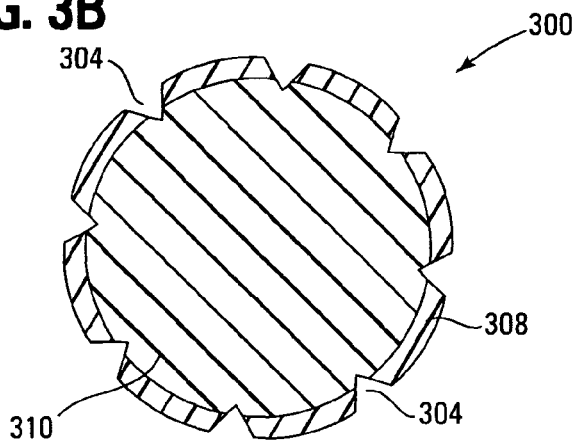
FIG. 3B is a lateral cross section taken through the lines 3B-3B as shown in FIG. 3, showing openings through the cladding and into the core fiber having a relatively shallow depth.
Figure 3C:
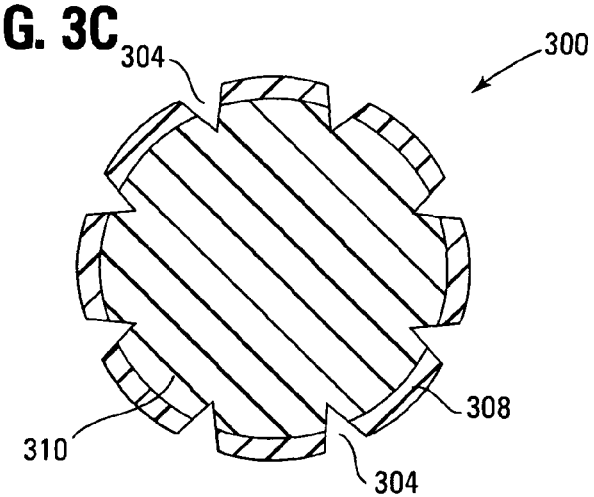
FIG. 3C is a lateral cross section taken through the lines 3C-3C as shown in FIG. 3, showing openings through the cladding and into the core fiber having a relatively intermediate depth.
Figure 3D:
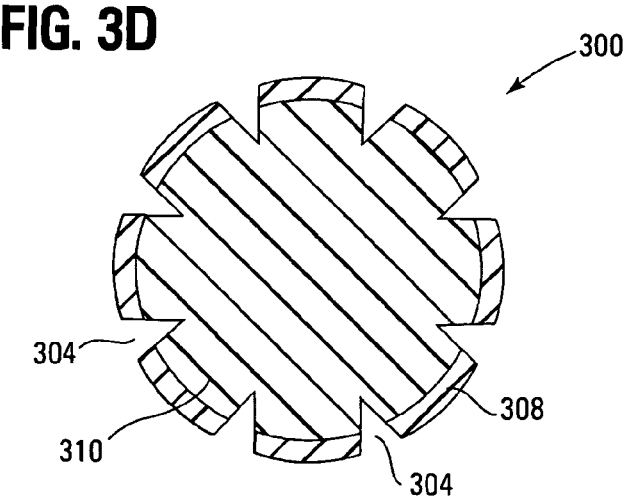
FIG. 3D is a lateral cross section taken through the lines 3D-3D as shown in FIG. 3, showing openings through the cladding and into the core fiber having a relatively deep depth.

FIG. 3 shows the light emitting section 302 of an embodiment of a light diffusing device 300 of the present invention. FIG. 3A shows the entire light diffusing device 300, including a connector 312 attached to the proximal end 305 allowing the light diffusing device 300 to be connected to a light source (not shown). As best shown in FIGS. 3B, 3C, 3D the light diffusing device 300 is made for reasons of economy as well as flexibility from a plastic optical fiber 10 approximately 1 mm in diameter which comprises a light transmitting core fiber 310 made of PMMA (acrylic) surrounded by cladding 308 made of fluorinated polymers. It should be mentioned that other kinds of light transmitting fibers (not shown) could also be used and are therefore contemplated by and within the scope of the invention. The core fiber 310 and cladding 308 have different indexes of refraction, which enables light entering the light diffusing device 300 at the connector 312 to be transmitted along the length of the light diffusing device 300 and thereby transmitted to a more distal location. The light diffusing device 300 defines a distal end 306 to which is attached an opaque end piece 314, preventing the escape of the transmitted light energy from an open distal end (not shown) of the core fiber 310. The end piece 314 can be made of stainless steel. Using appropriate medical grade adhesives, the end piece 314 is attached to the distal end 306 of the light diffusing device 300 after the distal end 306 of the optical fiber 10 is roughened by such means as sandpaper, sandblasting, chemical degradation or other abrasive or erosive methods. In another embodiment (not shown) the end piece 314 may be omitted and replaced by other light blocking mechanisms including opaque epoxy or plastic materials. In an alternative embodiment (not shown) the light diffusing device 300 may be encased in a transparent protective sheath (not shown) which provides an additional degree of integrity as well as smoothness.

The light emitting section 302 is defined by a plurality of light ports 304 which extend through the cladding 308 into the core fiber 300 allowing the transmitted light to be emitted from the light diffusing device 300. As best shown in FIGS. 3B, 3C, 3D, the light emitting section 302 is characterized by the light ports 304 having a similar surface area and progressively deeper into the core fiber 310 as the distal end 302*a* is reached, thus exposing a greater amount of core fiber 310. The light ports 304 are conically shaped and the depth may vary between 0.004 inches to 0.008 inches. Restated, progressively deeper, similarly sized light ports 304 toward the distal end 302*a* result in a lesser exposed core fiber 310 surface area at the proximal end 302*b* of the light emitting section 302 and a greater exposed core fiber 310 surface area at the distal end 302*a* of the light emitting section 302, allowing a greater quantity of light to be available at the distal end 302*a* of the light emitting section 302. The reason for this is that if the size and depth of light ports 304 was consistent (not shown), more light would be emitted from the more proximally located light ports 304, leaving less light available to be emitted from the more distally located light ports 304. The result of similarly sized and depth light ports 304 (not shown) would be a device (not shown) having uneven light distribution, with more intensity toward the proximal end and less toward the distal end. The embodiment of the light diffusing device 300 shown in FIG. 3 thus evenly emits the transmitted light energy along the length of the light emitting section 302, allowing safer and more precise photodynamic therapy.

Figure 4A:
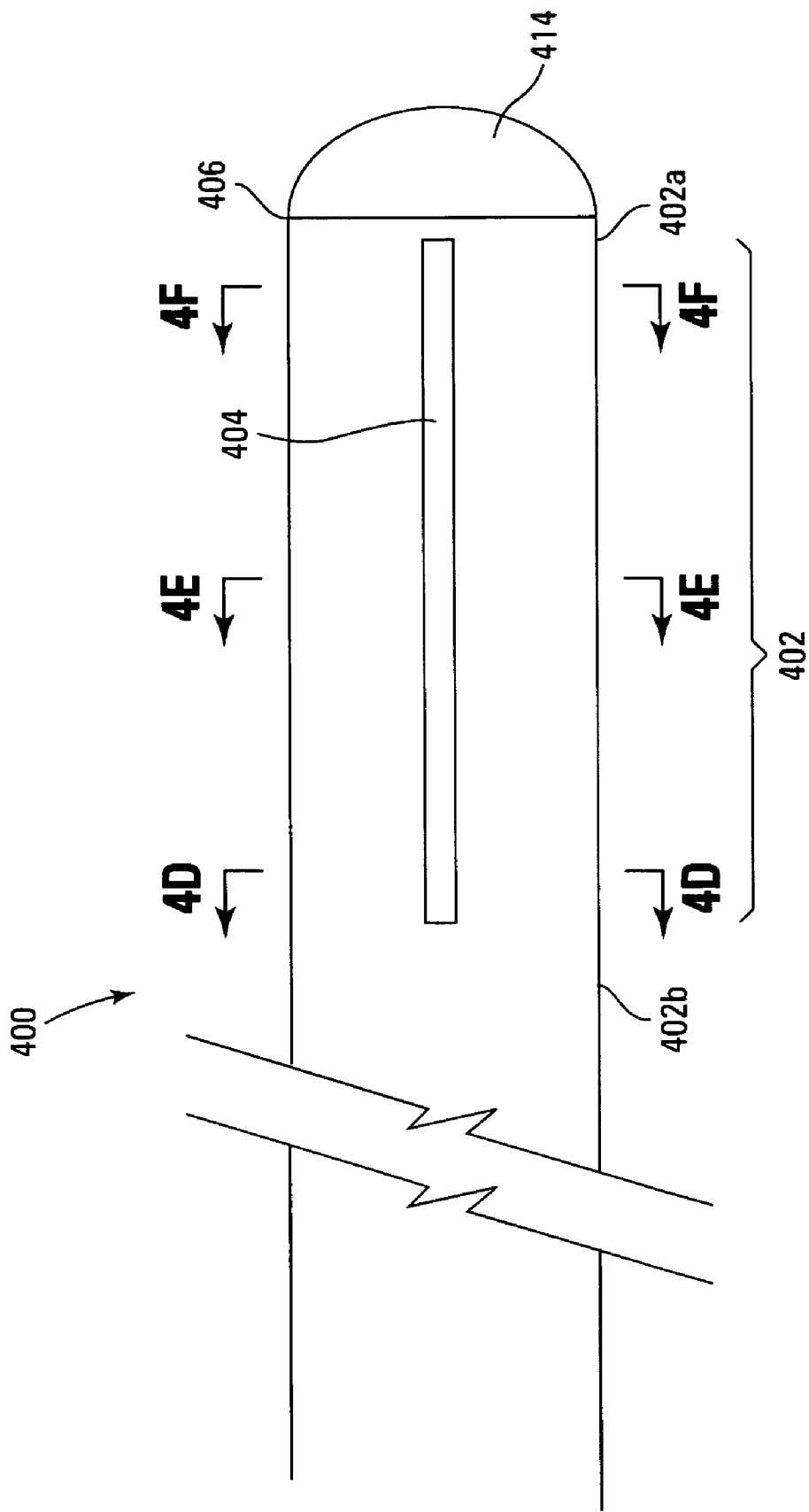
FIG. 4A is a top view of the distal end of a light diffusing device of the present invention having a continuous opening through the cladding and extending progressively distally deeper into the core fiber.
Figure 4B:
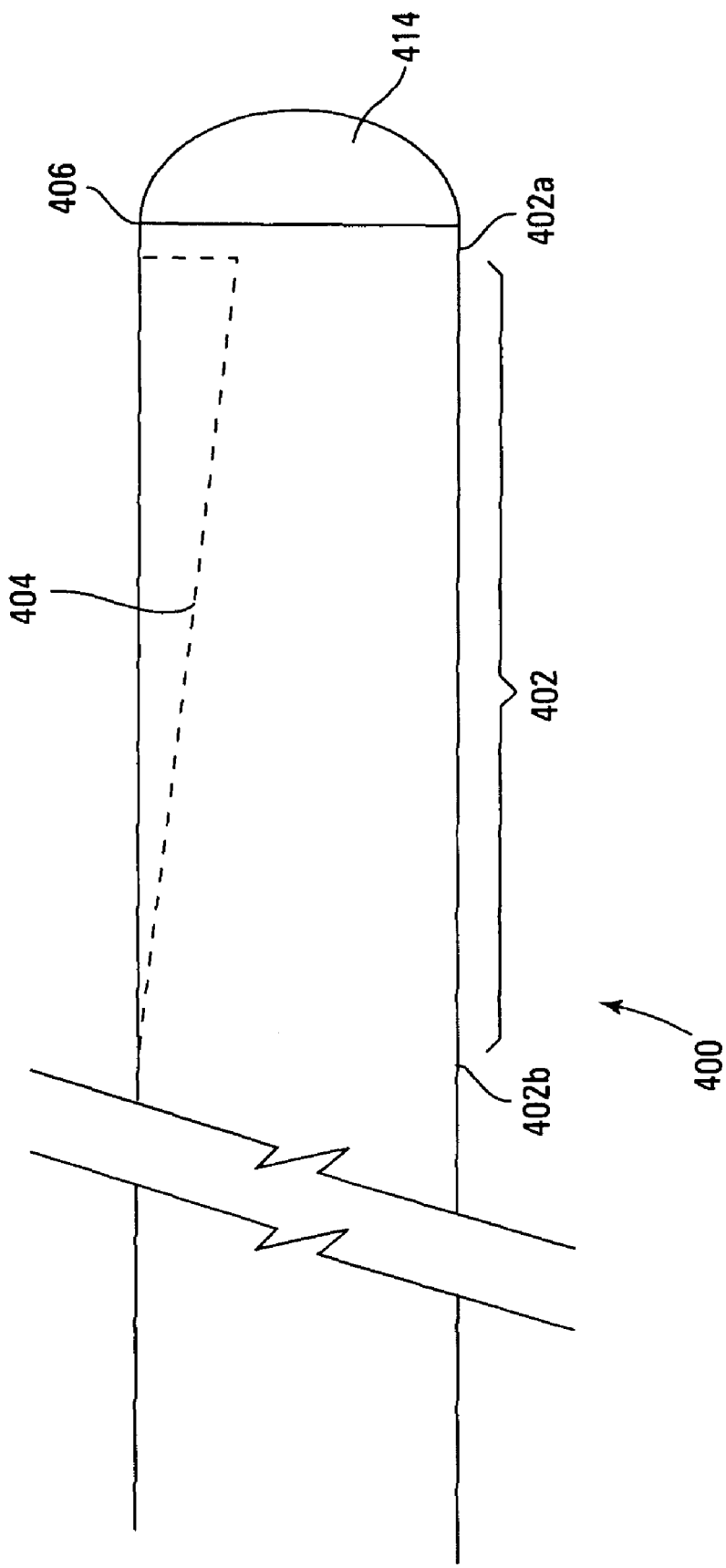
FIG. 4B is a side view of the distal end of the light diffusing device shown in FIG. 4A using phantom lines to show the continuous opening extending progressively distally deeper into the core fiber.
Figure 4C:
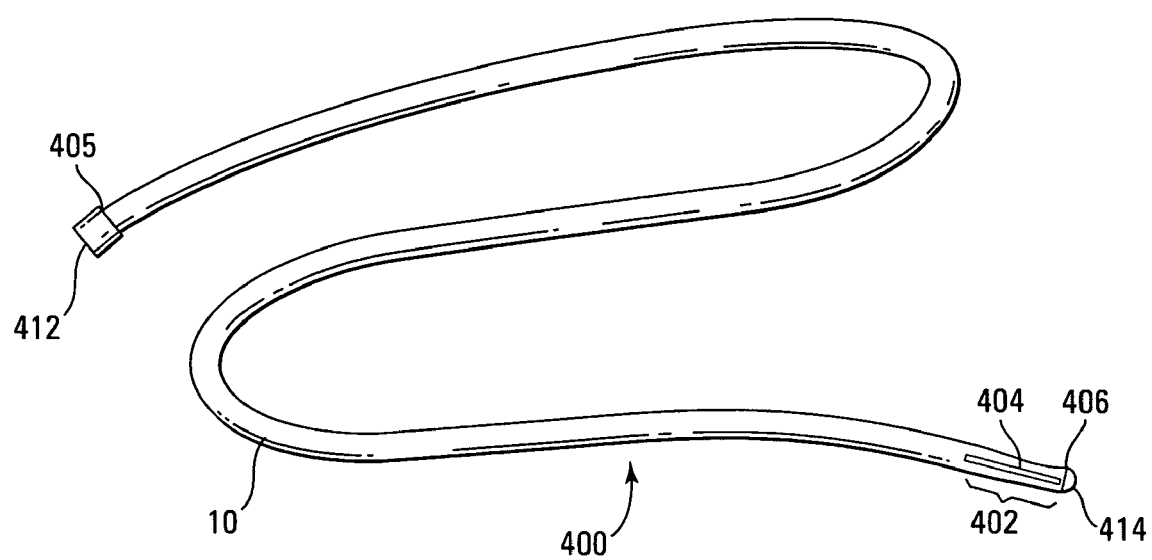
FIG. 4C is a plan view of the light diffusing device shown in FIG. 4.
Figure 4D:
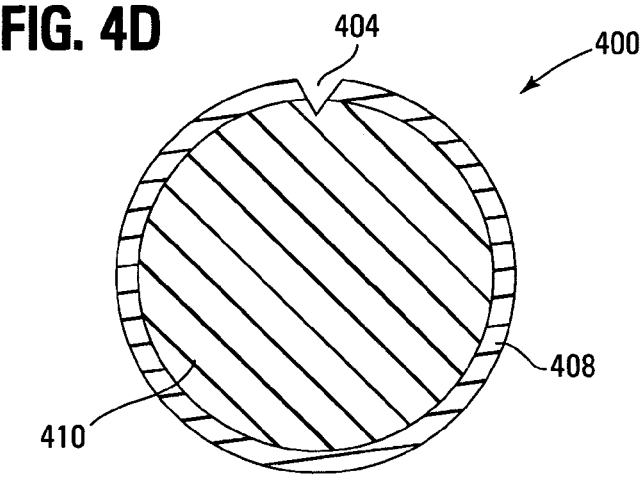
FIG. 4D is a lateral cross section taken through the lines 4D-4D as shown in FIGS. 4A-4B, showing the opening through the cladding and into the core fiber having a relatively shallow depth.
Figure 4E:
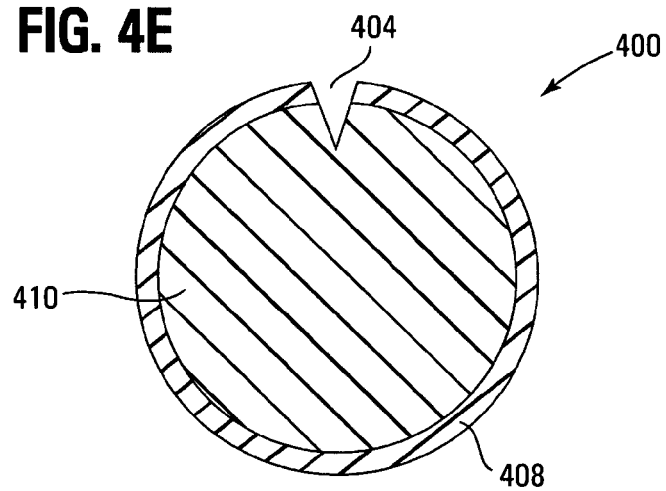
FIG. 4E is a lateral cross section taken through the lines 4E-4E as shown in FIGS. 4A-4B, showing the opening through the cladding and into the core fiber having a relatively intermediate depth.
Figure 4F:
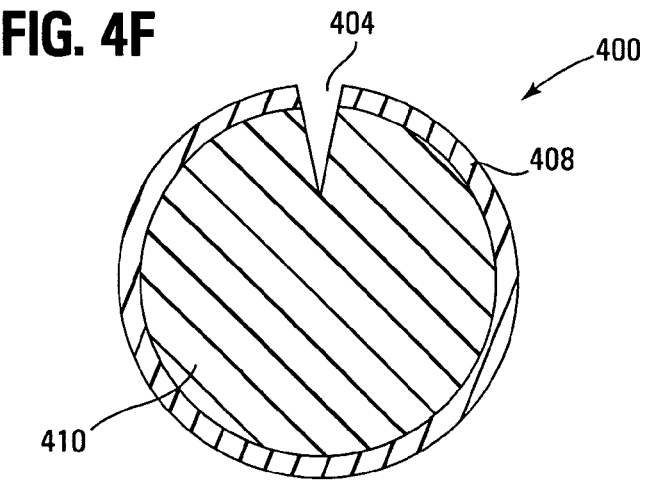
FIG. 4F is a lateral cross section taken through the lines 4F-4F as shown in FIGS. 4A-4B, showing the opening through the cladding and into the core fiber having a relatively deep depth.

FIG. 4A shows a top view of the light emitting section 402 of an embodiment of the light diffusing device 400 of the present invention. A side view is shown in FIG. 4B, with phantom lines indicating the location and depth of the light port 404. FIG. 4C shows the entire light diffusing device 400, including a connector 412 attached to the proximal end 405 allowing the light diffusing device 400 to be connected to a light source (not shown). As best shown in FIGS. 4D, 4E, 4F the light diffusing device 400 is made for reasons of economy as well as flexibility from a plastic optical fiber 10 approximately 1 mm in diameter which comprises a light transmitting core fiber 410 made of PMMA (acrylic) surrounded by cladding 408 made of fluorinated polymers. It should be mentioned that other kinds of light transmitting fibers (not shown) could also be used and are therefore contemplated by and within the scope of the invention. The core fiber 410 and cladding 408 have different indexes of refraction, which enables light entering the light diffusing device 400 at the connector 412 to be transmitted along the length of the light diffusing device 400 and thereby transmitted to a more distal location. The light diffusing device 400 defines a distal end 406 which comprises an opaque end piece 414, preventing the escape of the transmitted light energy from an otherwise open distal end (not shown) of the core fiber 410. In one embodiment, the end piece 414 is made of stainless steel. Using appropriate medical grade adhesives, the end piece 414 is attached to the distal end 406 of the optical fiber 10 after the distal end 406 is roughened by such means as sandpaper, sandblasting, chemical degradation or other abrasive methods. In another embodiment (not shown) the end piece 414 may be omitted and replaced by other light blocking mechanisms including opaque epoxy or plastic materials. In an alternative embodiment (not shown) the light diffusing device 400 may be encased in a transparent protective sheath (not shown) which provides an additional degree of integrity as well as smoothness.

The light emitting section 402 is defined by an extended light port 404 which is cut through the cladding 408 into the core fiber 400 allowing the transmitted light to be emitted from the light diffusing device 400. While a single extended light port 404 is shown in FIGS. 4-4F, this is for purposes of illustration only and the invention could also include multiple extended light ports 404 (not shown). As best shown in FIGS. 4D, 4E, 4F, the light emitting section 402 is characterized by the light port 404 extending progressively deeper into the core fiber 410 as the distal end 402a is reached. Restated, the progressively deeper light port 404 toward the distal end 402a results in a lesser exposed core fiber 410 surface area at the proximal end 402b of the light emitting section 402 and a greater exposed core fiber 410 surface area at the distal end 402a of the light emitting section 402, allowing a greater quantity of light to be available at the distal end (unnumbered) of the light emitting section 402. The reason for this is that if the depth of the light port 404 was consistent (not shown), more light would be emitted from the proximal end of the light port 404, leaving less light available to be emitted from the distal end of the light port 404. The result of a uniform depth light port 404 (not shown) would be an optical fiber (not shown) having uneven light distribution, with more intensity toward the proximal end and less toward the distal end. The embodiment of the light diffusing device 400 shown in FIG. 4 thus evenly emits the transmitted light energy along the length of the light emitting section 402, allowing safer and more precise photodynamic therapy.

Figure 5:
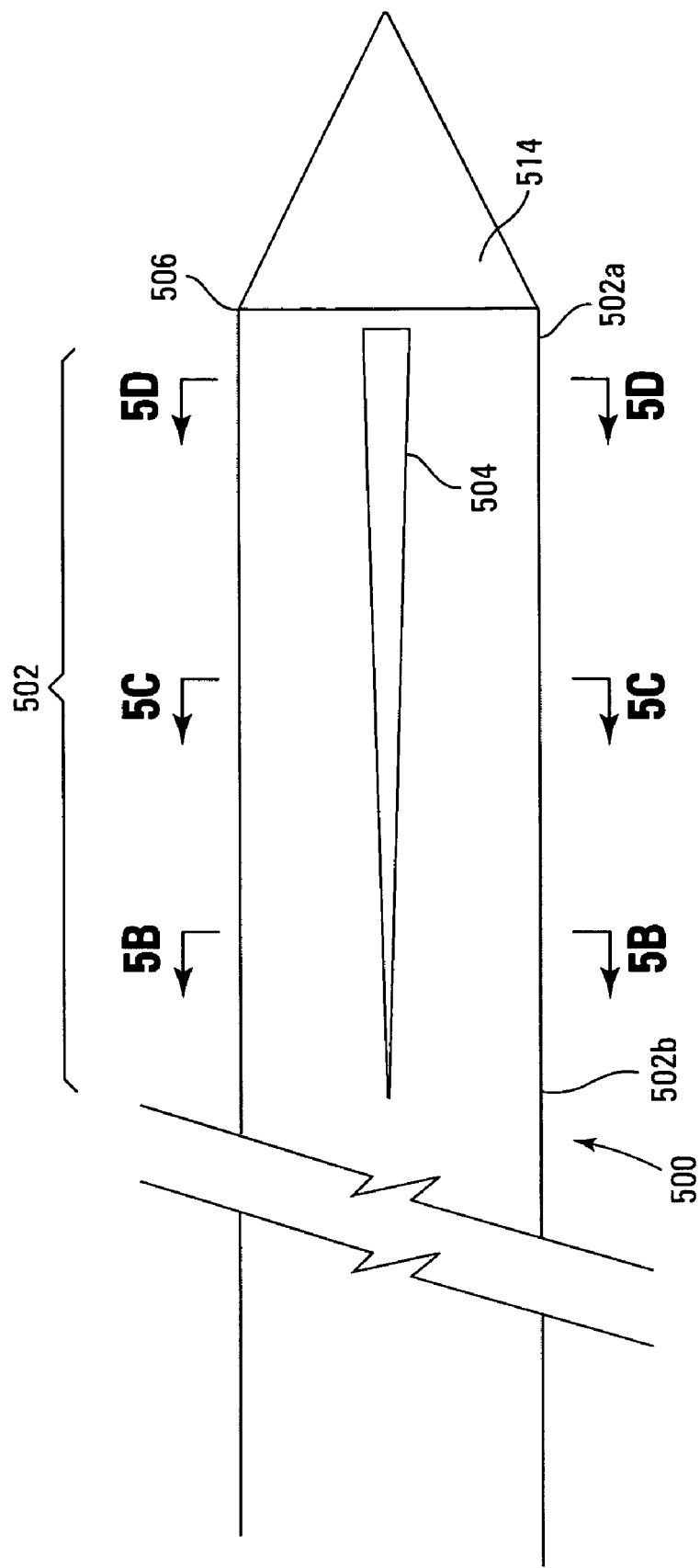
FIG. 5 shows the distal end of a light diffusing device of the present invention having a continuous opening extending distally wider through the cladding.
Figure 5A:
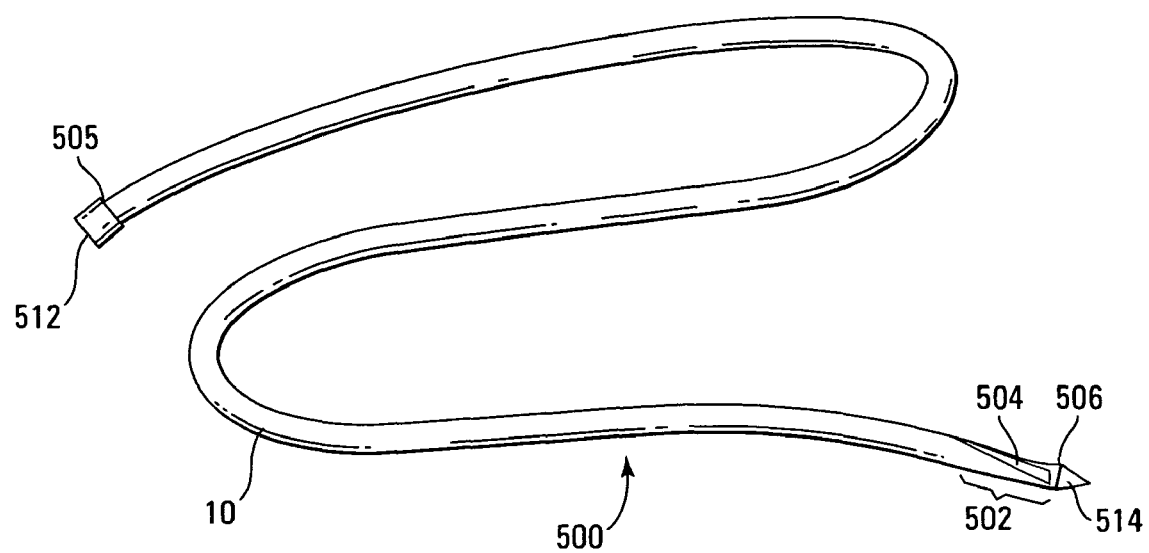
FIG. 5A is a plan view of the light diffusing device shown in FIG. 5.
Figure 5B:
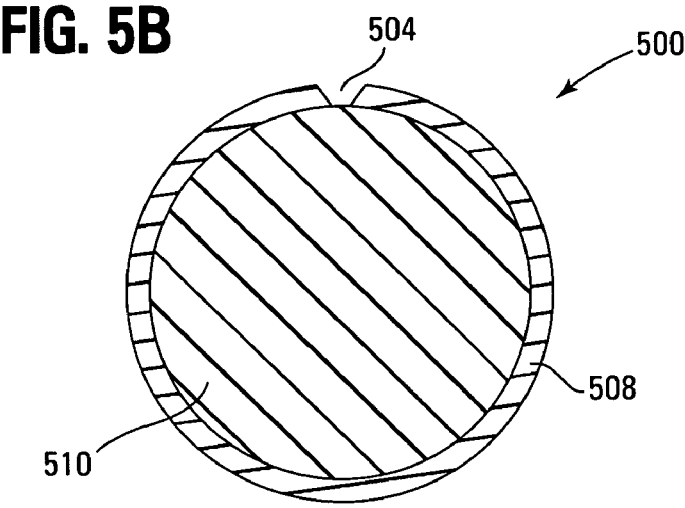
FIG. 5B is a lateral cross section taken through the lines 5B-5B as shown in FIG. 5, showing the opening through the cladding and into the core fiber having a relatively narrow width.
Figure 5C:
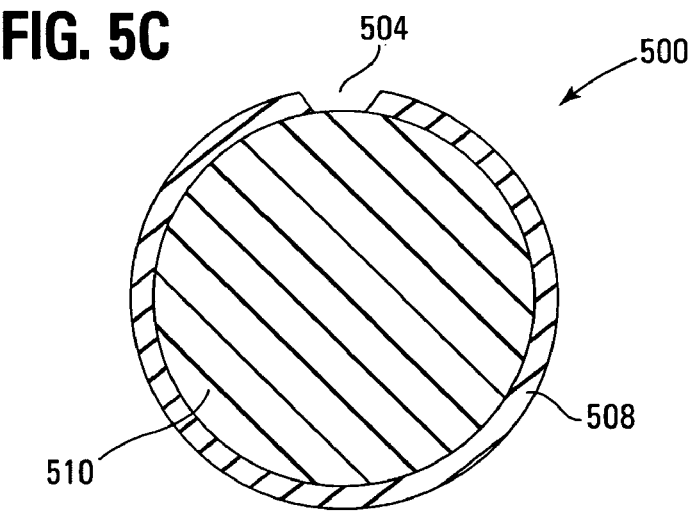
FIG. 5C is a lateral cross section taken through the lines 5C-5C as shown in FIG. 5, showing the opening through the cladding and into the core fiber having a relatively intermediate width.
Figure 5D:
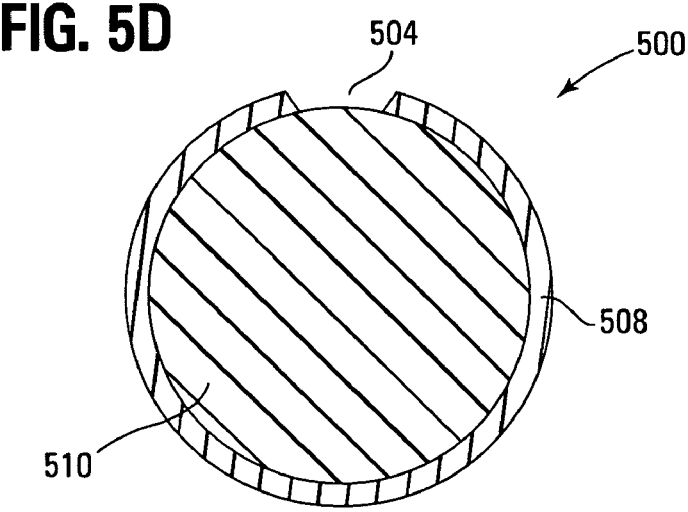
FIG. 5D is a lateral cross section taken through the lines 5D-5D as shown in FIG. 5, showing the opening through the cladding and into the core fiber having a relatively wide width.

FIG. 5 shows the light emitting section 502 of an embodiment of the light diffusing device 500 of the present invention. FIG. 5A shows the entire light diffusing device 500, including a connector 512 attached to the proximal end 505 allowing the light diffusing device 500 to be connected to a light source (not shown). As best shown in FIGS. 5B, 5C, 5D the light diffusing device 500 is made for reasons of economy as well as flexibility from a plastic optical fiber 10 approximately 1 mm in diameter which comprises a light transmitting core fiber 510 made of PMMA (acrylic) surrounded by cladding 508 made of fluorinated polymers. It should be mentioned that other kinds of light transmitting fibers (not shown) could also be used and are therefore contemplated by and within the scope of the invention. The core fiber 510 and cladding 508 have different indexes of refraction, which enables light entering the light diffusing device 500 at the connector 512 to be transmitted along the length of the light diffusing device 500 and thereby transmitted to a more distal location. The light diffusing device 500 defines a distal end 506 to which is attached an opaque end piece 514, preventing the escape of the transmitted light energy from an open distal end (not shown) of the core fiber 510. In one embodiment, the end piece 514 is made of stainless steel. Using appropriate medical grade adhesives, the end piece 514 is attached to the distal end 506 of the optical fiber 10 after the distal end 506 is roughened by such means as sandpaper, sandblasting, chemical degradation or other abrasive or erosive methods. In another embodiment (not shown) the end piece 514 may be omitted and replaced by other light blocking mechanisms including opaque epoxy or plastic materials. In an alternative embodiment (not shown) the light diffusing device 500 may be encased in a transparent protective sheath (not shown) which provides an additional degree of integrity as well as smoothness.

The light emitting section 502 is defined by an extended light port 504 which is cut through the cladding 508 exposing the core fiber 500 allowing the transmitted light to be emitted from the light diffusing device 500. While a single extended light port 504 is shown in FIGS. 5-5D, this is for purposes of illustration only and the invention could also include multiple extended light ports 504 (not shown). As best shown in FIGS. 5B, 5C, 5D, the light emitting section 502 is characterized by the light port 504 extending progressively wider through the cladding 508 as the distal end is reached. Restated, the progressively wider light port 504 toward the distal end results in a lesser exposed core fiber 510 surface area at the proximal end 502b of the light emitting section 502 and a greater exposed core fiber 510 surface area at the distal end 502a of the light emitting section 502, allowing a greater quantity of light to be available at the distal end 502a of the light emitting section 502. The reason for this is that if the width of the light port 504 was consistent (not shown), more light would be emitted from the proximal end 502b of the light port 504, leaving less light available to be emitted from the distal end 502a of the light port 504. The result of a uniform width light port 504 (not shown) would be an optical fiber (not shown) having uneven light distribution, with more intensity toward the proximal end and less toward the distal end. The embodiment of the light diffusing device 500 shown in FIG. 5 thus evenly emits the transmitted light energy along the length of the light emitting section 502, allowing safer and more precise photodynamic therapy.

Figure 6:
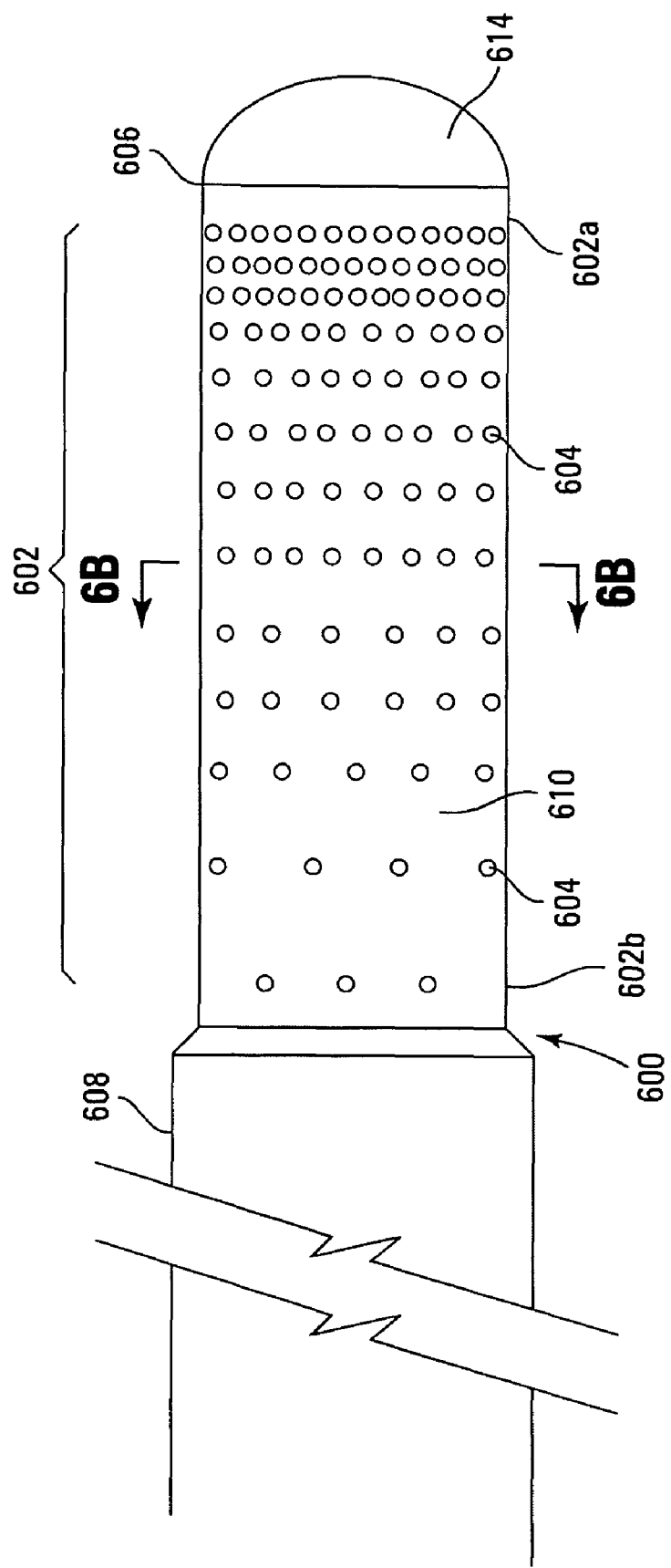
FIG. 6 shows the distal end of an embodiment of the light diffusing device of the present invention having an exposed core fiber at the distal end with a plurality of similarly sized removed core fiber sections distally progressively closer in proximity to each other.
Figure 6A:
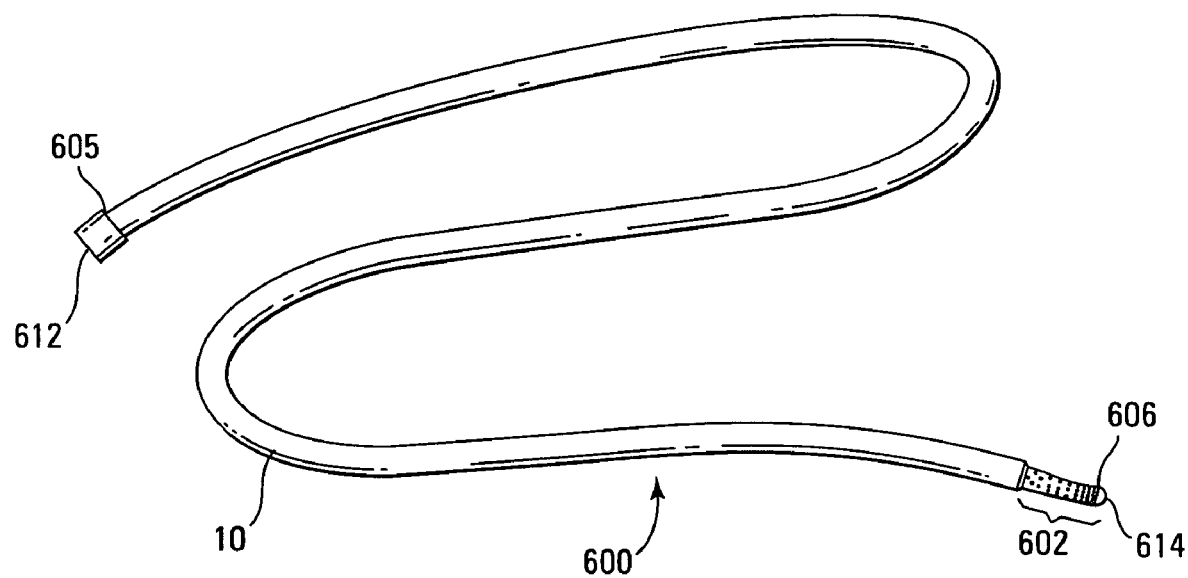
FIG. 6A is a plan view of the light diffusing device shown in FIG. 6.
Figure 6B:
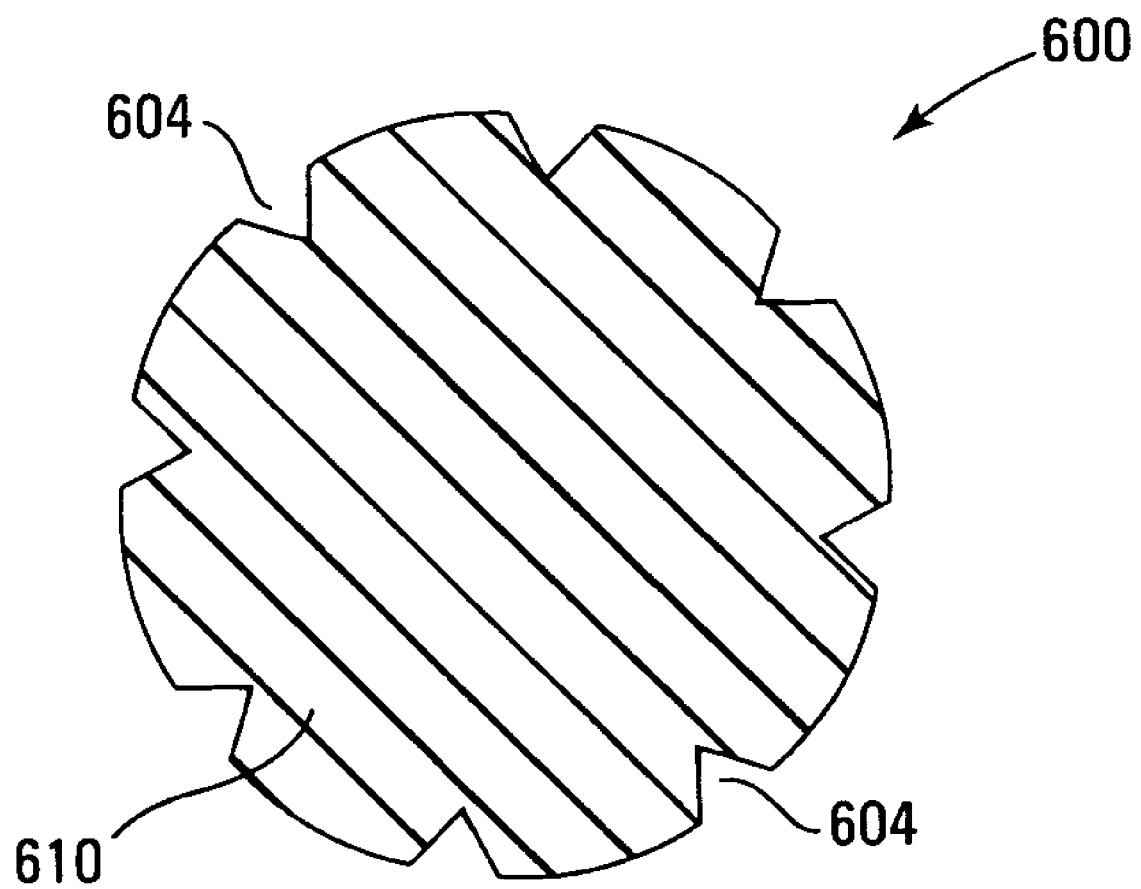
FIG. 6B is a lateral cross section taken through the lines 6B-6B as shown in FIG. 6.

FIG. 6 shows the light emitting section 602 of an embodiment of a light diffusing device 600 of the present invention. FIG. 6A shows the entire light diffusing device 600, including a connector 612 attached to the proximal end 605 allowing the light diffusing device 600 to be connected to a light source (not shown). As best shown in FIG. 6B the light diffusing device 600 is made for reasons of economy as well as flexibility from a plastic optical fiber 10 approximately 1 mm in diameter which comprises a light transmitting core fiber 610 made of PMMA (acrylic) surrounded by cladding 608 made of fluorinated polymers. It should be mentioned that other kinds of light transmitting fibers (not shown) could also be used and are therefore contemplated by and within the scope of the invention. The core fiber 610 and cladding 608 have different indexes of refraction, which enables light entering the light diffusing device 600 at the connector 612 to be transmitted along the length of the light diffusing device 600 and therefore transmitted to a more distal location. The light diffusing device 600 defines a distal end 606 to which is attached an opaque end piece 614, preventing the escape of the transmitted light energy from an open distal end (not shown) of the core fiber 610. In one embodiment, the end piece 614 is made of stainless steel. Using appropriate medical grade adhesives, the end piece 614 is attached to the distal end 606 of the optical fiber 10 after the distal end 606 is roughened by such means as sandpaper, sandblasting, chemical degradation or other abrasive or erosive methods. In another embodiment (not shown) the end piece 614 may be omitted and replaced by other light blocking mechanisms including opaque epoxy or plastic materials. In an alternative embodiment (not shown) the light diffusing device 600 may be encased in a transparent protective sheath (not shown) which provides an additional degree of integrity as well as smoothness.

In this embodiment the light diffusing device 600 has an exposed section of core fiber 610 which defines the light emitting section 602. The light emitting section 602 is further defined by a plurality of removed core fiber sections 604 which extend into the core fiber 610 allowing additional transmitted light energy to be emitted from the light diffusing device 600 as a result of a greater exposed surface area of the core fiber 604. As best shown in FIG. 6, the light emitting section 602 is characterized by the removed core fiber sections 604 having a similar surface area and progressively denser in distribution (greater in number) as the distal end 602a is reached. As shown in FIG. 6B the removed core fiber sections 604 are conical and spacing may vary between 0.022 inches to 0.040 inches. Restated, a denser distribution of similarly sized removed core fiber sections 604 at the distal end 602a results in a lesser exposed core fiber 610 surface area at the proximal end 602b of the light emitting section 602 and a greater exposed core fiber 610 surface area at the distal end 602a of the light emitting section 602, allowing a greater quantity of light to be available at the distal end 602a of the light emitting section 602. The reason for this is that if the distribution of removed core fiber sections 604 was even (not shown), more light would be emitted from the more proximally located removed core fiber sections 604, leaving less light available to be emitted from the more distally located removed core fiber sections 604. The result of evenly distributed removed core fiber sections 604 (not shown) would be an optical fiber (not shown) having uneven light distribution, with more intensity toward the proximal end and less toward the distal end. The embodiment of the light diffusing device 600 shown in FIGS. 6-6B thus evenly emits the transmitted light energy along the length of the light emitting section 602, allowing safer and more precise photodynamic therapy.

Figure 7:
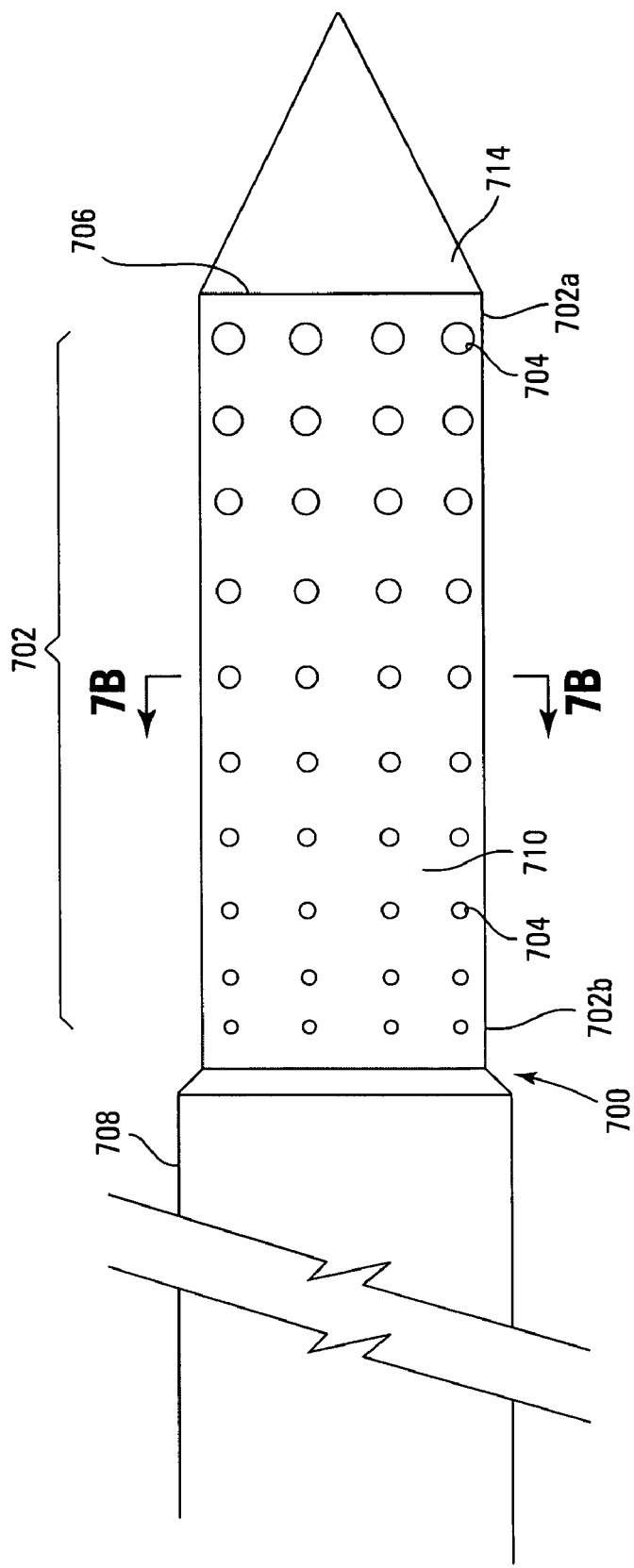
FIG. 7 shows the distal end of an embodiment of the light diffusing device of the present invention having an exposed core fiber at the distal end with a plurality of removed core fiber sections distally increasing in size.
Figure 7A:
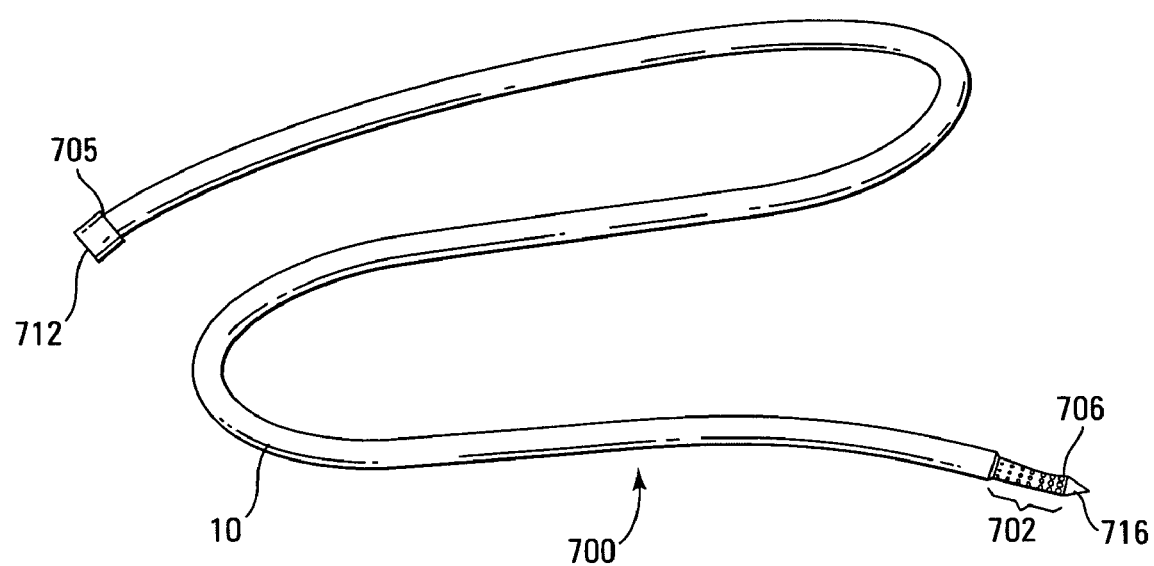
FIG. 7A is a plan view of the light diffusing device shown in FIG. 7.
Figure 7B:
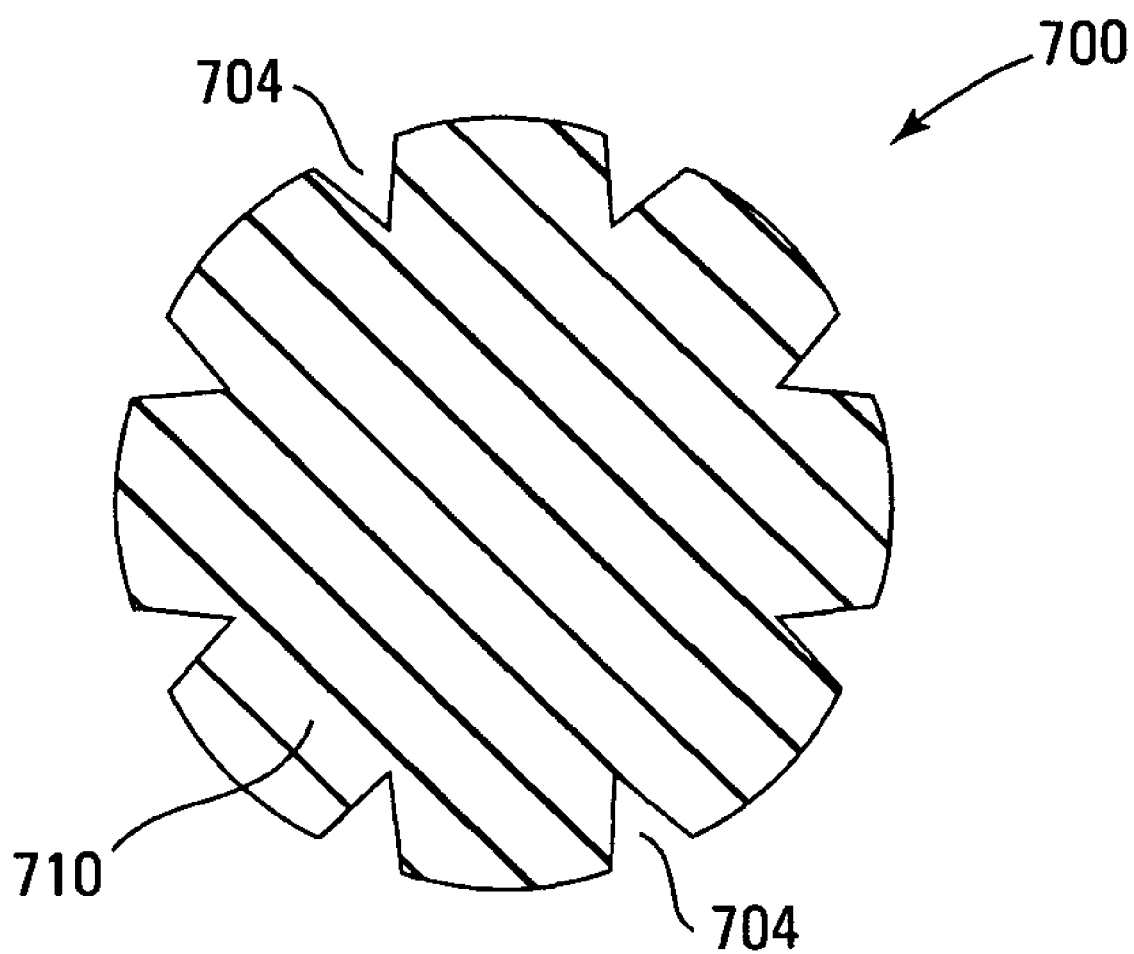
FIG. 7B is a lateral cross section taken through the lines 7B-7B as shown in FIG. 7.

FIG. 7 shows the light emitting section 702 of an embodiment of a light diffusing device 700 of the present invention. FIG. 7A shows the entire light diffusing device 700, including a connector 712 attached to the proximal end 705 allowing the light diffusing device 700 to be connected to a light source (not shown). As best shown in FIG. 7B the light diffusing device 700 is made for reasons of economy as well as flexibility from a plastic optical fiber 10 approximately 1 mm in diameter which comprises a light transmitting core fiber 710 made of PMMA (acrylic) surrounded by cladding 708 made of fluorinated polymers. It should be mentioned that other kinds of light transmitting fibers (not shown) could also be used and are therefore contemplated by and within the scope of the invention. The core fiber 710 and cladding 708 have different indexes of refraction, which enables light entering the light diffusing device 700 at a proximal location to be transmitted along the length of the light diffusing device 700 and thereby transmitted to a more distal location. The light diffusing device 700 defines a distal end 706 to which is attached a piercing tip 714, preventing the escape of the transmitted light energy from an open distal end (not shown) of the core fiber 710. The piercing tip 714 also allows the device 700 to pierce or penetrate and thereby be implanted into tissue following the application of gentle force by the physician. In one embodiment, the piercing tip 714 is made of machined (sharpened) stainless steel and also functions to pierce or penetrate tissue as required for treatment. Using appropriate medical grade adhesives, the piercing tip 714 is attached to the distal end 706 of the optical fiber 10 after the distal end 706 is roughened by such means as sandpaper, sandblasting, chemical degradation or other abrasive or erosive methods. In an alternative embodiment (not shown) the light diffusing device 700 may be encased in a transparent protective sheath (not shown) which provides an additional degree of integrity as well as smoothness.

In this embodiment the light diffusing device 700 has an exposed section of core fiber 710 which defines the light emitting section 702. The light emitting section 702 is further defined by a plurality of removed core fiber sections 704 which extend into the core fiber 710 allowing additional transmitted light energy to be emitted from the light diffusing device 700. As best shown in FIG. 7, the light emitting section 702 is characterized by the removed core fiber sections 704 being similarly numbered and progressively defining a greater surface area as the distal end 706 is reached. The removed core fiber sections 704 are conically shaped and spacing may vary in diameter between 0.003 inches to 0.006 inches. Restated, progressively greater sized removed core fiber sections 704 toward the distal end 702a result in a lesser exposed core fiber 710 surface area at the proximal end 702b of the light emitting section 702 and a greater exposed core fiber 710 surface area at the distal end 702a of the light emitting section 702, allowing a greater quantity of light to be available at the distal end 706 of the light emitting section 702. The reason for this is that if the exposed surface area of the removed core fiber sections 704 was consistent (not shown), more light would be emitted from the more proximally located removed core fiber sections 704, leaving less light available to be emitted from the more distally located removed core fiber sections 704. The result of similarly sized removed core fiber sections 704 (not shown) would be an optical fiber (not shown) having uneven light distribution, with more intensity toward the proximal end and less toward the distal end. The embodiment of the light diffusing device 700 shown in FIGS. 7-7B thus evenly emits the transmitted light energy along the length of the light emitting section 702, allowing safer and more precise photodynamic therapy.

Figure 8:
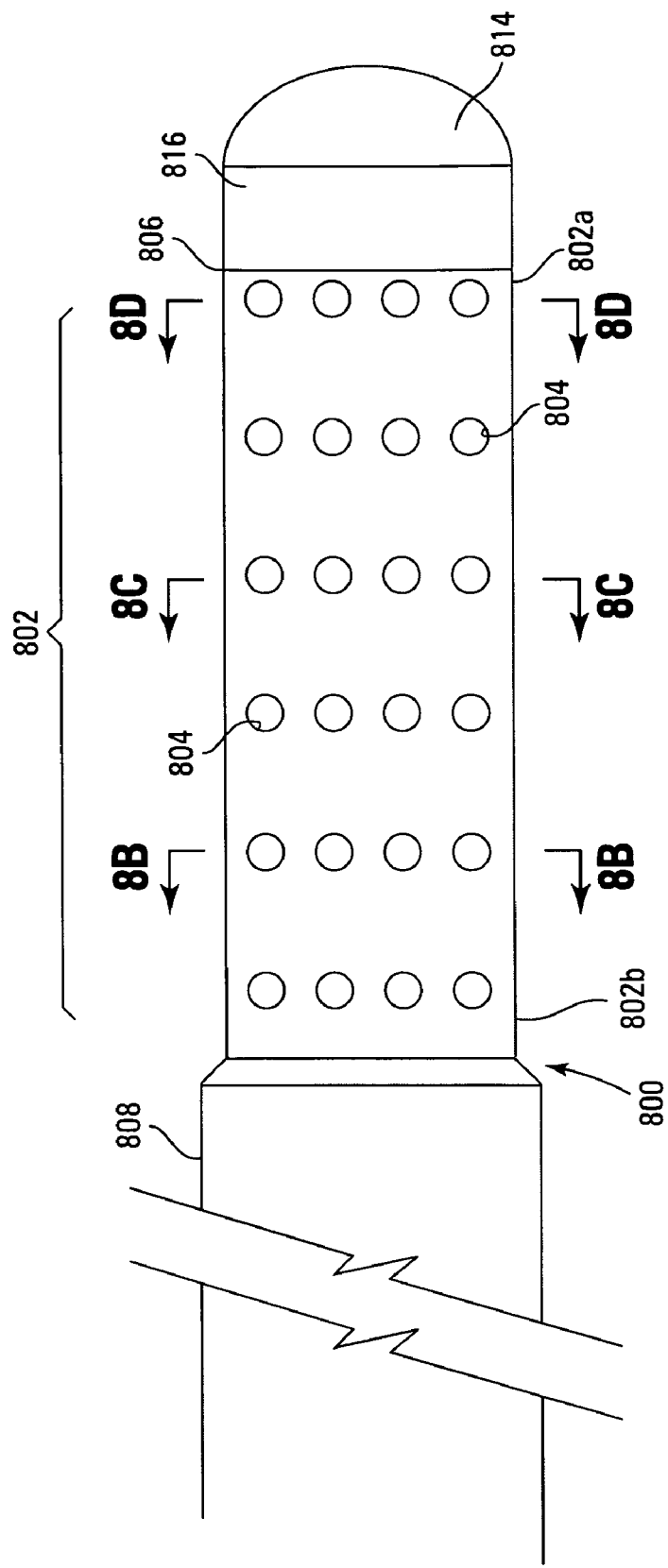
FIG. 8 shows the distal end of an embodiment of the light diffusing device of the present invention having an exposed core fiber at the distal end with a plurality of similarly sized removed core fiber sections distally increasing in depth into the core fiber.
Figure 8A:
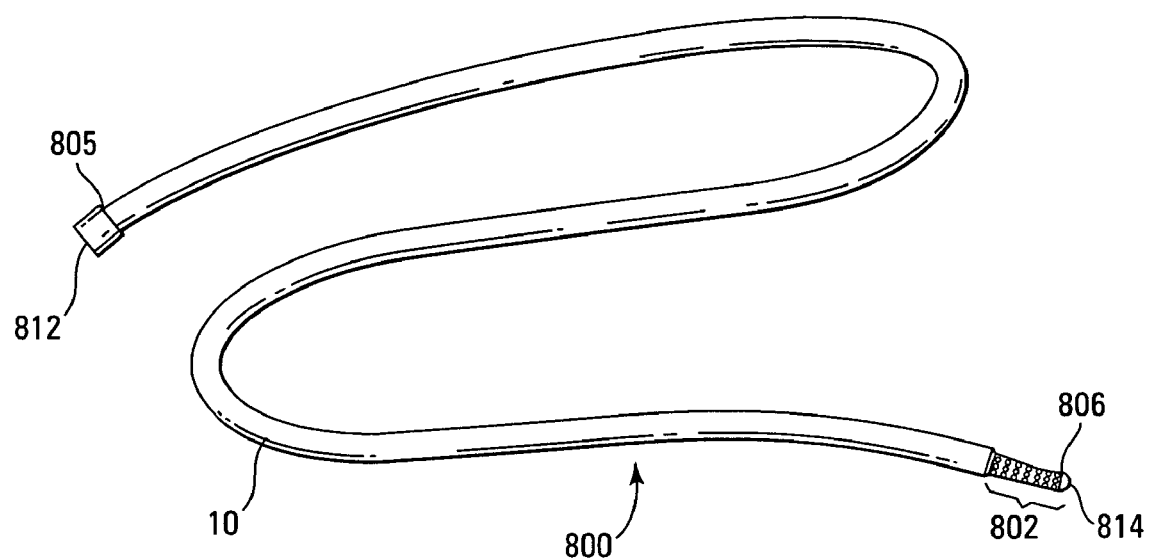
FIG. 8A is a plan view of the light diffusing device shown in FIG. 8.
Figure 8B:
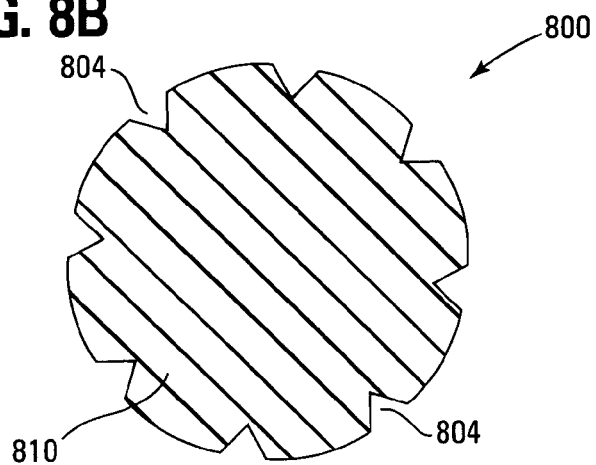
FIG. 8B is a lateral cross section taken through the lines 8B-3B as shown in FIG. 8, showing removed core fiber sections and into the core fiber having a relatively shallow depth.
Figure 8C:
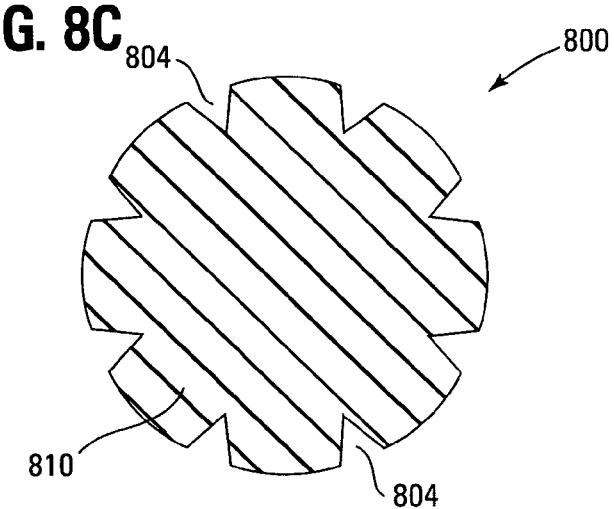
FIG. 8C is a lateral cross section taken through the lines 8C-8C as shown in FIG. 8, showing removed core fiber sections and into the core fiber having a relatively intermediate depth.
Figure 8D:
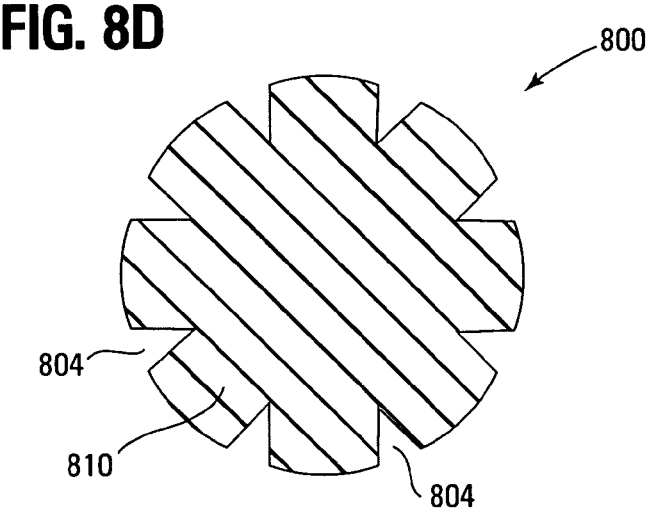
FIG. 8D is a lateral cross section taken through the lines 8D-8D as shown in FIG. 8, showing removed core fiber sections and into the core fiber having a relatively deep depth.

FIG. 8 shows the light emitting section 802 of an embodiment of a light diffusing device 800 of the present invention. FIG. 8A shows the entire light diffusing device 800, including a connector 812 attached to the proximal end 805 allowing the light diffusing device 800 to be connected to a light source (not shown). As best shown in FIGS. 8C, 8D, 8E the light diffusing device 800 is made for reasons of economy as well as flexibility from a plastic optical fiber 10 approximately 1 mm in diameter which comprises a light transmitting core fiber 810 made of PMMA (acrylic) surrounded by cladding 808 made of fluorinated polymers. It should be mentioned that other kinds of light transmitting fibers (not shown) could also be used and are therefore contemplated by and within the scope of the invention. The core fiber 810 and cladding 808 have different indexes of refraction, which enables light entering the light diffusing device 800 at the connector 812 to be transmitted along the length of the light diffusing device 800 and thereby transmitted to a more distal location. In this embodiment a section of fluorescent material 816 is placed between the end piece 814 and the distal end 806 of the optical fiber 10. The fluorescent material 816 can be made of chromium crystal, however, this is not intended to be limiting as other materials including alexandrite, sapphire and others would also work. Using appropriate medical grade adhesives, the fluorescent material 816 is attached to the distal end 806 of the optical fiber 10 after the distal end 806 is roughened by such means as sandpaper, sandblasting, chemical degradation or other abrasive or erosive methods. Following attachment of the fluorescent material 816 to the optical fiber 10, the opaque end piece 814 is attached to the distal end (unnumbered) of the fluorescent material 816 using appropriate medical grade adhesives. The end piece 814 prevents the escape of light energy through the distal end 806. The fluorescent material 816 emits a signal when illuminated by light energy having a wavelength at least at an excitation wavelength and above and thus functions as a fluorescence feedback indicator. In this configuration, when the laser light source (not shown) is energized fluorescence occurs at the distal end 806 and is detected at the light source console (not shown) to verify the light diffusing device 800 is valid and functioning properly. In another embodiment (not shown) the end piece 814 may be omitted and replaced by other light blocking mechanisms including opaque epoxy or plastic materials. In an alternative embodiment (not shown) the light diffusing device 800 may be encased in a transparent protective sheath (not shown) which provides an additional degree of integrity as well as smoothness.

In this embodiment the light diffusing device 800 has an exposed section of core fiber 810 which defines the light emitting section 802. The light emitting section 802 is further defined by a plurality of removed core fiber sections 804 which extend through into the core fiber 800 allowing the transmitted light to be emitted from the light diffusing device 810. As best shown in FIGS. 8C, 8D, 8E the light emitting section 802 is characterized by the removed core fiber sections 804 having a similar surface area and extends progressively deeper into the core fiber 810 as the distal end 802*a* is reached. The removed core fiber sections 804 are conically shaped and the depth may vary between 0.004 inches to 0.008 inches. Restated, progressively deeper, similarly sized removed core fiber sections 804 toward the distal end 802*a* result in a lesser exposed core fiber 810 surface area at the proximal end 802*b* of the light emitting section 802 and a greater exposed core fiber 810 surface area at the distal end 802*a* of the light emitting section 802, allowing a greater quantity of light to be available at the distal end 802*a* of the light emitting section 802. The reason for this is that if the size and depth of removed core fiber sections 804 was consistent (not shown), more light would be emitted from the more proximally located removed core fiber sections 804, leaving less light available to be emitted from the more distally located removed core fiber sections 804. The result of similarly sized and depth removed core fiber sections 804 (not shown) would be a light diffusing device (not shown) having uneven light distribution, with more intensity toward the proximal end and less toward the distal end. The embodiment of the light diffusing device 800 shown in FIG. 8 thus evenly emits the transmitted light energy along the length of the light emitting section 802, allowing safer and more precise photodynamic therapy.

Figure 9A:
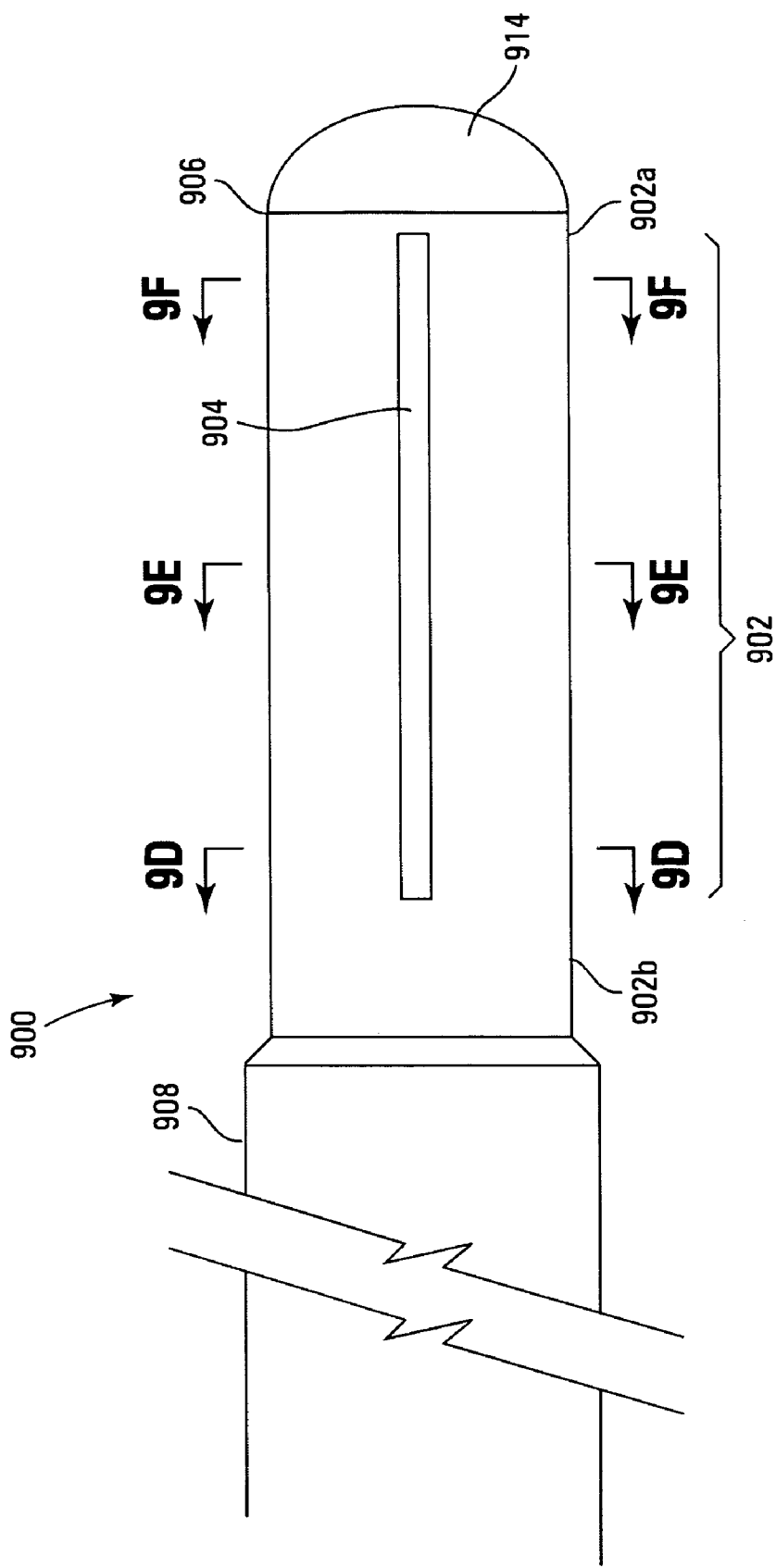
FIG. 9A is a top view of the distal end of a light diffusing device of the present invention having an exposed core fiber at the distal end with a continuous removed core fiber section extending progressively distally deeper into the core fiber.
Figure 9B:
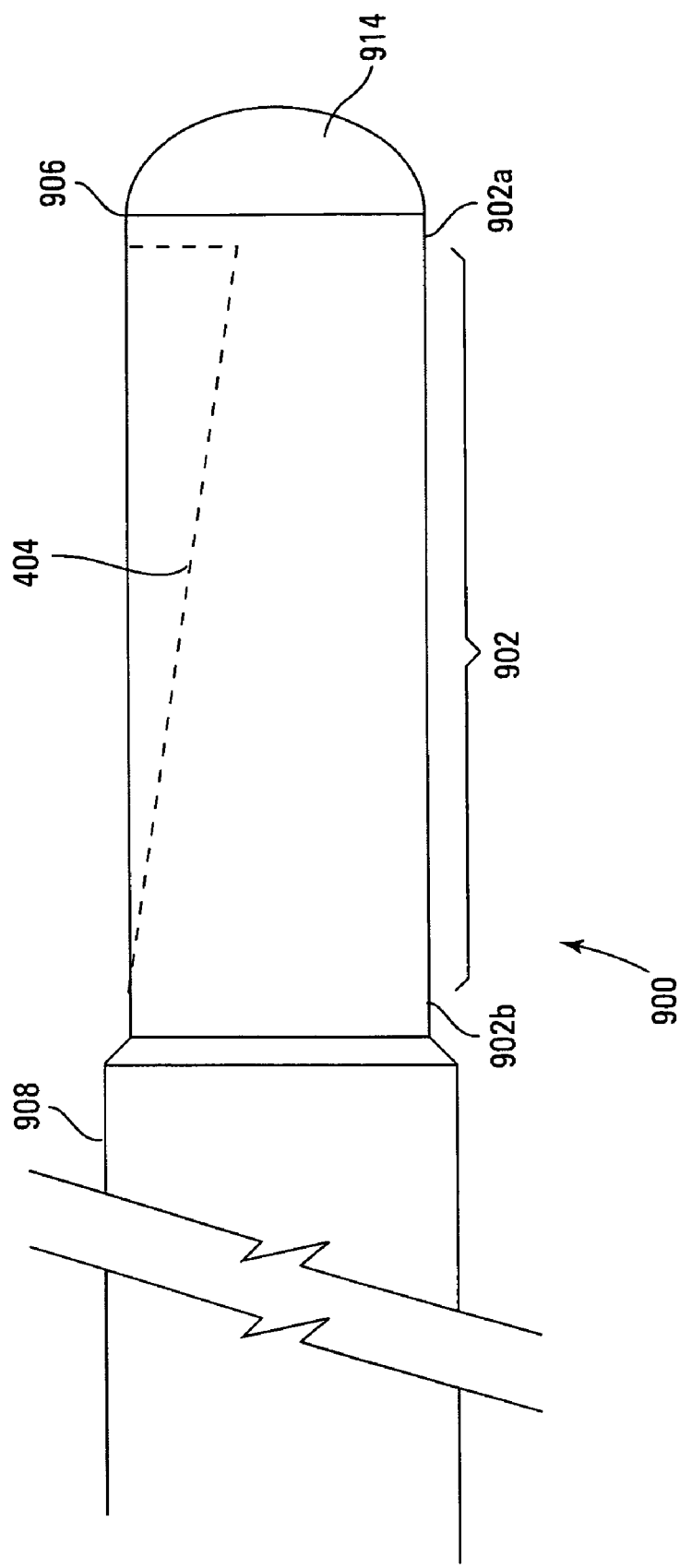
FIG. 9B is a side view of the distal end of the light diffusing device shown in FIG. 9A using phantom lines to show the continuous opening extending progressively distally deeper into the core fiber.
Figure 9C:
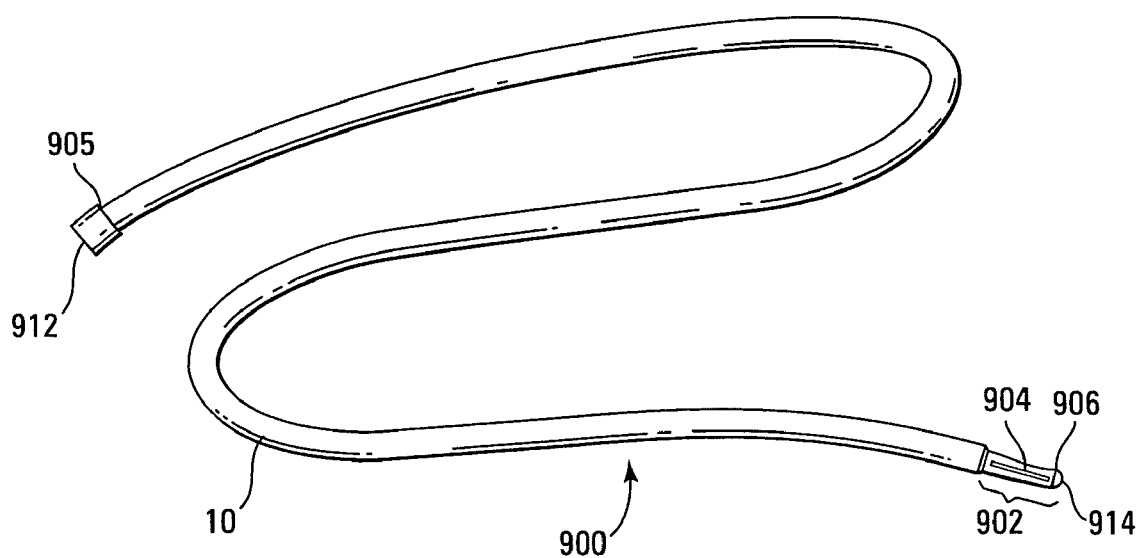
FIG. 9C is a plan view of the light diffusing device shown in FIG. 9.

FIG. 9A shows a top view of the light emitting section 902 of an embodiment of the light diffusing device 900 of the present invention. A side view of the light emitting section 902 is shown in FIG. 9B, with phantom lines indicating the depth of the continuous removed core fiber section 904. FIG. 9C shows the entire light diffusing device 900, including a connector 912 attached to the proximal end 905 allowing the light diffusing device 900 to be connected to a light source (not shown). As best shown in FIGS. 9A, 9B the light diffusing device 900 is made for reasons of economy as well as flexibility from a plastic optical fiber 10 approximately 1 mm in diameter which comprises a light transmitting core fiber 910 made of PMMA (acrylic) surrounded by cladding 908 made of fluorinated polymers. It should be mentioned that other kinds of light transmitting fibers (not shown) could also be used and are therefore contemplated by and within the scope of the invention. The core fiber 910 and cladding 908 have different indexes of refraction, which enables light entering the light diffusing device 900 at the connector 912 to be transmitted along the length of the light diffusing device 900 and thereby transmitted to a more distal location. The light diffusing device 900 defines a distal end 906 to which is attached an opaque end piece 914, preventing the escape of the transmitted light energy from an otherwise open distal end (not shown) of the core fiber 910. In one embodiment, the end piece 914 is made of stainless steel. Using appropriate medical grade adhesives, the end piece 914 is attached to the distal end 906 of the optical fiber 10 after the distal end 906 is roughened by such means as sandpaper, sandblasting, chemical degradation or other abrasive methods. In another embodiment (not shown) the end piece 914 may be omitted and replaced by other light blocking mechanisms including opaque epoxy or plastic materials. In an alternative embodiment (not shown) the light diffusing device 900 may be encased in a transparent protective sheath (not shown) which provides an additional degree of integrity as well as smoothness.

Figure 9D:
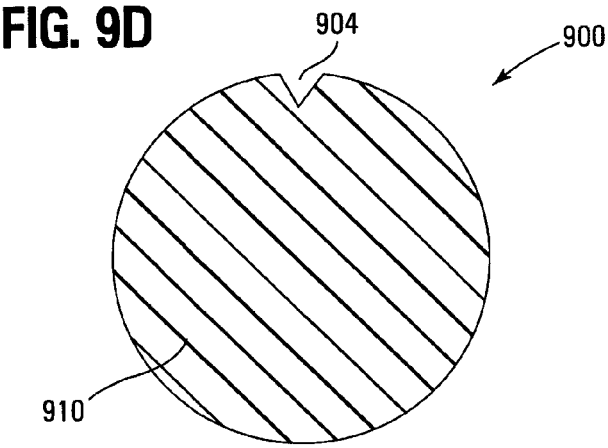
FIG. 9D is a lateral cross section taken through the lines 9D-9D as shown in FIG. 9, showing the removed core fiber section extending into the core fiber to a relatively shallow depth.
Figure 9E:
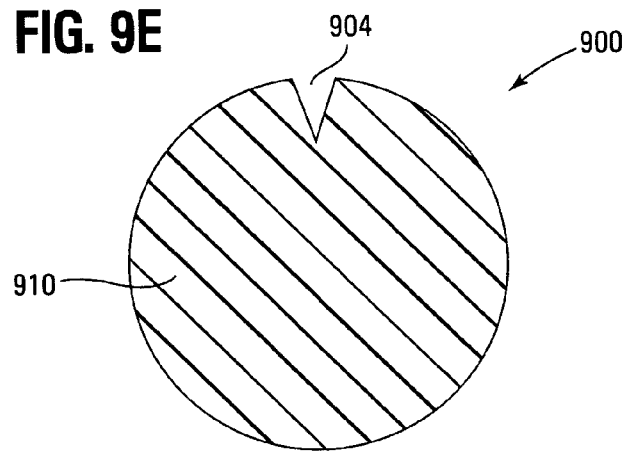
FIG. 9E is a lateral cross section taken through the lines 9E-9E as shown in FIG. 9, showing the removed core fiber section extending into the core fiber to a relatively intermediate depth.
Figure 9F:
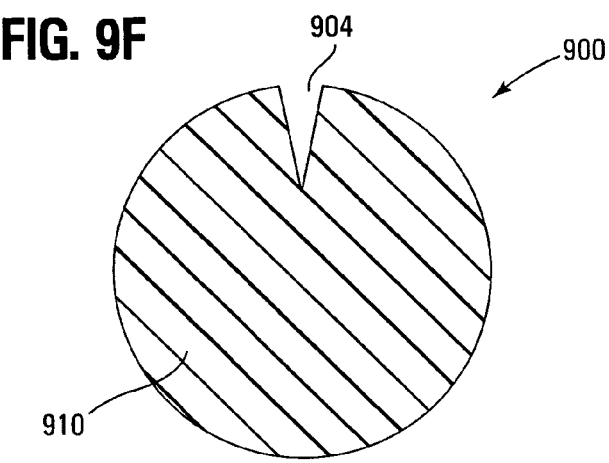
FIG. 9F is a lateral cross section taken through the lines 9F-9F as shown in FIG. 9, showing the removed core fiber section extending into the core fiber to a relatively deep depth.

In this embodiment the light diffusing device 900 has an exposed section of core fiber 910 which defines the light emitting section 902. The light emitting section 902 is further defined by an extended removed core fiber section 904 which is cut into the core fiber 910 allowing an increased amount of transmitted light to be emitted from the light diffusing device 900. While a single extended removed core fiber section 904 is shown in FIGS. 9-9F, this is for purposes of illustration only and the invention could also include multiple extended removed core fiber sections 904 (not shown). As best shown in FIGS. 9D, 9E, 9F, the light emitting section 902 is characterized by the removed core fiber section 904 extending progressively deeper into the core fiber 910 as the distal end 902*a* is reached. Restated, the progressively deeper removed core fiber section 904 toward the distal end 902*a* results in a lesser exposed core fiber 910 surface area at the proximal end 902*b* of the light emitting section 902 and a greater exposed core fiber 910 surface area at the distal end 902*a* of the light emitting section 902, allowing a greater quantity of light to be available at the distal end 902*a* of the light emitting section 902. The reason for this is that if the depth of the removed core fiber section 904 was consistent (not shown), more light would be emitted from the proximal end of the removed core fiber section 904, leaving less light available to be emitted from the distal end of the removed core fiber section 904. The result of a uniform depth removed core fiber section 904 (not shown) would be a light diffusing device (not shown) having uneven light distribution, with more intensity toward the proximal end and less toward the distal end. The embodiment of the light diffusing device 900 shown in FIG. 9 thus evenly emits the transmitted light energy along the length of the light emitting section 902, allowing safer and more precise photodynamic therapy.

Figure 10:
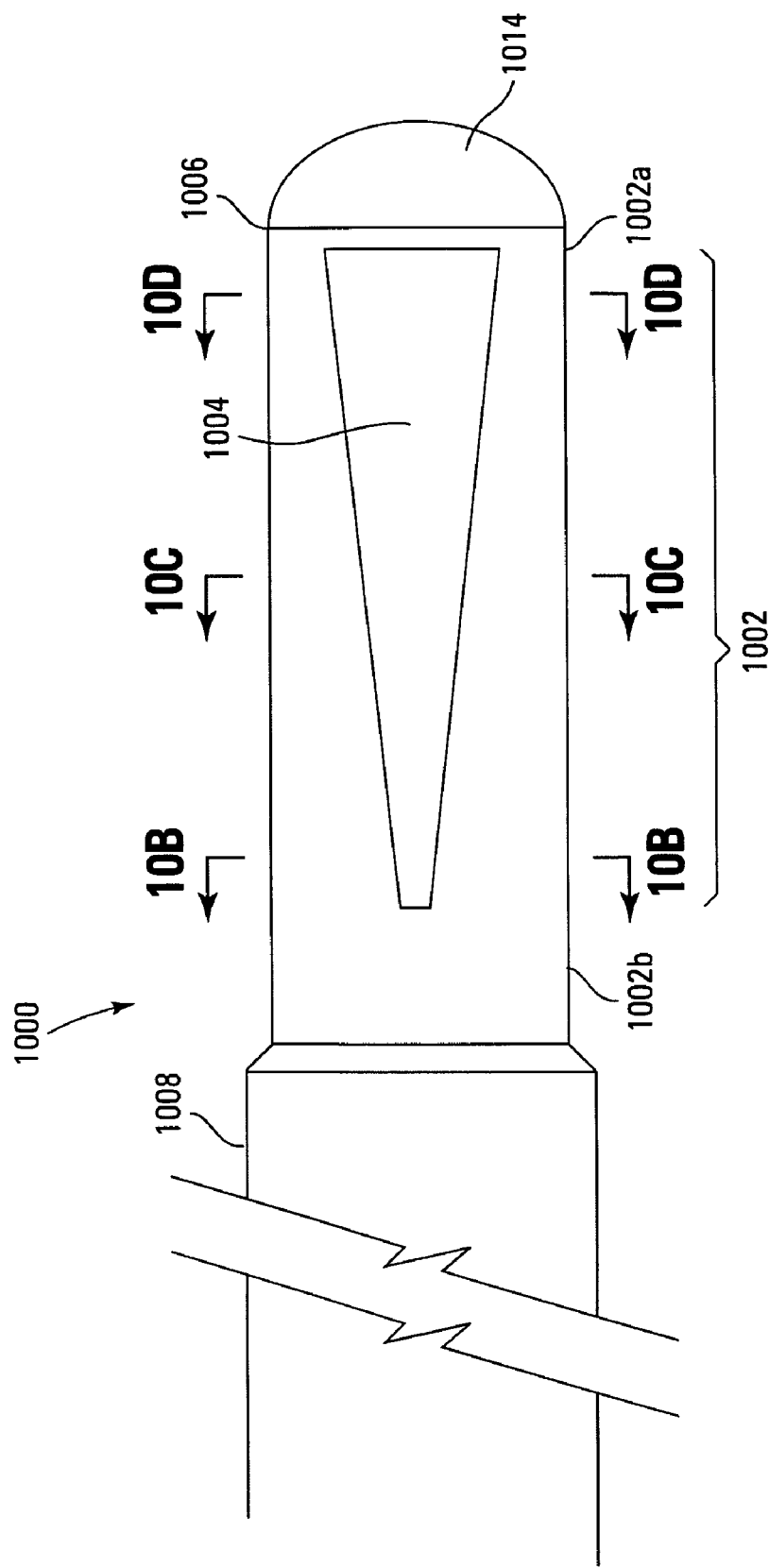
FIG. 10 shows the distal end of a light diffusing device of the present invention having an exposed core fiber at the distal end with a continuous removed core fiber section extending distally wider across the core fiber.
Figure 10A:
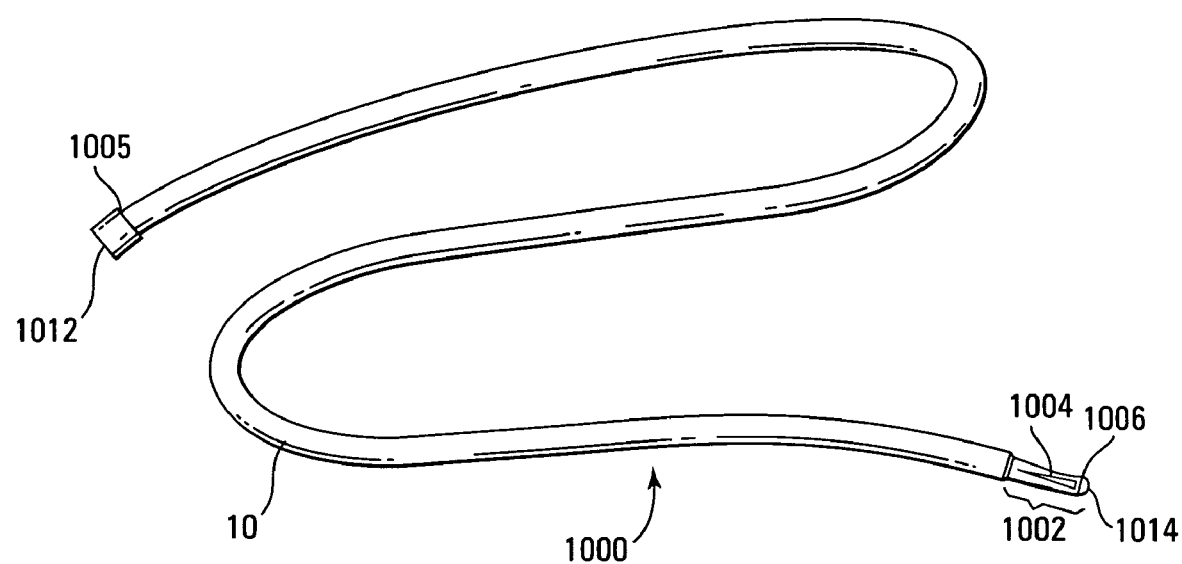
FIG. 10A is a plan view of the light diffusing device shown in FIG. 10.
Figure 10B:
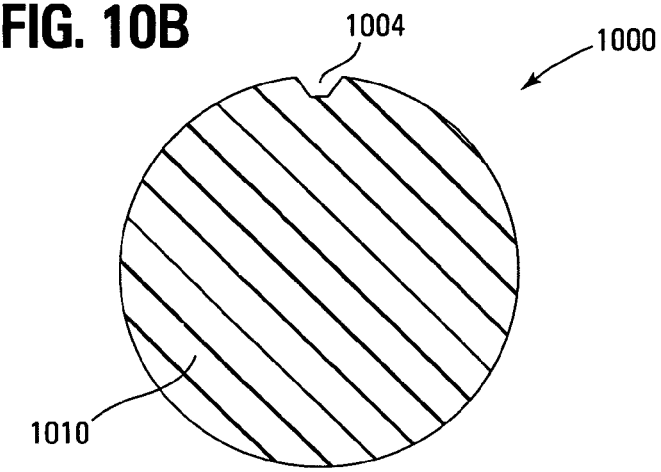
FIG. 10B is a lateral cross section taken through the lines 10B-10B as shown in FIG. 10, showing the removed core fiber section extending into the core fiber to a relatively narrow width.
Figure 10C:
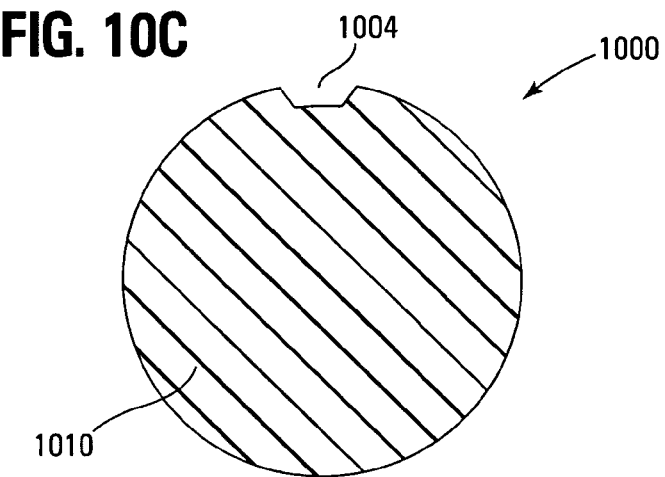
FIG. 10C is a lateral cross section taken through the lines 10C-10C as shown in FIG. 10, showing the removed core fiber section extending into the core fiber to a relatively intermediate width.

FIG. 10 shows the light emitting section 1002 of an embodiment of the light diffusing device 1000 of the present invention. FIG. 10A shows the entire light diffusing device 1000, including a connector 1012 attached to the proximal end 1005 allowing the light diffusing device 1000 to be connected to a light source (not shown). As best shown in FIG. 10 the light diffusing device 1000 is made for reasons of economy as well as flexibility from a plastic optical fiber 10 approximately 1 mm in diameter which comprises a light transmitting core fiber 1010 made of PMMA (acrylic) surrounded by cladding 1008 made of fluorinated polymers. It should be mentioned that other kinds of light transmitting fibers (not shown) could also be used and are therefore contemplated by and within the scope of the invention. The core fiber 1010 and cladding 1008 have different indexes of refraction, which enables light entering the light diffusing device 1000 at the connector 1012 to be transmitted along the length of the light diffusing device 1000 and thereby transmitted to a more distal location. The light diffusing device 1000 defines a distal end 1006 to which is attached an opaque end piece 1014, preventing the escape of the transmitted light energy from an open distal end (not shown) of the core fiber 1010. In one embodiment, the end piece 1014 is made of stainless steel. Using appropriate medical grade adhesives, the end piece 1014 is attached to the distal end 1006 of the optical fiber 10 after the distal end 1006 is roughened by such means as sandpaper, sandblasting, chemical degradation or other abrasive methods. In another embodiment (not shown) the end piece 1014 may be omitted and replaced by other light blocking mechanisms including opaque epoxy or plastic materials. In an alternative embodiment (not shown) the light diffusing device 1000 may be encased in a transparent protective sheath (not shown) which provides an additional degree of integrity as well as smoothness.

Figure 10D:
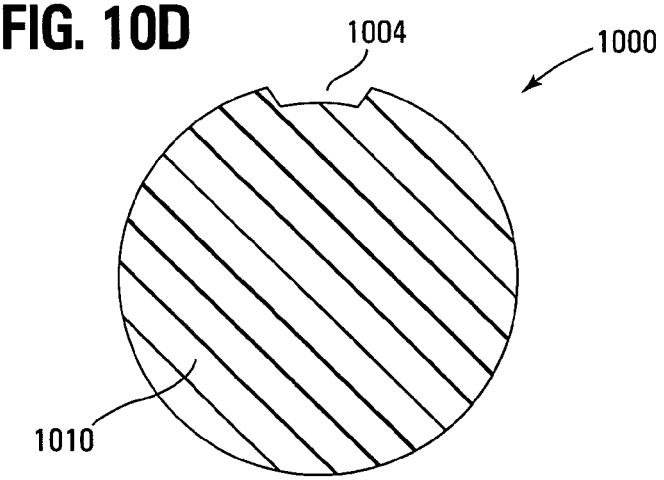
FIG. 10D is a lateral cross section taken through the lines 10D-10D as shown in FIG. 10, showing the removed core fiber section extending into the core fiber to a relatively wide width.

In this embodiment the light diffusing device 1000 has an exposed section of core fiber 1010 which defines the light emitting section 1002. The light emitting section 1002 is further defined by an extended removed core fiber section 1004 which is cut into the core fiber 1010 exposing a distally increased surface of core fiber 1010, allowing an increased amount of transmitted light to be emitted from the light diffusing device 1000. While a single extended removed core fiber section 1004 is shown in FIGS. 10-10D, this is for purposes of illustration only and the invention could also include multiple extended removed core fiber sections 1004 (not shown). As best shown in FIGS. 10, 10A, 10B, 10C, 10D, the light emitting section 1002 is characterized by the removed core fiber section 1004 extending progressively wider into the core fiber 1010 as the distal end 1002a is reached. Restated, the progressively wider removed core fiber section 1004 toward the distal end 1002a results in a lesser exposed core fiber 1010 surface area at the proximal end 1002b of the light emitting section 1002 and a greater exposed core fiber 1010 surface area at the distal end 1002a of the light emitting section 1002, allowing a greater quantity of light to be available at the distal end 1002a of the light emitting section 1002. The reason for this is that if the width and depth of the removed core fiber section 1004 was consistent (not shown), more light would be emitted from the proximal end 1002b of the removed core fiber section 1004, leaving less light available to be emitted from the distal end of the removed core fiber section 1004. The result of a uniform width/depth removed core fiber section 1004 (not shown) would be a light diffusing device (not shown) having uneven light distribution, with more intensity toward the proximal end 1002b and less toward the distal end 1002a. The embodiment of the light diffusing device 1000 shown in FIG. 10 thus evenly emits the transmitted light energy along the length of the light emitting section 1002, allowing safer and more precise photodynamic therapy.

Figure 11:
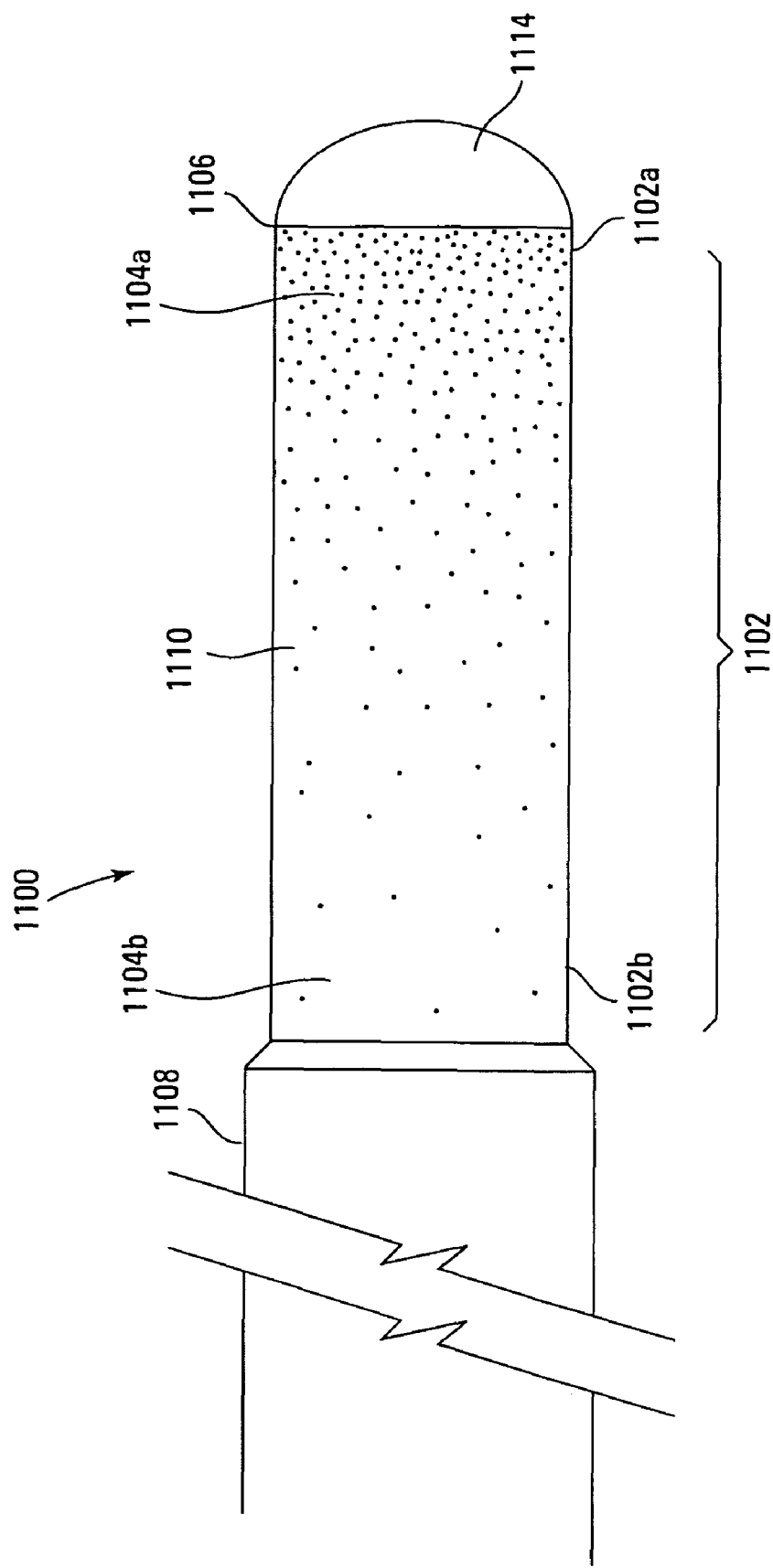
FIG. 11 shows the distal end of an embodiment of the light diffusing device of the present invention having an exposed core fiber at the distal end with the exposed core fiber progressively distally rougher.
Figure 11A:
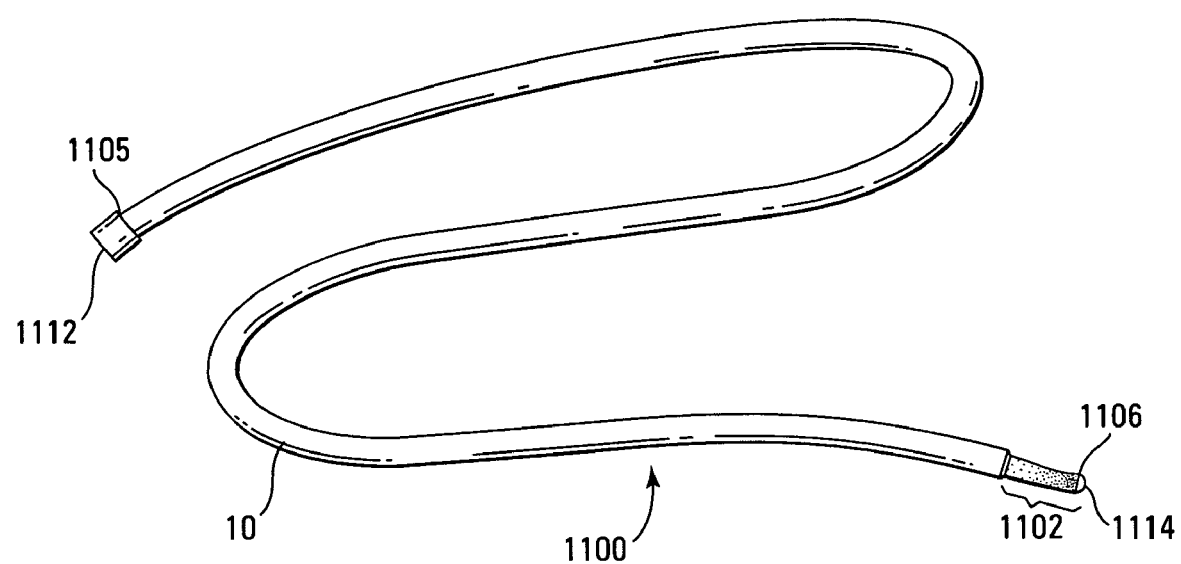
FIG. 11A is a plan view of the light diffusing device shown in FIG. 11.

FIG. 11 shows the light emitting section 1102 of an embodiment of the light diffusing device 1100 of the present invention. A plan view of the light emitting section as shown in FIG. 11A shows the entire light diffusing device 1100, including a connector 1112 attached to the proximal end 1105 allowing the light diffusing device 1100 to be connected to a light source (not shown). As best shown in FIG. 9 the light diffusing device 1100 is made for reasons of economy as well as flexibility from a plastic optical fiber 10 approximately 1 mm in diameter which comprises a light transmitting core fiber 1110 made of PMMA (acrylic) surrounded by cladding 1108 made of fluorinated polymers. It should be mentioned that other kinds of light transmitting fibers (not shown) could also be used and are therefore contemplated by and within the scope of the invention. The core fiber 1110 and cladding 1108 have different indexes of refraction, which enables light entering the light diffusing device 1100 at the connector 1112 to be transmitted along the length of the light diffusing device 1100 and thereby transmitted to a more distal location. The light diffusing device 1100 defines a distal end 1106 which comprises an opaque end piece 1114, preventing the escape of the transmitted light energy from an open distal end (not shown) of the core fiber 1110. In one embodiment, the end piece 1114 is made of stainless steel. Using appropriate medical grade adhesives, the end piece 1114 is attached to the distal end 1106 of the light diffusing device 1100 after the distal end 1106 is roughened by such means as sandpaper, sandblasting, chemical degradation or other abrasive methods. In another embodiment (not shown) the end piece 1114 may be omitted and replaced by other light blocking mechanisms including opaque epoxy or plastic materials. In an alternative embodiment (not shown) the light diffusing device 1100 may be encased in a transparent protective sheath (not shown) which provides an additional degree of integrity as well as smoothness.

In this embodiment the light diffusing device 1100 has an exposed section of core fiber 1110 which defines the light emitting section 1102. The light emitting section 1102 is further defined by progressively distally roughening the surface of the light emitting section 1102 allowing an increased amount of transmitted light to be emitted from the light diffusing device 1100. As best shown in FIG. 11 the light emitting section 1102 is characterized by the light emitting section 1102 having a relatively smooth area 1104b which becomes progressively rougher 1104a along the core fiber 1110 as the distal end 1102a is reached. Restated, the progressively rougher light emitting section 1102 toward the distal end 1102a results in a lesser exposed core fiber 1110 surface area at the proximal end 1102b of the light emitting section 1102 and a greater exposed core fiber 1110 surface area at the distal end 1102a of the light emitting section 1102, allowing a greater quantity of light to be available at the distal end (unnumbered) of the light emitting section 1102. The reason for this is that if the roughness of the light emitting section 1102 was consistent (not shown), more light would be emitted from the proximal end of the light emitting section 1102, leaving less light available to be emitted from the distal end of the light emitting section 1102. The result of a uniform roughness light emitting section 1102 (not shown) would be a light diffusing device (not shown) having uneven light distribution, with more intensity toward the proximal end and less toward the distal end. The embodiment of the light diffusing device 1100 shown in FIG. 11 thus evenly emits the transmitted light energy along the length of the light emitting section 1102, allowing safer and more precise photodynamic therapy.

Figure 12:
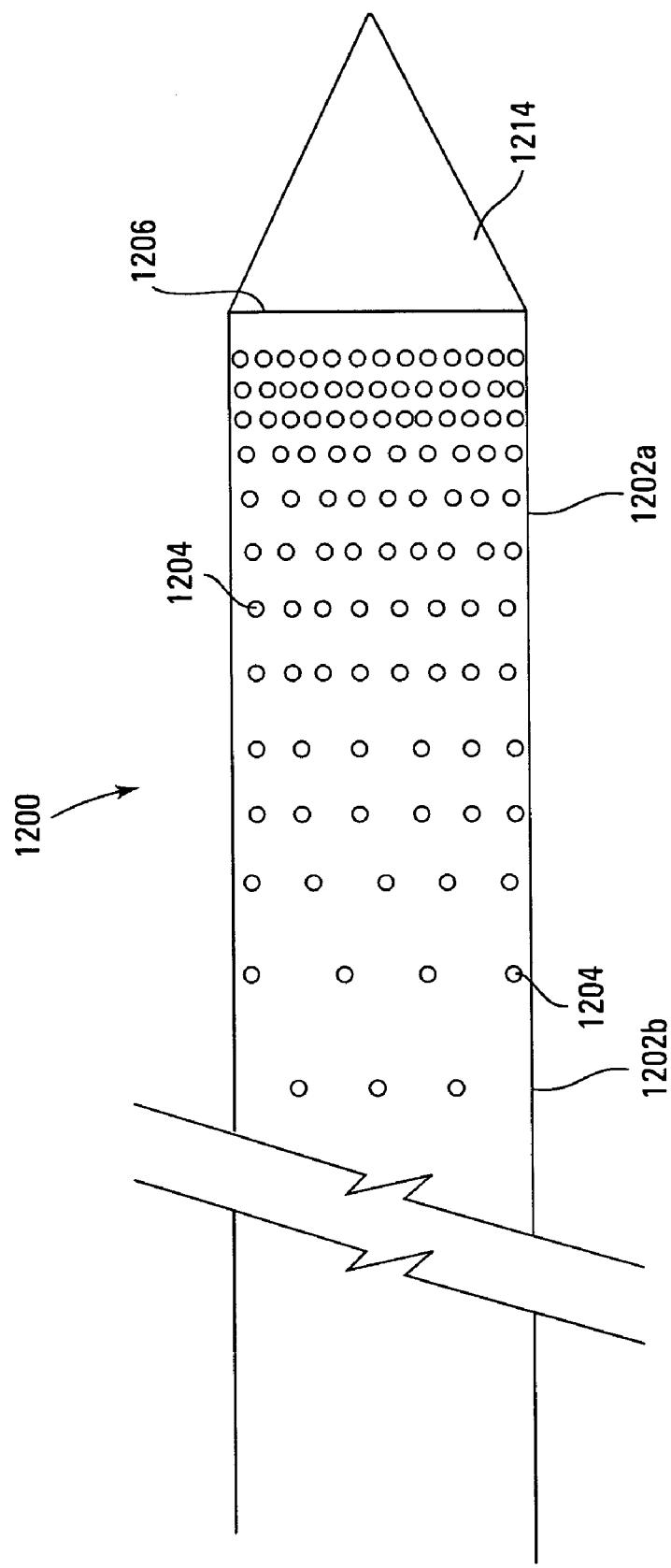
FIG. 12 shows the distal end of an embodiment of the light diffusing device of the present invention having a plurality of similarly sized open areas through the cladding distally progressively closer in proximity to each other. A piercing tip is attached to the distal end of the device.
Figure 12A:
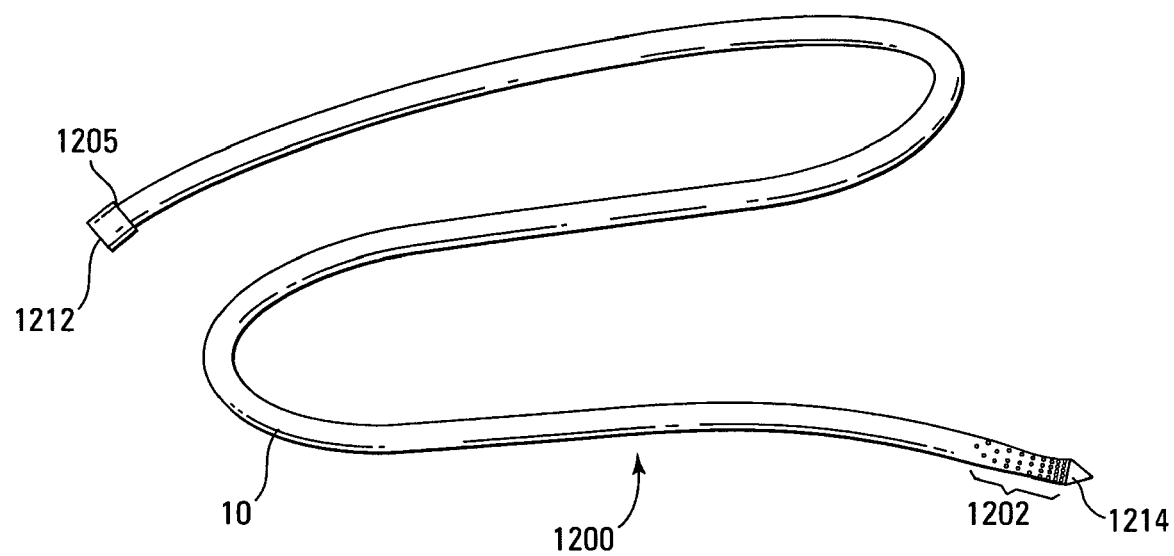
FIG. 12A is a plan view of the light diffusing device shown in FIG. 12.

FIG. 12 shows the light emitting section 1202 of an embodiment of a light diffusing device 1200 of the present invention. FIG. 12A shows the entire light diffusing device 1200, including a connector 1212 attached to the proximal end 1205 allowing the light diffusing device 1200 to be connected to a light source (not shown). As best shown in FIG. 12B the light diffusing device 1200 is made for reasons of economy as well as flexibility from a plastic optical fiber 10 approximately 1 mm in diameter which comprises a light transmitting core fiber 1210 made of PMMA (acrylic) surrounded by cladding 1208 made of fluorinated polymers. It should be mentioned that other kinds of light transmitting fibers (not shown) could also be used and are therefore contemplated by and within the scope of the invention. The core fiber 1210 and cladding 1208 have different indexes of refraction, which enables light entering the light diffusing device 1200 at the connector 1212 to be transmitted along the length of the light diffusing device 1200 and therefore transmitted to a more distal location. The light diffusing device 1200 defines a distal end 1206 to which is attached a piercing tip 1214, which prevents the escape of the transmitted light energy from an open distal end (not shown) of the core fiber 1210. The piercing tip 1214 also allows the device 1200 to pierce or penetrate and thereby be implanted into tissue following the application of gentle force by the physician. In one embodiment, the piercing tip 1214 is made of machined (sharpened) stainless steel, however, this is not intended to be limiting as other metallic, composite and polymeric materials would also work. Using appropriate medical grade adhesives, the piercing tip 1214 is attached to the distal end 1206 of the optical fiber 10 after the distal end 1206 is roughened by such means as sandpaper, sandblasting, chemical degradation or other abrasive or erosive methods.

The light emitting section 1202 is defined by a plurality of light ports 1204 which extend through the cladding 1208 exposing core fiber 1210 allowing the transmitted light energy to be emitted from the light diffusing device 1200. As best shown in FIG. 12, the light emitting section 1202 is characterized by the light ports 1204 having a similar surface area and progressively denser in distribution (greater in number) as the distal end 1202a is reached. As shown in FIG. 12B the light ports 1204 are conically shaped and spacing may vary between 0.022 inches to 0.040 inches. Restated, a denser distribution of similarly sized light ports 1204 at the distal end 1202a results in a lesser exposed core fiber 1210 surface area at the proximal end 1202b of the light emitting section 1202 and a greater exposed core fiber 1210 surface area at the distal end 1202a of the light emitting section 1202, allowing a greater quantity of light to be available at the distal end 1202a of the light emitting section 1202. The reason for this is that if the distribution of light ports 1204 was even (not shown), more light would be emitted from the more proximally located light ports 1204, leaving less light available to be emitted from the more distally located light ports 1204. The result of evenly distributed light ports 1204 (not shown) would be an optical fiber (not shown) having uneven light distribution, with more intensity toward the proximal end and less toward the distal end. The embodiment of the light diffusing device 1200 shown in FIGS. 12-12B thus evenly emits the transmitted light energy along the length of the light emitting section 1202, allowing safer and more precise photodynamic therapy.

Figure 13A:
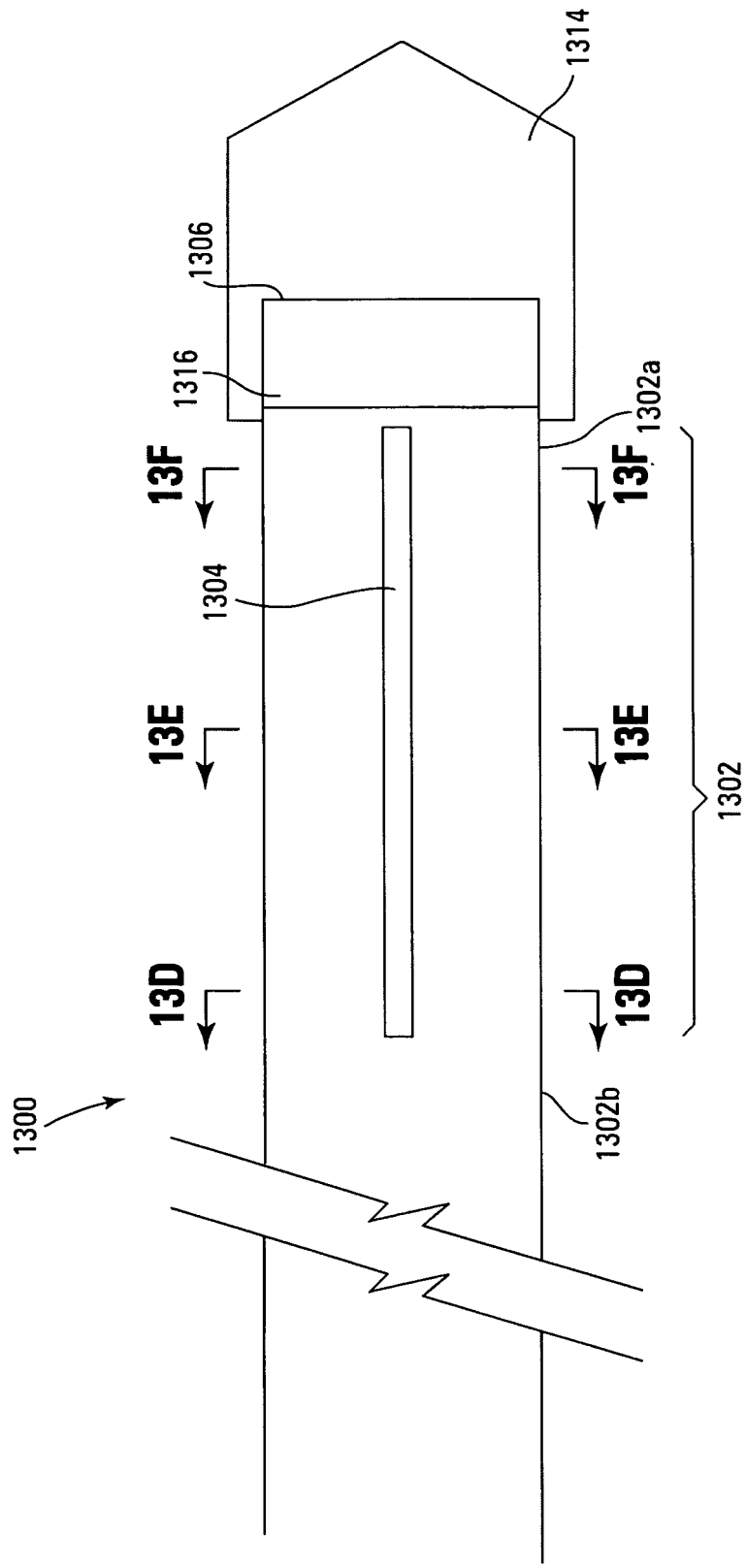
FIG. 13A is a top view of the distal end of a light diffusing device of the present invention having a continuous opening through the cladding and extending progressively distally deeper into the core fiber. A piercing tip is attached to the distal end of the device. Fluorescent material is embedded in the sheathing.
Figure 13B:
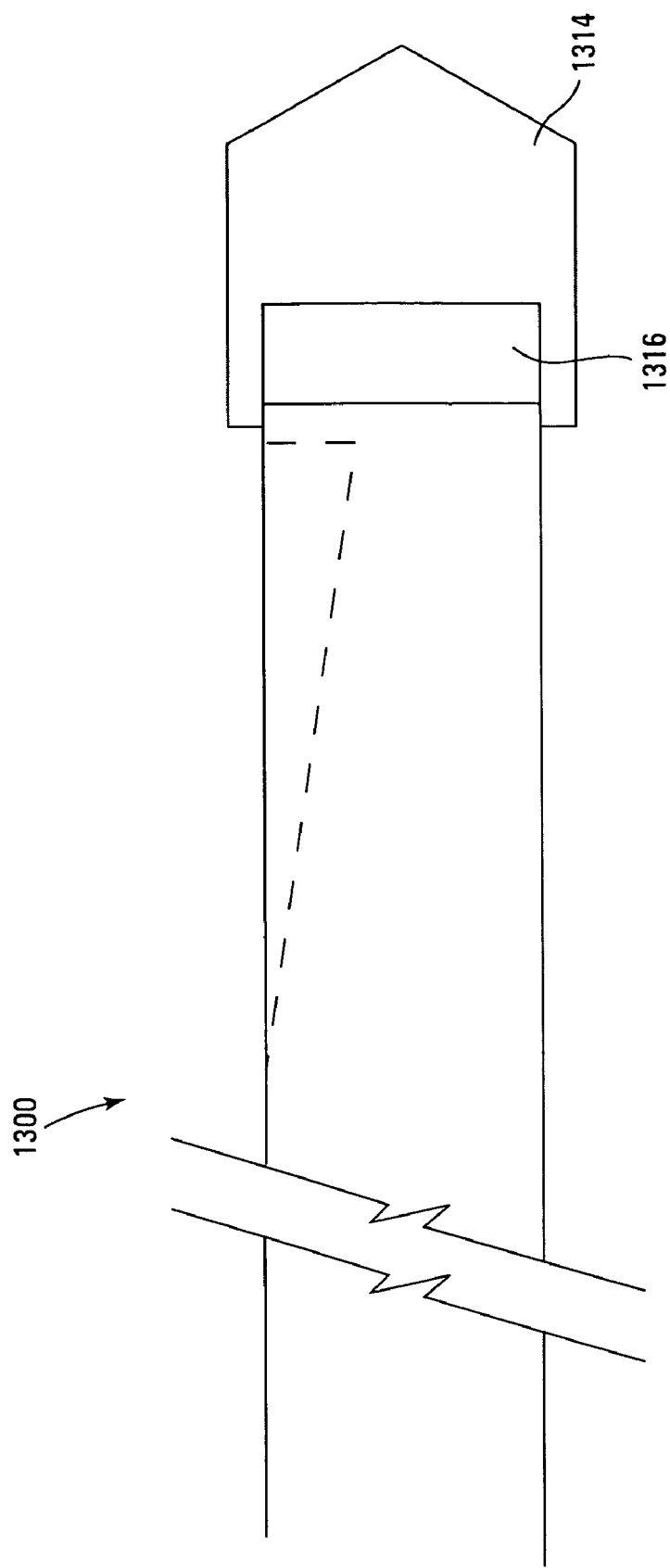
FIG. 13B is a side view of the distal end of the light diffusing device shown in FIG. 13A using phantom lines to show the continuous opening extending progressively distally deeper into the core fiber.
Figure 13C:
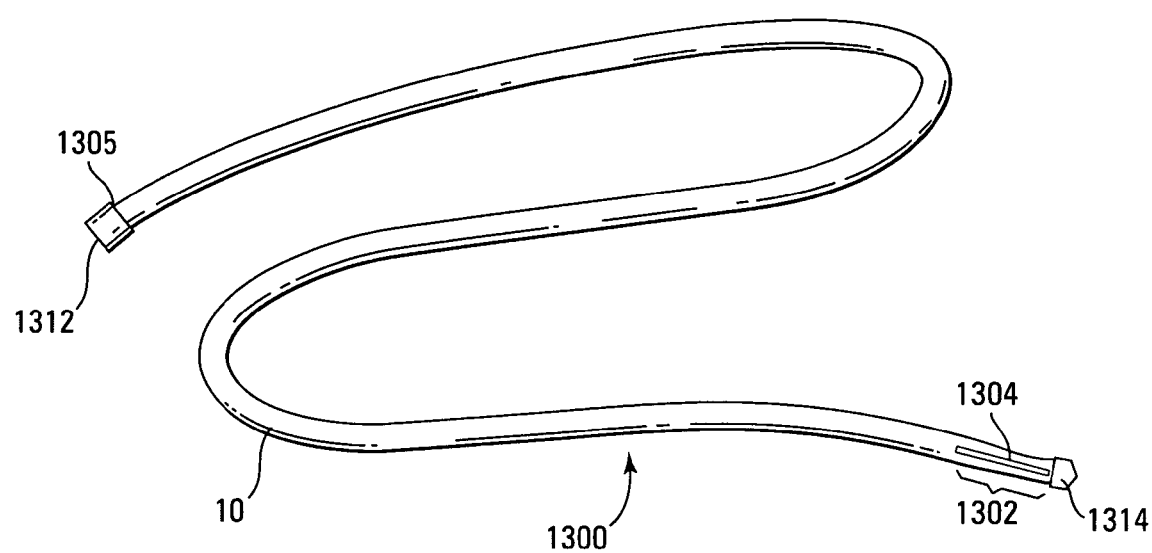
FIG. 13C is a plan view of the light diffusing device shown in FIGS. 13A-13B.
Figure 13D:
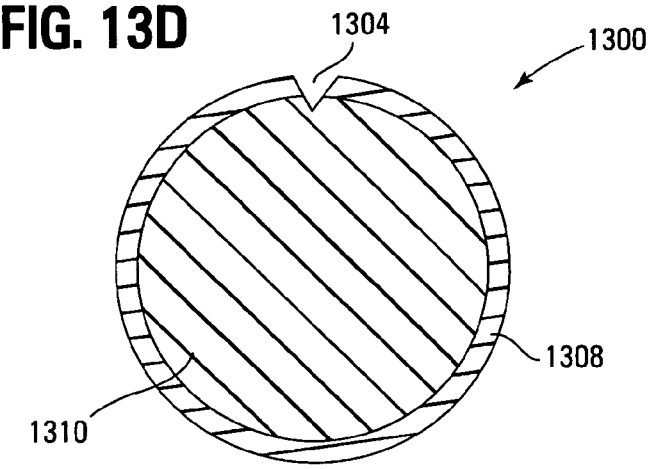
FIG. 13D is a lateral cross section taken through the lines 13D-13D as shown in FIGS. 13A-13B, showing the opening through the cladding and into the core fiber having a relatively shallow depth.
Figure 13E:
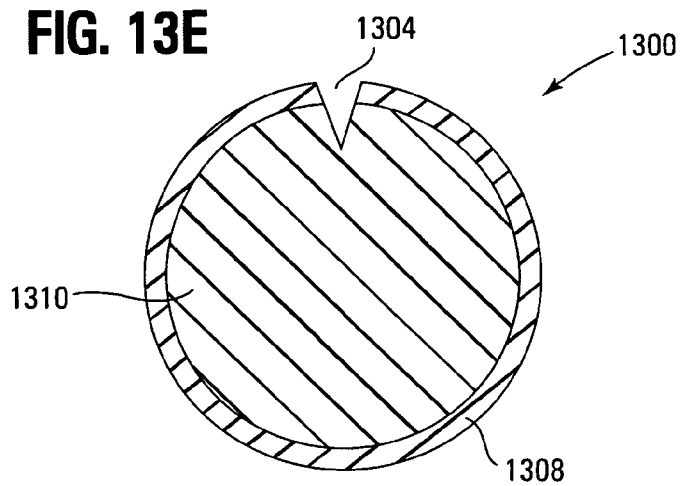
FIG. 13E is a lateral cross section taken through the lines 13E-13E as shown in FIGS. 13A-13B, showing the opening through the cladding and into the core fiber having a relatively intermediate depth.
Figure 13F:
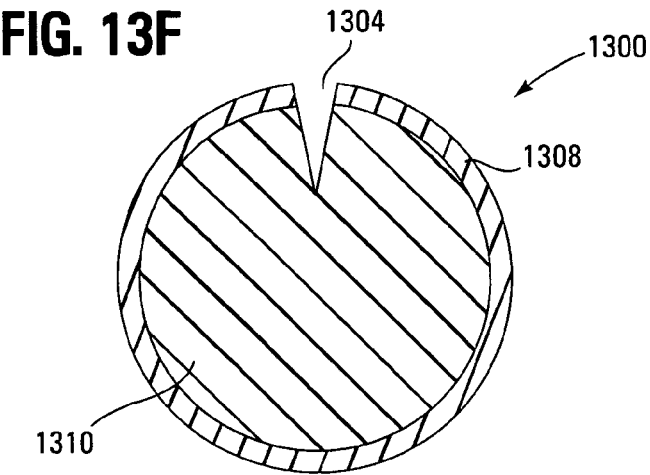
FIG. 13F is a lateral cross section taken through the lines 13F-13FD as shown in FIGS. 13A-13B, showing the opening through the cladding and into the core fiber having a relatively deep depth.

FIG. 13A shows a top view of the light emitting section 1302 of an embodiment of the light diffusing device 1300 of the present invention. A side view is shown in FIG. 13B, with phantom lines indicating the location and depth of the light port 1304. FIG. 13C shows the entire light diffusing device 1300, including a connector 1312 attached to the proximal end 1305 allowing the light diffusing device 1300 to be connected to a light source (not shown). As best shown in FIGS. 13D, 13E, 13F the light diffusing device 1300 is made for reasons of economy as well as flexibility from a plastic optical fiber 10 approximately 1 mm in diameter which comprises a light transmitting core fiber 1310 made of PMMA (acrylic) surrounded by cladding 1308 made of fluorinated polymers. It should be mentioned that other kinds of light transmitting fibers (not shown) could also be used and are therefore contemplated by and within the scope of the invention. The core fiber 1310 and cladding 1308 have different indexes of refraction, which enables light entering the light diffusing device 1300 at the connector 1312 to be transmitted along the length of the light diffusing device 1300 and thereby transmitted to a more distal location. The light diffusing device 1300 defines a distal end 1306 to which is attached a piercing tip 1314, preventing the escape of the transmitted light energy from an open distal end (not shown) of the core fiber 1310. The piercing tip 1314 also allows the device 1300 to pierce or penetrate and thereby be implanted into tissue following the application of gentle force by the physician. The piercing tip 1314 in one embodiment is made of machined (sharpened) stainless steel, however, other metallic, composite and polymeric materials are also contemplated by and therefore within the scope of the invention. In this embodiment a section of fluorescent material 1316 is placed between the piercing tip 1314 and the distal end 1306 of the optical fiber 10. The fluorescent material 1316 can be made of chromium crystal, however, this is not intended to be limiting as other materials including alexandrite, sapphire and others would also work. Using appropriate medical grade adhesives, the fluorescent material 1316 is attached to the distal end 1306 of the optical fiber 10 after the distal end 1306 is roughened by such means as sandpaper, sandblasting, chemical degradation or other abrasive or erosive methods. Following attachment of the fluorescent material 1316 to the optical fiber 10, the piercing tip 1314 is attached to the distal end (unnumbered) of the fluorescent material 1316 using appropriate medical grade adhesives. The piercing tip 1314 prevents the escape of light energy through the distal end 1306 as well as facilitating direct introduction into tissue. The fluorescent material 1316 emits a signal when illuminated by light energy having a wavelength at least at an excitation wavelength and above and thus functions as a fluorescence feedback indicator. In this configuration, when the laser light source (not shown) is energized fluorescence occurs at the distal end 1306 and is detected at the light source console (not shown) to verify the light diffusing device 1300 is valid and functioning properly. In an alternative embodiment (not shown) the light diffusing device 1300 may be encased in a transparent protective sheath (not shown) which provides an additional degree of integrity as well as smoothness.

The light emitting section 1302 is defined by an extended light port 1304 which is cut through the cladding 1308 into the core fiber 1300 allowing the transmitted light to be emitted from the light diffusing device 1300. While a single extended light port 1304 is shown in FIGS. 13-13F, this is for purposes of illustration only and the invention could also include multiple extended light ports 1304 (not shown). As best shown in FIGS. 13D, 13E, 13F, the light emitting section 1302 is characterized by the light port 1304 extending progressively deeper into the core fiber 1310 as the distal end 1302a is reached. Restated, the progressively deeper light port 1304 toward the distal end 1302a results in a lesser exposed core fiber 1310 surface area at the proximal end 1302b of the light emitting section 1302 and a greater exposed core fiber 1310 surface area at the distal end 1302a of the light emitting section 1302, allowing a greater quantity of light to be available at the distal end (unnumbered) of the light emitting section 1302. The reason for this is that if the depth of the light port 1304 was consistent (not shown), more light would be emitted from the proximal end of the light port 1304, leaving less light available to be emitted from the distal end of the light port 1304. The result of a uniform depth light port 1304 (not shown) would be an optical fiber (not shown) having uneven light distribution, with more intensity toward the proximal end and less toward the distal end. The embodiment of the light diffusing device 1300 shown in FIG. 13 thus evenly emits the transmitted light energy along the length of the light emitting section 1302, allowing safer and more precise photodynamic therapy.

Figure 14:
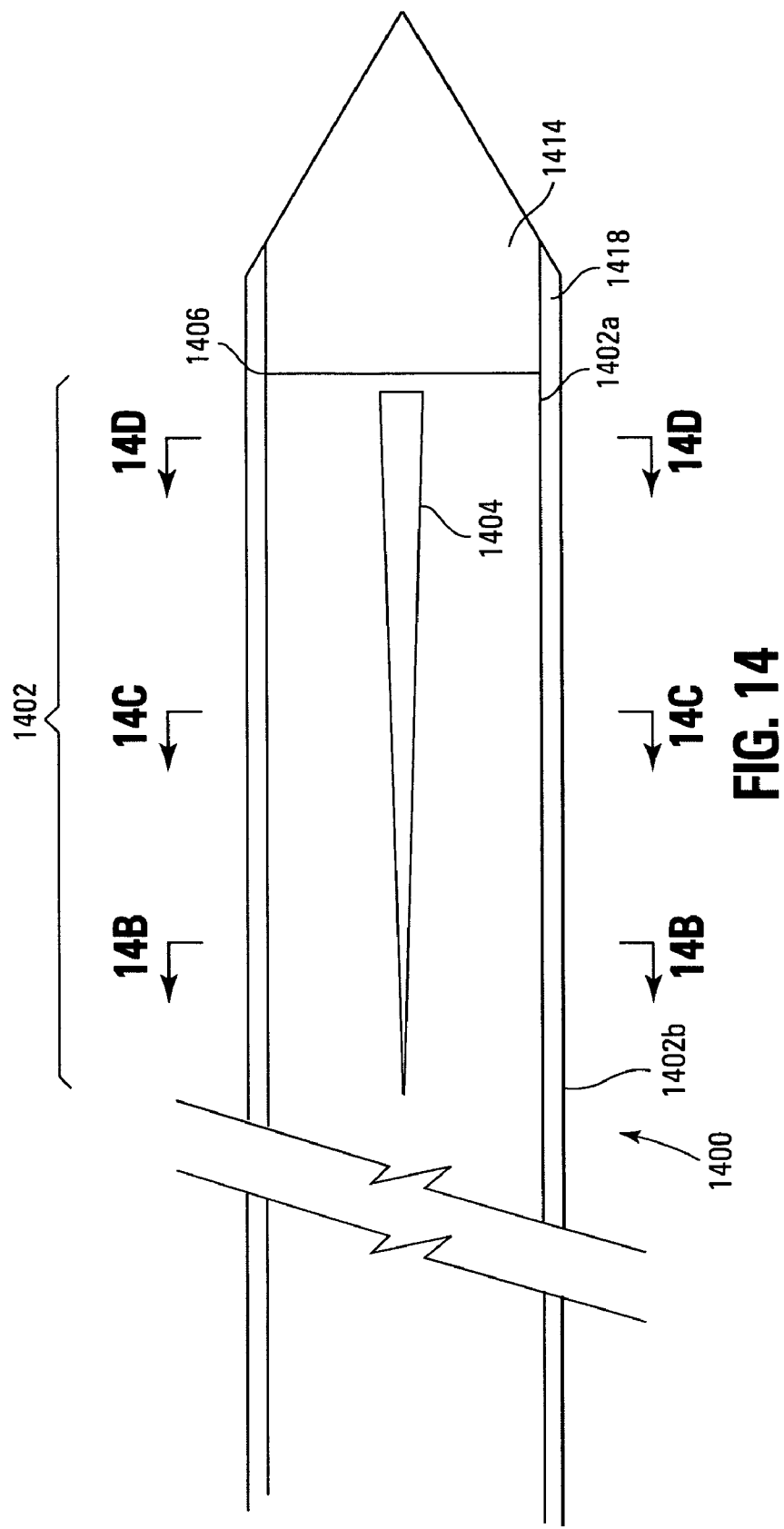
FIG. 14 shows the distal end of a light diffusing device of the present invention having a continuous opening extending distally wider through the cladding. The device is sheathed and a piercing tip is attached to the distal end of the device.
Figure 14A:
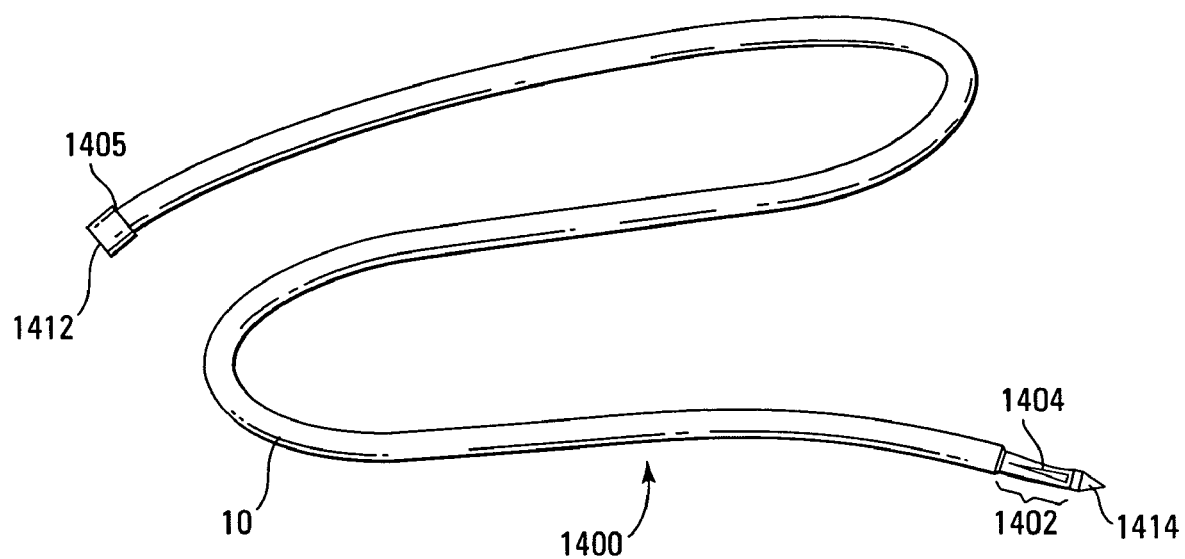
FIG. 14A is a plan view of the light diffusing device shown in FIG. 14.
Figure 14B:
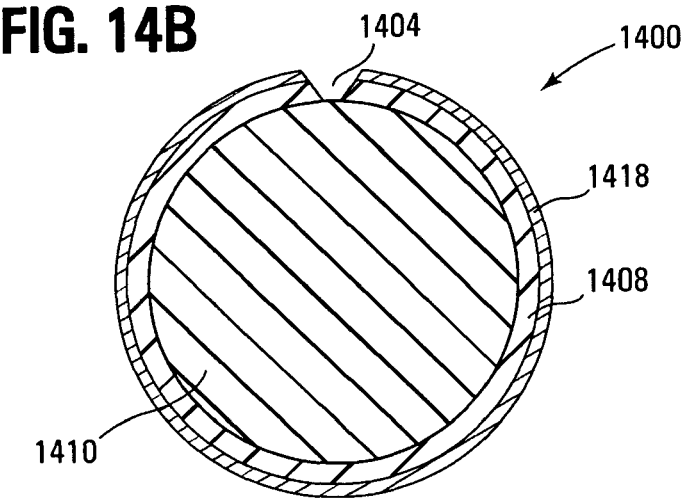
FIG. 14B is a lateral cross section taken through the lines 14B-14B as shown in FIG. 14, showing the opening through the sheathing and cladding and into the core fiber having a relatively narrow width.
Figure 14C:
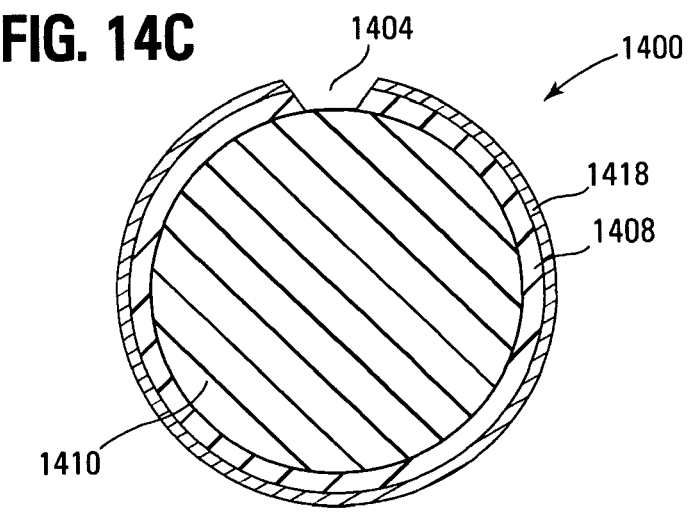
FIG. 14C is a lateral cross section taken through the lines 14C-14C as shown in FIG. 14, showing the opening through the sheathing and cladding and into the core fiber having a relatively intermediate width.
Figure 14D:
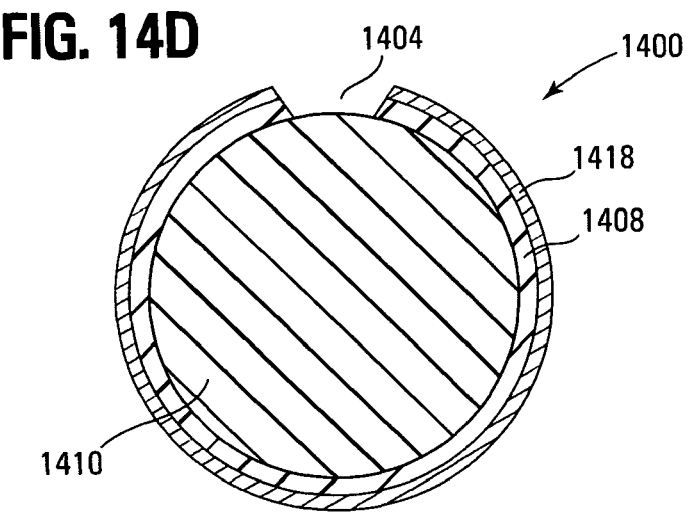
FIG. 14D is a lateral cross section taken through the lines 14D-14D as shown in FIG. 14, showing the opening through the sheathing and cladding and into the core fiber having a relatively wide width.

FIG. 14 shows the light emitting section 1402 of an embodiment of the light diffusing device 1400 of the present invention. FIG. 14A shows the entire light diffusing device 1400, including a connector 1412 attached to the proximal end 1405 allowing the light diffusing device 1400 to be connected to a light source (not shown). As best shown in FIGS. 14B, 14C, 14D the light diffusing device 1400 is made for reasons of economy as well as flexibility from a plastic optical fiber 10 approximately 1 mm in diameter which comprises a light transmitting core fiber 1410 made of PMMA (acrylic) surrounded by cladding 1408 made of fluorinated polymers. It should be mentioned that other kinds of light transmitting fibers (not shown) could also be used and are therefore contemplated by and within the scope of the invention. In this embodiment, the light diffusing device 1400 is also covered by sheathing 1418 which serves to further protect the device 1400. The sheathing 1418 can be polymeric materials such as PTFE, polyester, polyurethane, PMMA, PEBAX or other suitable materials and can be applied by heat shrink, non-heat shrink techniques or adhesive techniques (i.e., epoxy and uv cured materials, among others). The core fiber 1410 and cladding 1408 have different indexes of refraction, which enables light entering the light diffusing device 1400 at the connector 1412 to be transmitted along the length of the light diffusing device 1400 and thereby transmitted to a more distal location. The light diffusing device 1400 defines a distal end 1406 to which is attached a piercing tip 1414, preventing the escape of the transmitted light energy from an open distal end (not shown) of the core fiber 1410. The piercing tip 1414 also allows the device 1400 to pierce or penetrate and thereby be implanted into tissue following the application of gentle force by the physician. In one embodiment, the piercing tip 1414 is made of machined (sharpened) stainless steel, however, this is not intended to be limiting as other metallic, composite and polymeric materials could also be used. Using appropriate medical grade adhesives, the piercing tip 1414 is attached to the distal end 1406 of the light diffusing device 1400 after the distal end 1406 is roughened by such means as sandpaper, sandblasting, chemical degradation or other abrasive or erosive methods.

The light emitting section 1402 is defined by an extended light port 1404 which is cut through the cladding 1408 exposing the core fiber 1400 allowing the transmitted light to be emitted from the light diffusing device 1400. While a single extended light port 1404 is shown in FIGS. 14-14D, this is for purposes of illustration only and the invention could also include multiple extended light ports 1404 (not shown). As best shown in FIGS. 14B, 14C, 14D, the light emitting section 1402 is characterized by the light port 1404 extending progressively wider through the cladding 1408 as the distal end is reached. Restated, the progressively wider light port 1404 toward the distal end results in a lesser exposed core fiber 1410 surface area at the proximal end 1402b of the light emitting section 1402 and a greater exposed core fiber 1410 surface area at the distal end 1402a of the light emitting section 1402, allowing a greater quantity of light to be available at the distal end 1402a of the light emitting section 1402. The reason for this is that if the width of the light port 1404 was consistent (not shown), more light would be emitted from the proximal end 1402b of the light port 1404, leaving less light available to be emitted from the distal end 1402a of the light port 1404. The result of a uniform width light port 1404 (not shown) would be an optical fiber (not shown) having uneven light distribution, with more intensity toward the proximal end and less toward the distal end. The embodiment of the light diffusing device 1400 shown in FIG. 14 thus evenly emits the transmitted light energy along the length of the light emitting section 1402, allowing safer and more precise photodynamic therapy.

Figure 15:
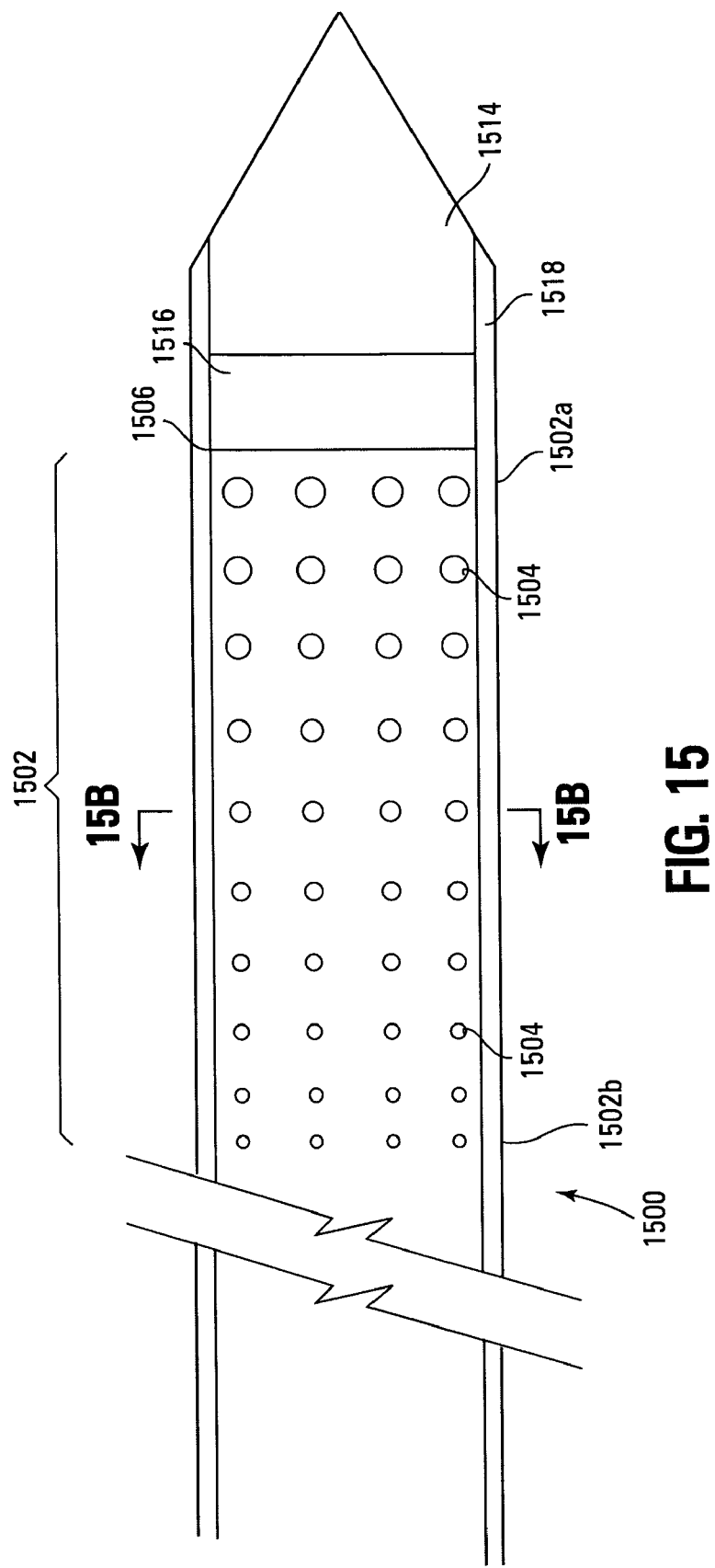
FIG. 15 shows the distal end of an embodiment of the light diffusing device of the present invention having a plurality of open areas through the cladding distally increasing in size. The device is sheathed and a piercing tip is attached to the distal end of the device. Fluorescent material is embedded in the sheathing.
Figure 15A:
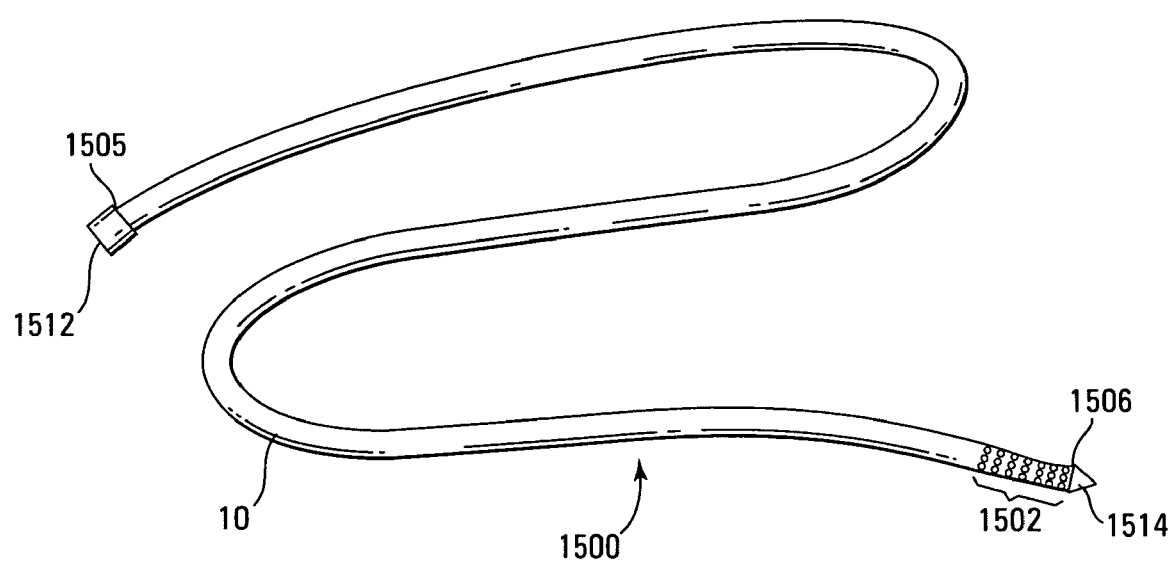
FIG. 15A is a plan view of the light diffusing device shown in FIG. 15.

FIG. 15 shows the light emitting section 1502 of an embodiment of a light diffusing device 1500 of the present invention. FIG. 15A shows the entire light diffusing device 1500, including a connector 1512 attached to the proximal end 1505 allowing the light diffusing device 1500 to be connected to a light source (not shown). As best shown in FIG. 15B the light diffusing device 1500 is made for reasons of economy as well as flexibility from a plastic optical fiber 10 approximately 1 mm in diameter which comprises a light transmitting core fiber 1510 made of PMMA (acrylic) surrounded by cladding 1508 made of fluorinated polymers. It should be mentioned that other kinds of light transmitting fibers (not shown) could also be used and are therefore contemplated by and within the scope of the invention. In this embodiment, the light diffusing device 1500 is also covered by sheathing 1518 which serves to further protect the device 1500. The sheathing 1518 can be polymeric materials such as PTFE, polyester, polyurethane, PMMA, PEBAX or other suitable materials and can be applied by heat shrink, non-heat shrink techniques or adhesive techniques (i.e., epoxy and uv cured materials, among others). The core fiber 1510 and cladding 1508 have different indexes of refraction, which enables light entering the light diffusing device 1500 at a proximal location to be transmitted along the length of the light diffusing device 1500 and thereby transmitted to a more distal location. The light diffusing device 1500 defines a distal end 1506 which comprises a piercing tip 1514, preventing the escape of the transmitted light energy from an open distal end (not shown) of the core fiber 1510. The piercing tip 1514 also allows the device 1500 to pierce or penetrate tissue following the application of gentle force by the physician, allowing the device 1500 to be implanted into tissue. In one embodiment, the piercing tip 1514 is made of machined (sharpened) stainless steel, however, this is not intended to be limiting as other metallic, composite and polymeric materials could also be used. In this embodiment a section of fluorescent material 1516 is attached to the distal end 1506 of the optical fiber 10 using appropriate medical grade adhesive before attaching the piercing tip 1514. Using appropriate medical grade adhesives, the piercing tip 1514 is then attached to the distal end 1506 of the light diffusing device 1500 after the distal end (unnumbered) of the fluorescent material 1516 is roughened by such means as sandpaper, sandblasting, chemical degradation or other abrasive methods. The fluorescent material 1516 emits a signal when illuminated by light energy having a wavelength at least at an excitation wavelength and above and thus functions as a fluorescence feedback indicator. In this configuration, when the laser light source (not shown) is energized fluorescence occurs at the distal end 1506 and is detected at the light source console (not shown) to verify the light diffusing device 1500 is valid and functioning properly. In another embodiment (not shown) the end piece 1514 may be omitted and replaced by other light blocking mechanisms including opaque epoxy or plastic materials.

The light emitting section 1502 is defined by a plurality of light ports 1504 which extend through the cladding 1508 exposing core fiber 1510 allowing the transmitted light energy to be emitted from the light diffusing device 1500. As best shown in FIG. 15, the light emitting section 1502 is characterized by the light ports 1504 progressively exposing a greater core fiber 1510 surface area as the distal end 1506 is reached. The light ports 1504 are conically shaped and spacing may vary in diameter between 0.003 inches to 0.006 inches. Restated, progressively greater sized light ports 1504 toward the distal end 1502a result in a lesser exposed core fiber 1510 surface area at the proximal end 1502b of the light emitting section 1502 and a greater exposed core fiber 1510 surface area at the distal end 1502a of the light emitting section 1502, allowing a greater quantity of light to be available at the distal end 1506 of the light emitting section 1502. The reason for this is that if the surface area of the light ports 1504 was consistent (not shown), more light would be emitted from the more proximally located light ports 1504, leaving less light available to be emitted from the more distally located light ports 1504. The result of similarly sized light ports 1504 (not shown) would be an optical fiber (not shown) having uneven light distribution, with more intensity toward the proximal end and less toward the distal end. The embodiment of the light diffusing device 1500 shown in FIGS. 15-15B thus evenly emits the transmitted light energy along the length of the light emitting section 1502, allowing safer and more precise photodynamic therapy.

Figure 16:
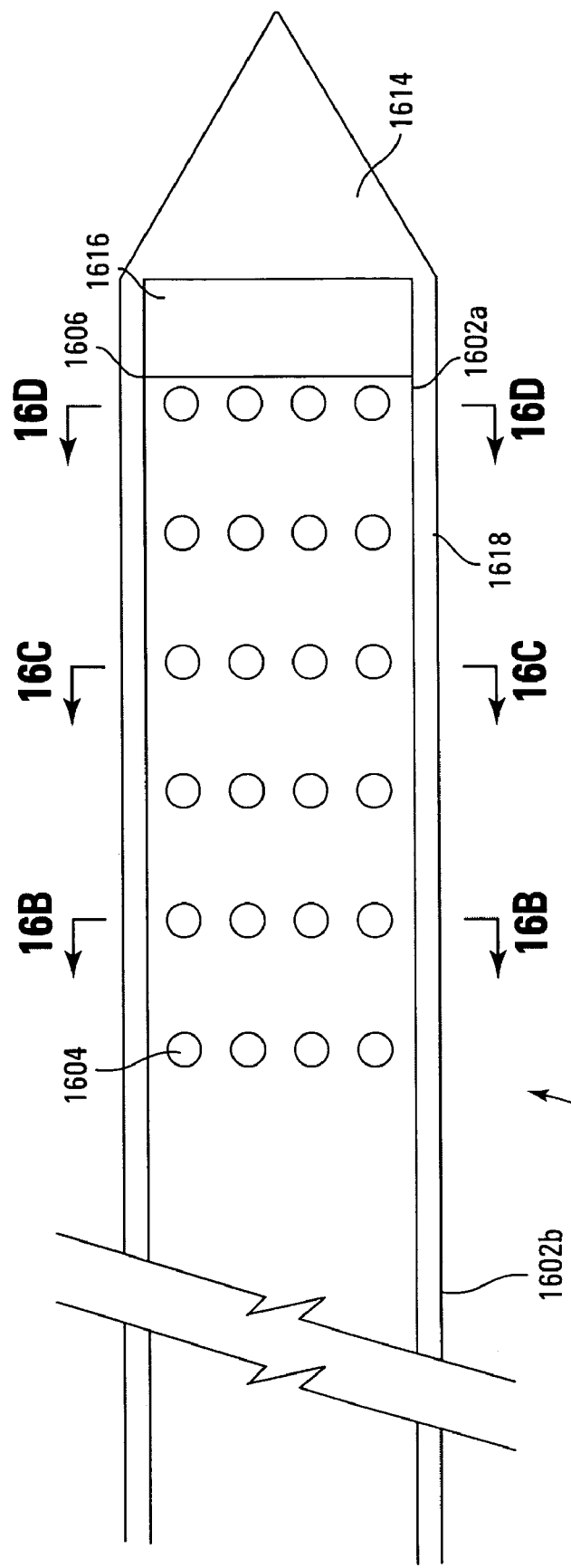
FIG. 16 shows the distal end of an embodiment of the light diffusing device of the present invention having a plurality of similarly sized open areas through the cladding distally increasing in depth into the core fiber. The device is sheathed and the sheathing is configured on the distal end to be able to pierce tissue. Fluorescent material is embedded in the sheathing.
Figure 16A:
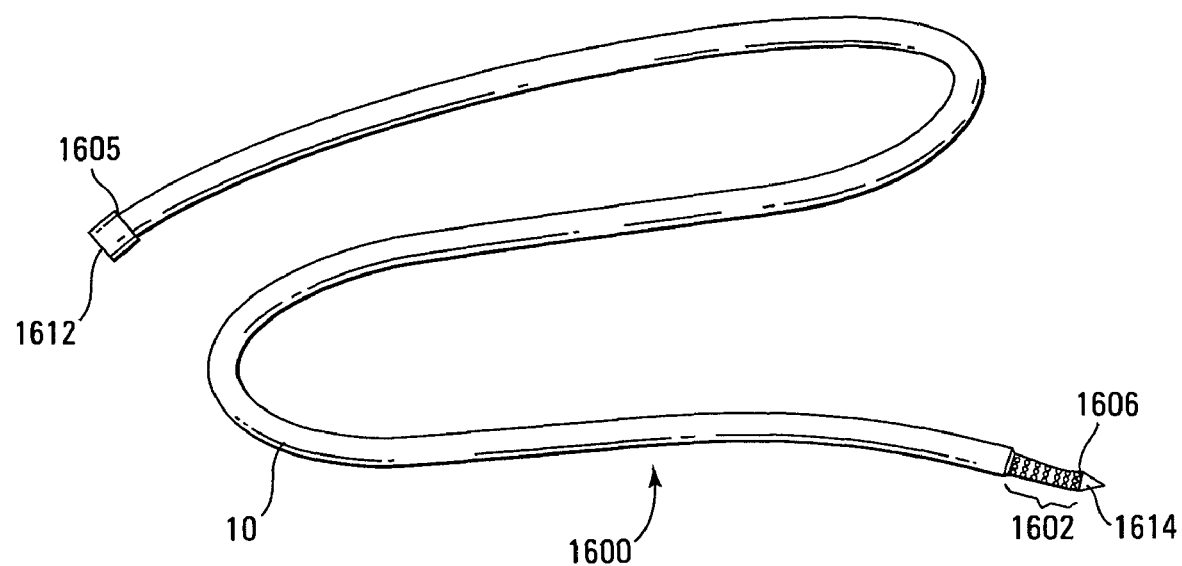
FIG. 16A is a plan view of the light diffusing device shown in FIG. 16.
Figure 16B:
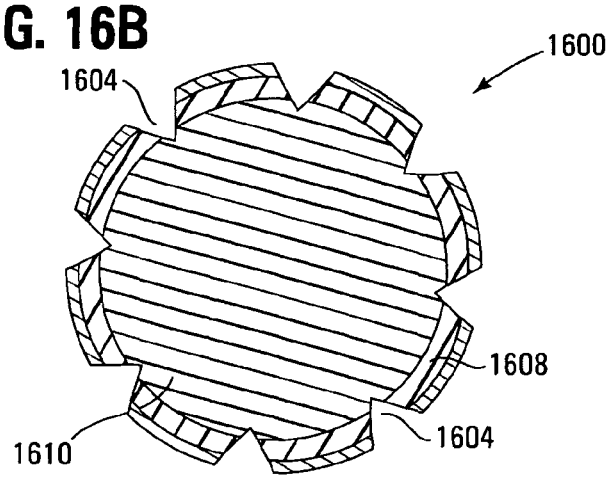
FIG. 16B is a lateral cross section taken through the lines 16B-16B as shown in FIG. 16, showing openings through the cladding and into the core fiber having a relatively shallow depth.
Figure 16C:
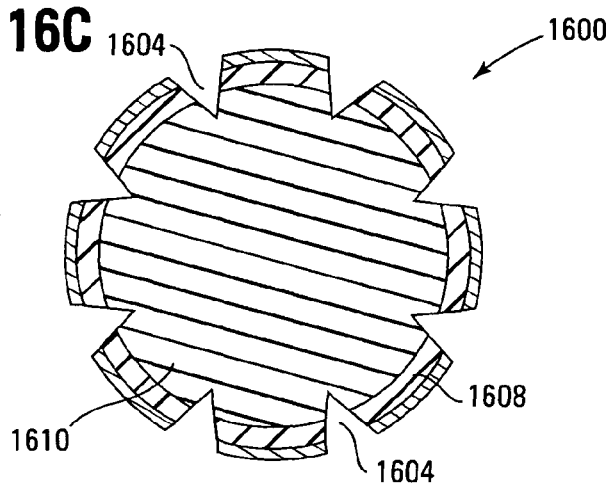
FIG. 16C is a lateral cross section taken through the lines 16C-16C as shown in FIG. 16, showing openings through the cladding and into the core fiber having a relatively intermediate depth.
Figure 16D:
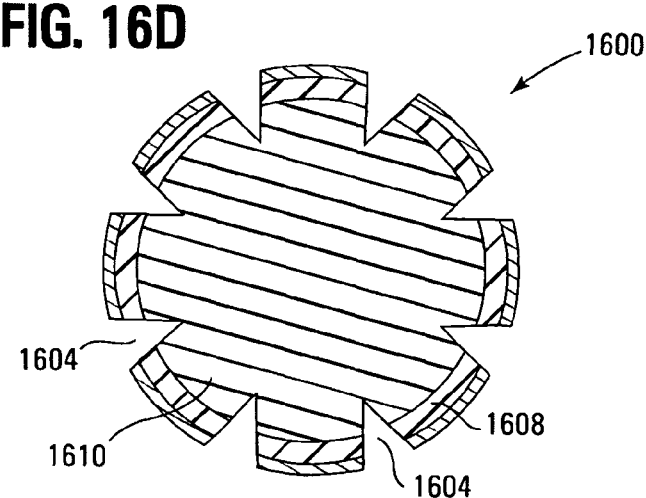
FIG. 16D is a lateral cross section taken through the lines 16D-16D as shown in FIG. 16, showing openings through the cladding and into the core fiber having a relatively deep depth.

FIG. 16 shows the light emitting section 1602 of an embodiment of a light diffusing device 1600 of the present invention. FIG. 16A shows the entire light diffusing device 1600, including a connector 1612 attached to the proximal end 1605 allowing the light diffusing device 1600 to be connected to a light source (not shown). As best shown in FIGS. 16B, 16C, 16D the light diffusing device 1600 is made for reasons of economy as well as flexibility from a plastic optical fiber 10 approximately 1 mm in diameter which comprises a light transmitting core fiber 1610 made of PMMA (acrylic) surrounded by cladding 1608 made of fluorinated polymers. It should be mentioned that other kinds of light transmitting fibers (not shown) could also be used and are therefore contemplated by and within the scope of the invention. In this embodiment, the light diffusing device 1600 is also covered by sheathing 1618 which serves to further strengthen and protect the device 1600. The sheathing 1618 can be polymeric materials such as PTFE, polyester, polyurethane, PMMA, PEBAX or other suitable materials and can be applied by heat shrink, non-heat shrink techniques or adhesive techniques (i.e., epoxy and uv cured materials, among others). The core fiber 1610 and cladding 1608 have different indexes of refraction, which enables light entering the light diffusing device 1600 at the connector 1612 to be transmitted along the length of the light diffusing device 1600 and thereby transmitted to a more distal location. The optical fiber 10 defines a distal end 1606 to which a section of fluorescent material 1616 is attached using appropriate medical grade adhesive. The fluorescent material 1616 emits a signal when illuminated by light energy having a wavelength at least at an excitation wavelength and above and thus functions as a fluorescence feedback indicator. In this configuration, when the laser light source (not shown) is energized fluorescence occurs at the distal end 1606 and is detected at the light source console (not shown) to verify the light diffusing device 1600 is valid and functioning properly. In this embodiment, the piercing tip of other embodiments is replaced by encapsulating the fluorescent material 1616 with sheathing 1618 which is hardened and sharpened to form a piercing distal end 1614. This allows the device 1600 to pierce or penetrate tissue upon the application of gentle force by the physician.

The light emitting section 1602 is defined by a plurality of light ports 1604 which extend through the cladding 1608 into the core fiber 1600 allowing the transmitted light to be emitted from the light diffusing device 1600. As best shown in FIGS. 16B, 16C, 16D, the light emitting section 1602 is characterized by the light ports 1604 having a similar surface area that extend progressively deeper into the core fiber 1610 as the distal end 1602a is reached. The light ports 1604 are conically shaped and the depth may vary between 0.004 inches to 0.008 inches. Restated, progressively deeper, similarly sized light ports 1604 toward the distal end 1602a result in a lesser exposed core fiber 1610 surface area at the proximal end 1602b of the light emitting section 1602 and a greater exposed core fiber 1610 surface area at the distal end 1602a of the light emitting section 1602, allowing a greater quantity of light to be available at the distal end 1602a of the light emitting section 1602. The reason for this is that if the size and depth of light ports 1604 was consistent (not shown), more light would be emitted from the more proximally located light ports 1604, leaving less light available to be emitted from the more distally located light ports 1604. The result of similarly sized and depth light ports 1604 (not shown) would be an optical fiber (not shown) having uneven light distribution, with more intensity toward the proximal end and less toward the distal end. The embodiment of the light diffusing device 1600 shown in FIG. 16 thus evenly emits the transmitted light energy along the length of the light emitting section 1602, allowing safer and more precise photodynamic therapy.

Figure 17:
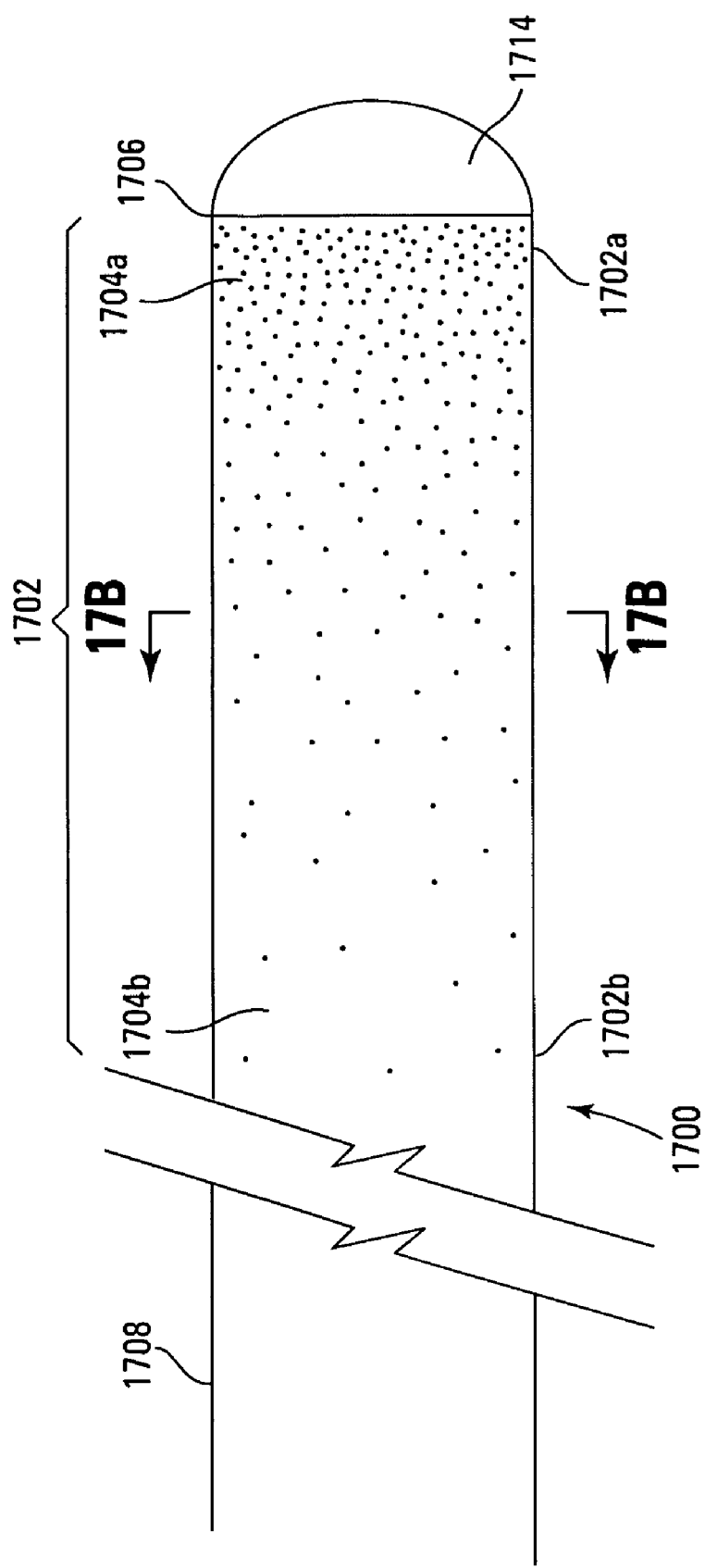
FIG. 17 shows the distal end of an embodiment of the light diffusing device of the present invention having cladding covering the light diffusing section with the exposed cladding progressively distally rougher.
Figure 17A:
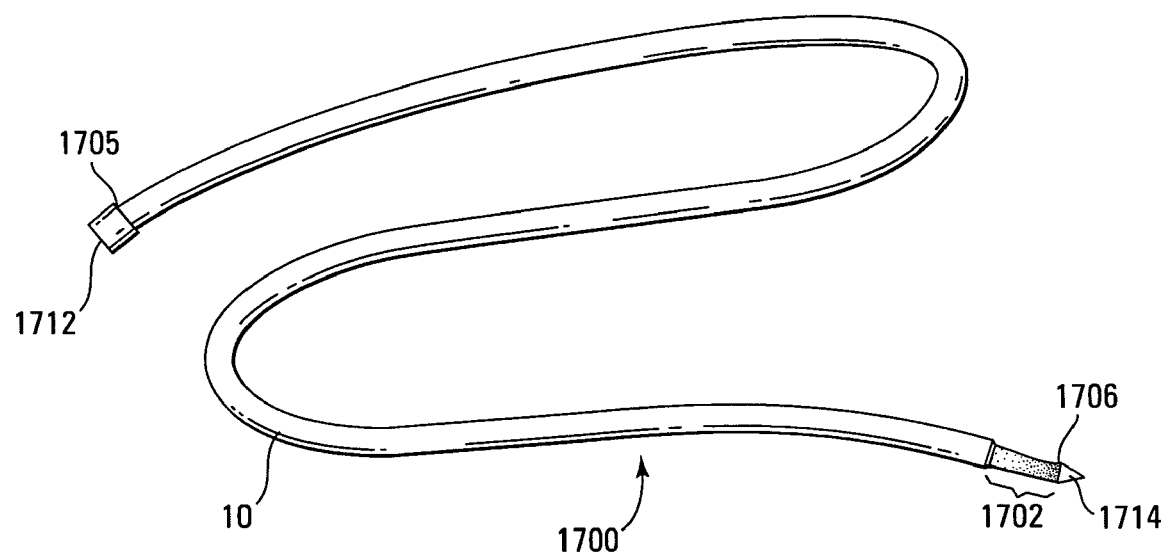
FIG. 17A is a plan view of the light diffusing device shown in FIG. 17.

FIG. 17 shows the light emitting section 1702 of an embodiment of the light diffusing device 1700 of the present invention. A plan view of the light emitting section as shown in FIG. 17A shows the entire light diffusing device 1700, including a connector 1712 attached to the proximal end 1705 allowing the light diffusing device 1700 to be connected to a light source (not shown). As best shown in FIG. 17B the light diffusing device 1700 is made for reasons of economy as well as flexibility from a plastic optical fiber 10 approximately 1 mm in diameter which comprises a light transmitting core fiber 1710 made of PMMA (acrylic) surrounded by cladding 1708 made of fluorinated polymers. It should be mentioned that other kinds of light transmitting fibers (not shown) could also be used and are therefore contemplated by and within the scope of the invention. The core fiber 1710 and cladding 1708 have different indexes of refraction, which enables light entering the light diffusing device 1700 at the connector 1712 to be transmitted along the length of the light diffusing device 1700 and thereby transmitted to a more distal location. The light diffusing device 1700 defines a distal end 1706 to which is attached an opaque end piece 1714, preventing the escape of the transmitted light energy from an open distal end (not shown) of the core fiber 1710. In one embodiment, the end piece 1714 is made of stainless steel. Using appropriate medical grade adhesives, the end piece 1714 is attached to the distal end 1706 of the light diffusing device 1700 after the distal end 1706 is roughened by such means as sandpaper, sandblasting, chemical degradation or other abrasive methods. In another embodiment (not shown) the end piece 1714 may be omitted and replaced by other light blocking mechanisms including opaque epoxy or plastic materials. In an alternative embodiment (not shown) the light diffusing device 1700 may be encased in a transparent protective sheath (not shown) which provides an additional degree of integrity as well as smoothness.

In this embodiment the light diffusing device 1700 the cladding 1708 is not removed. The light emitting section 1702 is defined by progressively distally roughening the surface of the cladding 1708 defining the light emitting section 1702 allowing an increased amount of transmitted light to be emitted from the light diffusing device 1700. As best shown in FIG. 17 the light emitting section 1702 is characterized by the light emitting section 1702 having a relatively smooth area 1704b which becomes progressively rougher 1704a along the core fiber 1710 as the distal end 1702a is reached. Restated, the progressively rougher light emitting section 1702 toward the distal end 1702a results in a lesser exposed core fiber 1710 surface area at the proximal end 1702b of the light emitting section 1702 and a greater exposed core fiber 1710 surface area at the distal end 1702a of the light emitting section 1702, allowing a greater quantity of light to be available at the distal end (unnumbered) of the light emitting section 1702. The reason for this is that if the roughness of the light emitting section 1702 was consistent (not shown), more light would be emitted from the proximal end of the light emitting section 1702, leaving less light available to be emitted from the distal end of the light emitting section 1702. The result of a uniform roughness light emitting section 1702 (not shown) would be a light diffusing device (not shown) having uneven light distribution, with more intensity toward the proximal end and less toward the distal end. The embodiment of the light diffusing device 1700 shown in FIG. 17 thus evenly emits the transmitted light energy along the length of the light emitting section 1702, allowing safer and more precise photodynamic therapy.

The light ports 104, 204, 304, 404, 504, 1204, 1304, 1404, 1504, 1604 and removed core fiber sections 604, 704, 804, 904, 1004 are created by securing a virgin plastic optical fiber (not shown) in a fixture (not shown) and then energizing a $CO_2$ laser (not shown) focused in the appropriate location(s). In one embodiment the fixture (not shown) is translated only on the X axis which moves longitudinally and rotates in order to create the light ports 104, 304, 404, 1204, 1304, 1404, 1504, 1604 and removed core fiber sections 604, 704, 804, 904, 1004. In embodiments 200, 500, 1400, 1500, 1600 which have a wider light port 204, 504, 1404, 1504, 1604, removed core fiber section 900 or deeper light port 300, 400, is required, the fixture (not shown) may additionally translate in the Y axis, moving the $CO_2$ laser closer to the virgin optical fiber (not shown). In another embodiment, repositioning of the optical fiber (not shown) in the fixture (not shown) may be required to allow for the creation of light ports 104, 204, 304, 404, 504, 1104, 1204, 1304, 1404, 1504, 1604 or removed core fiber sections 604, 704, 804, 904, 1004 that would be covered by the mandrel during an earlier laser drilling treatment. When energized, the laser pulse of the $CO_2$ laser (not shown) may have a 10.6 micron wavelength at 5 watts with a pulse duration between approximately 0.0003 to 0.0010 seconds. This results in controlled removal of the cladding 108, 208, 308, 408, 508, 1104, 1204, 1304, 1404, 1504, 1604 and in some cases part of the core fiber 110, 210, 310, 410, 510, 610, 710, 810, 910, 1010, 1110, 1210, 1310, 1410, 1510, 1610 without unduly damaging the core fiber 110, 210, 310, 410, 510, 610, 710, 810, 910, 1010, 1110, 1210, 1310, 1410, 1510, 1610. In the case of the embodiment of the light diffusing device 1100 the cladding is first removed from the section of the optical fiber 10 desired to become the light emitting section 1102, in the embodiment as shown, toward the distal end of the light diffusing device 1100. The embodiment of the light diffusing device 1700 does not require removal of any cladding 1708. Next, the light emitting section 1102, 1702 is treated with abrasives such as sandpaper, sand blasting or other abrasive techniques, starting at the proximal end 1102b, 1702b of the light emitting section 1102, 1702 and progressing for a longer period in a distal direction until the distal end 1102a, 1702a is reached. This results in a light emitting section 1102, 1702 which is progressively rougher in a distal direction.

Use

Using the light diffusing device 100, 200, 300, 400, 500, 600, 700, 800, 900, 1000, 1100, 1200, 1300, 1400, 1500, 1600, 1700 of the present invention involves initially treating the patient at the treatment site with a photosensitizing agent such as methylene blue or another of many photosensitizing agents well known in the art. Depending on the nature of the photodynamic therapy treatment, a period of time may be required to allow for absorption of the particular photosensitizing agent into the affected tissue. The light diffusing device 100, 200, 300, 400, 500, 600, 700, 800, 900, 1000, 1100, 1200, 1300, 1400, 1500, 1600, 1700 is removed from sterile packaging followed by positioning it in the treatment area. In the embodiments 1200, 1300, 1400, 1500, 1600 configured to be tissue piercing or penetrating, gentle pressure is applied to the device 1200, 1300, 1400, 1500, 1600 by the physician, causing it to become implanted into the intended tissue requiring treatment. Via the connector 112, 212, 312, 412, 512, 612, 712, 812, 912, 1012, 1112, 1212, 1312, 1412, 1512, 1612, 1712 the light diffusing device 100, 200, 300, 400, 500, 600, 700, 800, 900, 1000, 1100, 1200, 1300, 1400, 1500, 1600, 1700 is connected to a light source (not shown) capable of producing light in the appropriate wavelength which varies with the particular photosensitizing agent used and treatment prescribed, followed by energizing the light source at the beginning of treatment. The light source is then energized for the prescribed length of time and intensity (which also varies with the particular photosensitizing agent used) then de-energized at the conclusion. Following the conclusion of treatment, the light diffusing device 100, 200, 300, 400, 500, 600, 700, 800, 900, 1000, 1100, 1200, 1300, 1400, 1500, 1600, 1700 is disposed of.

What is claimed is:

1. A light diffusing device, comprising: an optical fiber defining a longitudinal dimension, a lateral dimension, a proximal end, a distal end wherein:
   a) the optical fiber includes
      (i) a core fiber; and
      (ii) a cladding that covers at least one portion of the core fiber and has a different index of refraction than the core fiber, which enables light entering the proximate end of the optical fiber to transmit along length of the optical fiber toward the distal end of the optical fiber;
   b) the optical fiber includes a light emitting section and at least one non-light emitting section;
   c) the light emitting section is located outside the distal end of the optical fiber and includes a proximate end and a distal end;
   d) the light emitting section is defined by at least one removed core fiber section;
   e) a portion of the cladding and a portion of the core fiber located beneath the portion of the cladding are removed to form each of the at least one removed core fiber section and the removal of the portion of the core fiber increases surface area of the core fiber;
   f) the at least one removed core fiber section exposes a progressively increasing amount of the surface area of the core fiber in a distal direction within the light emitting section, resulting in a desired distribution of the light emitted from the light emitting section.

2. The light diffusing device of claim 1 wherein the optical fiber is a plastic optical fiber.

3. The light diffusing device of claim 1 wherein the light emitting section is proximate the distal end of the optical fiber.

4. The light diffusing device of claim 1 further comprising an end piece attached to the distal end of the optical fiber wherein the end piece prevents the light from emitting from the distal end of the optical fiber.

5. The light diffusing device of claim 4 the end piece is a piercing tip capable of penetrating tissue.

6. The light diffusing device of claim 4 further comprising fluorescent material between the end piece and the distal end of the optical fiber, wherein when light having at least an excitation frequency is transmitted to the fluorescent material through the optical fiber a light energy signal is generated indicating the light diffusing device is valid.

7. The light diffusing device of claim 1 wherein the at least one removed core fiber section is comprised of a plurality of similarly sized removed core fiber sections and having a distally increasing density, resulting in greater number of removed core fiber sections at the distal end of the light emitting section and lesser number of removed core fiber sections at the proximal end of the light emitting section.

8. The light diffusing device of claim 7 wherein spacing between each of the plurality of similarly sized light ports ranges between 0.022 inches to 0.040 inches.

9. The light diffusing device of claim 1 wherein the at least one removed core fiber section is comprised of a plurality of removed core fiber sections having a distally increasing diameter, resulting in greater exposed core fiber surface area at the distal end of the light emitting section and lesser exposed core fiber surface area at the proximal end of the light emitting section.

10. The light diffusing device of claim 9 wherein the diameter of each of the plurality of removed core fiber sections ranges from 0.003 inches to 0.006 inches.

11. The light diffusing device of claim 1 wherein the at least one removed core fiber section is comprised of a plurality of similarly sized removed core fiber sections having a distally increasing depth into the core fiber, resulting in greater exposed core fiber surface area at the distal end of the light emitting section and lesser exposed core fiber surface area at the proximal end of the light emitting section.

12. The light diffusing device of claim 11 wherein the depth of each of the plurality of removed core fiber sections ranges between 0.004 inches to 0.008 inches.

13. The light diffusing device of claim 1 wherein the at least one removed core fiber section is comprised of an extended removed core fiber section having a distally increasing depth into the core fiber, resulting in greater exposed core fiber surface area at the distal end of the light emitting section and lesser exposed core fiber surface area at the proximal end of the light emitting section.

14. The light diffusing device of claim 1 wherein the at least one removed core fiber section is comprised of an extended removed core fiber section having a distally increasing width, resulting in greater exposed core fiber surface area at the distal end of the light emitting section and lesser exposed core fiber surface area at the proximal end of the light emitting section.

15. The light diffusing device of claim 1 wherein the cladding within the light emitting section is completely removed.

16. The light diffusing device of claim 1 wherein at least a portion of the light diffusing device is covered by a sheath.

17. The light diffusing device of claim 1 wherein each of the at least one removed core fiber section is conically shaped.

18. A light diffusing device, comprising: an optical fiber defining a length, a diameter, a proximal end and a distal end and a core fiber at least partially covered by a cladding wherein a light emitting section is formed by selectively removing a portion of the cladding and a portion of the core fiber located beneath the removed portion of the cladding to form at least a single light port, such that a progressively distally increasing surface area of core fiber is exposed, resulting in an even distribution of light emitted from the light emitting section, the light emitting section further defining a distal end and a proximal end.

19. The light diffusing device of claim 18 wherein an end piece is attached to the distal end of the optical fiber wherein the end piece prevents the light from emitting from the distal end of the optical fiber.

20. The light diffusing device of claim 19 wherein the end piece is a piercing tip capable of penetrating tissue.

21. The light diffusing device of claim 19 further comprising fluorescent material attached to between the end piece and the distal end of the optical fiber, wherein the fluorescent material fluoresces when exposed to light having a wavelength at least at an excitation wavelength.

22. The light diffusing device of claim 18 wherein the optical fiber is a plastic optical fiber.

23. The light diffusing device of claim 22 wherein the at least a single light port is comprised of a plurality of similarly sized light ports having a distally increasing density, resulting in a greater number of light ports at the distal end of the light emitting section and a lesser number of light ports at the proximal end of the light emitting section.

24. The light diffusing device of claim 23 wherein spacing between each of the plurality of similarly sized light ports ranges between 0.022 inches to 0.040 inches.

25. The light diffusing device of claim 22 wherein the at least a single light port is comprised of a plurality of light ports having a distally increasing diameter, resulting in a greater exposed core fiber surface area at the distal end of the light emitting section and a lesser exposed core fiber surface area at the proximal end of the light emitting section.

26. The light diffusing device of claim 25 wherein the diameter of each of the plurality of the light ports ranges from 0.003 inches to 0.006 inches.

27. The light diffusing device of claim 22 wherein the at least a single light port is comprised of a plurality of similarly sized light ports having a distally increasing depth, resulting in a greater exposed core fiber surface area at the distal end of the light emitting section and a lesser exposed core fiber surface area at the proximal end of the light emitting section.

28. The light diffusing device of claim 27 wherein the depth of each of the plurality of similarly sized light ports ranges between 0.004 inches to 0.008 inches.

29. The light diffusing device of claim 22 wherein the at least a single light port is comprised of an extended light port having a distally increasing depth, resulting in a greater exposed core fiber surface area at the distal end of the light emitting section and a lesser exposed core fiber surface area at the proximal end of the light emitting section.

30. The light diffusing device of claim 22 wherein the at least a single light port is comprised of an extended light port having a distally increasing width, resulting in a greater exposed core fiber surface area at the distal end of the light emitting section and a lesser exposed core fiber surface area at the proximal end of the light emitting section.

31. The light diffusing device of claim 22 wherein the cladding within the light emitting section is completely removed.

32. The light diffusing device of claim 18 wherein at least a portion of the light diffusing device is covered by a sheath.

33. The light diffusing device of claim 18 wherein each of the at least a single light port is conically shaped.

34. A light diffusing device, comprising:
an optical fiber defining a longitudinal dimension, a lateral dimension, a proximal end, a distal end; and
an end piece that is attached to the distal end of the optical fiber, wherein:
a) the optical fiber includes
(i) a core fiber; and
(ii) a cladding that covers at least one portion of the core fiber and has a different index of refraction than the core fiber, which enables light entering the proximate end of the optical fiber to transmit along length of the optical fiber toward the distal end of the optical fiber;

b) the end piece prevents the light from emitting from the distal end of the optical fiber;

c) the optical fiber includes a light emitting section and at least one non-light emitting section;

d) the light emitting section is located outside the distal end of the optical fiber and includes a proximate end and a distal end;

e) the cladding is completely removed from the light emitting section;

f) the light emitting section is defined by at least one removed core fiber section;

g) a portion of the core fiber is removed in each of the at least one removed core fiber section and the removal of the portion of the core fiber increases surface area of the core fiber;

h) the at least one removed core fiber section exposes a progressively increasing amount of the surface area of the core fiber in a distal direction within the light emitting section; resulting in a desired distribution of the light emitted from the light emitting section; and i) a laser is used to create the at least one removed core fiber section.

* * * * *